US012806278B2

(12) United States Patent
Wantuch et al.

(10) Patent No.: US 12,806,278 B2
(45) Date of Patent: Nov. 24, 2026

(54) TETANUS TOXOID AND CRM-BASED PEPTIDES AND METHODS OF USE

(71) Applicant: UNIVERSITY OF GEORGIA RESEARCH FOUNDATION, INC., Athens, GA (US)

(72) Inventors: Paeton L. Wantuch, Athens, GA (US); Jeremy A. Duke, Athens, GA (US); Fikri Y. Avci, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 1085 days.

(21) Appl. No.: 17/778,211

(22) PCT Filed: Nov. 22, 2020

(86) PCT No.: PCT/US2020/061699
§ 371 (c)(1),
(2) Date: May 19, 2022

(87) PCT Pub. No.: WO2021/102389
PCT Pub. Date: May 27, 2021

(65) Prior Publication Data

US 2023/0211004 A1 Jul. 6, 2023

Related U.S. Application Data

(60) Provisional application No. 62/939,299, filed on Nov. 22, 2019.

(51) Int. Cl.
*C07K 5/00* (2006.01)
*A61K 47/64* (2017.01)

(52) U.S. Cl.
CPC ........ *A61K 47/646* (2017.08); *A61K 47/6415* (2017.08)

(58) Field of Classification Search
None
See application file for complete search history.

(56) References Cited

U.S. PATENT DOCUMENTS 4,703,004 A 10/1987 Hopp et al.
4,782,137 A 11/1988 Hopp et al.
5,594,115 A 1/1997 Sharma
5,935,824 A 8/1999 Sgarlato
9,657,691 B2 5/2017 Eguchi et al.
2012/0207754 A1 8/2012 Giacalone et al.

FOREIGN PATENT DOCUMENTS

CN 103495161 B 6/2019
WO WO 2019/036373 A2 2/2019
WO WO 2019/121687 A2 6/2019
WO WO 2019/173925 A1 9/2019
WO WO 2020/010016 A1 1/2020
WO WO 2020/064564 A1 4/2020
WO WO 2021/102389 A1 5/2021

OTHER PUBLICATIONS

Kamboji (The Journal of Infectious Disease, 2003, vol. 187, No. 10, pp. 1629-1638). (Year: 2003).*
Lucke (Biomaterials, 2018, vol. 172, pp. 105-115). (Year: 2018).*
Kwon (Molecular Pharmaceuticals, 2005, vol. 1, No. 2, pp. 83-91). (Year: 2005).*
Passwell (Infection and Immunity, 2001, vol. 69, No. 3, pp. 1351-1357) (Year: 2001).*
Tontini (Vaccine 2016, vol. 34, pp. 4235-4242). (Year: 2016).*
International Search Report and Written Opinion issued May 17, 2021 for International Application No. PCT/US2020/061699, filed Nov. 22, 2020; 21 pages.
Allen et al., Humanized immune system mouse models: progress, challenges and opportunities. Nat Immunol 20, 770-774 (2019).
Alter et al., Immune Correlate-Guided HIV Vaccine Design. Cell Host Microbe 24, 25-33 (2018).
Amin et al., Synthetic glycopeptides reveal the glycan specificity of HIV-neutralizing antibodies. Nat Chem Biol 9, 521-526 (2013).
Aoki et al., Dynamic developmental elaboration of N-linked glycan complexity in the *Drosophila melanogaster* embryo. J Biol Chem 282, 9127-9142 (2007).
Arnold et al., Substrate specificity of cathepsins D and E determined by N-terminal and C-terminal sequencing of peptide pools. *Eur J Biochem* 249, 171-179 (1997).
Avalos et al., Early BCR Events and Antigen Capture, Processing, and Loading on MHC Class II on B Cells. *Front Immunol* 5, 92 (2014).
Avci et al., A mechanism for glycoconjugate vaccine activation of the adaptive immune system and its implications for vaccine design. Nat Med 17, 1602-1609 (2011).
Avci, Novel strategies for development of next-generation glycoconjugate vaccines. *Curr Top Med Chem* 13, 2535-2540 (2013).
Avci et al., Isolation of carbohydrate-specific CD4(+) T cell clones from mice after stimulation by two model glycoconjugate vaccines. *Nat Protoc* 7, 2180-2192 (2012).
Baraldo et al., Combined conjugate vaccines: enhanced immunogenicity with the N19 polyepitope as a carrier protein. *Infect Immun* 73, 5835-5841 (2005).
Bentley et al., High-resolution, high-throughput HLA genotyping by next-generation sequencing. *Tissue Antigens* 74, 393-403 (2009).
Berti, Expanding polysaccharide-protein coupling of glycoconjugate vaccines. *J Biol Chem* 298, 101755 (2022).

(Continued)

*Primary Examiner* — Celine X Qian
(74) *Attorney, Agent, or Firm* — Mueting Raasch Group

(57) ABSTRACT

The present disclosure provides peptides derived from CRM197 and Tetanus toxoid that can be used to generate an immune response in an individual. The present disclosure includes isolated peptides and multimers of isolated peptides. Also provided are compositions that include the isolated peptide or the multimer. Further provided are methods, including methods for increasing the antigenicity of a compound, such as an antigen, and methods for inducing an immune response in a subject.

17 Claims, 16 Drawing Sheets

Specification includes a Sequence Listing.

(56) References Cited

OTHER PUBLICATIONS

Bixler et al., Synthetic peptide representing a T-cell epitope of CRM197 substitutes as carrier molecule in a Haemophilus influenzae type B (Hib) conjugate vaccine. *Adv Exp Med Biol* 251, 175-180 (1989).
Bozzacco et al., Mass spectrometry analysis and quantitation of peptides presented on the MHC II molecules of mouse spleen dendritic cells. *J Proteome Res* 10, 5016-5030 (2011).
Brown et al., T cell epitope "hotspots" on the HIV Type 1 gp120 envelope protein overlap with tryptic fragments displayed by mass spectrometry. *AIDS Res Hum Retroviruses* 21, 165-170 (2005).
Cai et al., Self-adjuvanting synthetic antitumor vaccines from MUC1 glycopeptides conjugated to T-cell epitopes from tetanus toxoid. *Angew Chem Int Ed Engl* 52, 6106-6110 (2013).
Calarese et al., Dissection of the carbohydrate specificity of the broadly neutralizing anti-HIV-1 antibody 2G12. *Proc Natl Acad Sci U S A* 102, 13372-13377 (2005).
Cao et al., Global site-specific N-glycosylation analysis of HIV envelope glycoprotein. *Nat Commun* 8, 14954 (2017).
Castelli et al., HLA-DP4, the most frequent HLA II molecule, defines a new supertype of peptide-binding specificity. *J Immunol* 169, 6928-6934 (2002).
Cheng et al., Glycoconjugate synthesis using chemoselective ligation. *Org Biomol Chem* 17, 2646-2650 (2019).
Cobb et al., Polysaccharide processing and presentation by the MHCII pathway. *Cell* 117, 677-687 (2004).
Conus et al., Cathepsins: key modulators of cell death and inflammatory responses. *Biochem Pharmacol* 76, 1374-1382 (2008).
Crotty, A brief history of T cell help to B cells. *Nat Rev Immunol* 15, 185-189 (2015).
Da Silva Antunes et al., Definition of Human Epitopes Recognized in Tetanus Toxoid and Development of an Assay Strategy to Detect Ex Vivo Tetanus CD4+ T Cell Responses. *PLoS One* 12, e0169086 (2017).
De Velasco et al., Synthetic peptides representing T-cell epitopes act as carriers in pneumococcal polysaccharide conjugate vaccines. *Infect Immun* 63, 961-968 (1995).
Demotz et al., The set of naturally processed peptides displayed by DR molecules is tuned by polymorphism of residue 86. *Eur J Immunol* 23, 425-432 (1993).
Demotz et al., Delineation of several DR-restricted tetanus toxin T cell epitopes. *J Immunol* 142, 394-402 (1989).
Denton et al., Humanized mouse models of HIV infection. *AIDS Rev* 13, 135-148 (2011).
Diethelm-Okita et al., Universal epitopes for human CD4+ cells on tetanus and diphtheria toxins. *J Infect Dis* 181, 1001-1009 (2000).
Diethelm-Okita et al., Epitope repertoire of human CD4+ T cells on tetanus toxin: identification of immunodominant sequence segments. *J Infect Dis* 175, 382-391 (1997).
Dongre et al., In vivo MHC class II presentation of cytosolic proteins revealed by rapid automated tandem mass spectrometry and functional analyses. *Eur J Immunol* 31, 1485-1494 (2001).
Duke et al., Harnessing galactose oxidase in the development of a chemoenzymatic platform for glycoconjugate vaccine design. *J Biol Chem* 298, 101453 (2022).
Eggink et al., Lack of complex N-glycans on HIV-1 envelope glycoproteins preserves protein conformation and entry function. *Virology* 401, 236-247 (2010).
Etlinger et al., Use of prior vaccinations for the development of new vaccines. *Science* 249, 423-425 (1990).
Falugi et al., Rationally designed strings of promiscuous CD4(+) T cell epitopes provide help to Haemophilus influenzae type b oligosaccharide: a model for new conjugate vaccines. *Eur J Immunol* 31, 3816-3824 (2001).
Farkas et al., Comparison of EDC and DMTMM efficiency in glycoconjugate preparation. *Int J Biol Macromol* 60, 325-327 (2013).
Fauci et al., Ending AIDS—is an HIV vaccine necessary? *N Engl J Med* 370, 495-498 (2014).
Feng et al., Thermostability of Well-Ordered HIV Spikes Correlates with the Elicitation of Autologous Tier 2 Neutralizing Antibodies. *PLoS Pathog* 12, e1005767 (2016).
Fong et al., beta-N-Acetylglucosamine (O-GlcNAc) is a novel regulator of mitosis-specific phosphorylations on histone H3. *J Biol Chem* 287, 12195-12203 (2012).
Forthal et al., Antibody from patients with acute human immunodeficiency virus (HIV) infection inhibits primary strains of HIV type 1 in the presence of natural-killer effector cells. J Virol 75, 6953-6961 (2001).
Fujita et al., Current status of multiple antigen-presenting peptide vaccine systems: Application of organic and inorganic nanoparticles. *Chem Cent J* 5, 48 (2011).
National Center for Biotechnology Information, National Library of Medicine, National Institutes of Health, GenBank Locus WP_003850266.1, Accession No. WP_003850266, "Multispecies: diphtheria toxin [Corynebacterium]," [online]. Bethesda, MD [retrieved on Mar. 25, 2024]. Retrieved from the Internet: <URL: ncbi.nlm.nih.gov/protein/WP_003850266.1>; 2 pgs.
National Center for Biotechnology Information, National Library of Medicine, National Institutes of Health, GenBank Locus WP_011100836.1, Accession No. WP_011100836, "tetanus neurotoxin TetX [Clostridium tetani]," [online]. Bethesda, MD [retrieved on Mar. 25, 2024]. Retrieved from the Internet: <URL: ncbi.nlm.nih.gov/protein/WP_011100836.1>; 2 pgs.
Geno et al., Pneumococcal Capsules and Their Types: Past, Present, and Future. *Clin Microbiol Rev* 28, 871-899 (2015).
Gildersleeve et al., Improved procedure for direct coupling of carbohydrates to proteins via reductive amination. *Bioconjug Chem* 19, 1485-1490 (2008).
Goldblatt, Conjugate vaccines. *Clin Exp Immunol* 119, 1-3 (2000).
Golding et al., Identification of homologous regions in human immunodeficiency virus I gp41 and human MHC class II beta 1 domain. I. Monoclonal antibodies against the gp41-derived peptide and patients' sera react with native HLA class II antigens, suggesting a role for autoimmunity in the pathogenesis of acquired immune deficiency syndrome. *J Exp Med* 167, 914-923 (1988).
Gonzalez-Galarza et al., Allele frequency net 2015 update: new features for HLA epitopes, KIR and disease and HLA adverse drug reaction associations. *Nucleic Acids Res* 43, D784-788 (2015).
Gowthaman et al., Identification of a T follicular helper cell subset that drives anaphylactic IgE. *Science* 365, (2019).
Gros et al., Prospective identification of neoantigen-specific lymphocytes in the peripheral blood of melanoma patients. *Nat Med* 22, 433-438 (2016).
Grotenbreg et al., Empty class II major histocompatibility complex created by peptide photolysis establishes the role of DM in peptide association. *J Biol Chem* 282, 21425-21436 (2007).
Guenaga et al., Structure-Guided Redesign Increases the Propensity of HIV Env to Generate Highly Stable Soluble Trimers. *J Virol* 90, 2806-2817 (2015).
Gunther et al., SuperHapten: a comprehensive database for small immunogenic compounds. *Nucleic Acids Res* 35, D906-910 (2007).
Hatziioannou et al., Animal models for HIV/AIDS research. *Nat Rev Microbiol* 10, 852-867 (2012).
Haynes et al., Cardiolipin polyspecific autoreactivity in two broadly neutralizing HIV-1 antibodies. *Science* 308, 1906-1908 (2005).
Haynes et al., HIV-1 autoreactive antibodies: are they good or bad for HIV-1 prevention? *Nat Struct Mol Biol* 17, 543-545 (2010).
Hunt et al., Peptides presented to the immune system by the murine class II major histocompatibility complex molecule I-Ad. *Science* 256, 1817-1820 (1992).
Jackson et al., The central role played by peptides in the immune response and the design of peptide-based vaccines against infectious diseases and cancer. *Curr Drug Targets* 3, 175-196 (2002).
Jan et al., Heterogeneity in glycan composition on the surface of HIV-1 envelope determines virus sensitivity to lectins. *PLoS One* 13, e0194498 (2018).
Jennewein et al., The Immunoregulatory Roles of Antibody Glycosylation. *Trends Immunol* 38, 358-372 (2017).

(56) References Cited

OTHER PUBLICATIONS

Jennings et al., Immunochemistry of groups A, B, and C meningococcal polysaccharide-tetanus toxoid conjugates. *J Immunol* 127, 1011-1018 (1981).
Kerblat et al., Tetanus toxin L chain is processed by major histocompatibility complex class I and class II pathways and recognized by CD8+ or CD4+ T lymphocytes. *Immunology* 100, 178-184 (2000).
Klein et al., Antibodies in HIV-1 vaccine development and therapy. *Science* 341, 1199-1204 (2013).
Kwong et al., Broadly neutralizing antibodies and the search for an HIV-1 vaccine: the end of the beginning. *Nat Rev Immunol* 13, 693-701 (2013).
Lan et al., Reconstitution of a functional human immune system in immunodeficient mice through combined human fetal thymus/liver and CD34+ cell transplantation. *Blood* 108, 487-492 (2006).
Lee et al., Structure of a human insulin peptide-HLA-DQ8 complex and susceptibility to type 1 diabetes. *Nat Immunol* 2, 501-507 (2001).
Leonard et al., Antigen processing of the heptavalent pneumococcal conjugate vaccine carrier protein CRM(197) differs depending on the serotype of the attached polysaccharide. *Infect Immun* 71, 4186-4189 (2003).
Li et al., Profiling pneumococcal type 3-derived oligosaccharides by high resolution liquid chromatography-tandem mass spectrometry. *J Chromatogr A* 1397, 43-51 (2015).
Li et al., Proximal glycans outside of the epitopes regulate the presentation of HIV-1 envelope gp120 helper epitopes. *J Immunol* 182, 6369-6378 (2009).
Lim et al., Mapping glycans onto specific N-linked glycosylation sites of Pyrus communis PGIP redefines the interface for EPG-PGIP interactions. *J Proteome Res* 8, 673-680 (2009).
Lin et al., COMPASS identifies T-cell subsets correlated with clinical outcomes. *Nat Biotechnol* 33, 610-616 (2015).
Lippolis et al., Analysis of MHC class II antigen processing by quantitation of peptides that constitute nested sets. *J Immunol* 169, 5089-5097 (2002).
Lyerly et al., Human T-cell lymphotropic virus IIIB glycoprotein (gp120) bound to CD4 determinants on normal lymphocytes and expressed by infected cells serves as target for immune attack. *Proc Natl Acad Sci U S A* 84, 4601-4605 (1987).
Mack et al., Common and well-documented HLA alleles: 2012 update to the CWD catalogue. *Tissue Antigens* 81, 194-203 (2013).
Maiers et al., High-resolution HLA alleles and haplotypes in the United States population. *Hum Immunol* 68, 779-788 (2007).
Malaspina et al., Conference report: "Functional Glycomics in HIV Type 1 Vaccine Design" workshop report, Bethesda, Maryland, Apr. 30-May 1, 2012. *AIDS Res Hum Retroviruses* 29, 1407-1417 (2013).
Mascola, HIV/AIDS: allied responses. *Nature* 449, 29-30 (2007).
Mascola et al., Recommendations for the design and use of standard virus panels to assess neutralizing antibody responses elicited by candidate human immunodeficiency virus type 1 vaccines. *J Virol* 79, 10103-10107 (2005).
Mcfarland et al., Ovalbumin(323-339) peptide binds to the major histocompatibility complex class II I-A(d) protein using two functionally distinct registers. *Biochemistry* 38, 16663-16670 (1999).
Mclellan et al., Structure of HIV-1 gp120 V1/V2 domain with broadly neutralizing antibody PG9. *Nature* 480, 336-343 (2011).
Micoli et al., Protein Carriers for Glycoconjugate Vaccines: History, Selection Criteria, Characterization and New Trends. *Molecules* 23, (2018).
Middleton et al., Enzymatic Hydrolysis of Pneumococcal Capsular Polysaccharide Renders the Bacterium Vulnerable to Host Defense. *Infect Immun* 86, (2018).
Middleton et al., T Cell-Mediated Humoral Immune Responses to Type 3 Capsular Polysaccharide of *Streptococcus pneumoniae*. *J Immunol* 199, 598-603 (2017).
Mitsdoerffer et al., Proinflammatory T helper type 17 cells are effective B-cell helpers. *Proc Natl Acad Sci U S A* 107, 14292-14297 (2010).
Montefiori, Measuring HIV neutralization in a luciferase reporter gene assay. *Methods Mol Biol* 485, 395-405 (2009).
Moremen et al., Vertebrate protein glycosylation: diversity, synthesis and function. *Nat Rev Mol Cell Biol* 13, 448-462 (2012).
Neefjes et al., Towards a systems understanding of MHC class I and MHC class II antigen presentation. *Nat Rev Immunol* 11, 823-836 (2011).
Pancera et al., Structure and immune recognition of trimeric prefusion HIV-1 Env. *Nature* 514, 455-461 (2014).
Panina-Bordignon et al., Universally immunogenic T cell epitopes: promiscuous binding to human MHC class II and promiscuous recognition by T cells. *Eur J Immunol* 19, 2237-2242 (1989).
Pejchal et al., A potent and broad neutralizing antibody recognizes and penetrates the HIV glycan shield. *Science* 334, 1097-1103 (2011).
Peng et al., Comprehensive analysis of RNA-Seq data reveals extensive RNA editing in a human transcriptome. *Nat Biotechnol* 30, 253-260 (2012).
Pichichero, Protein carriers of conjugate vaccines: characteristics, development, and clinical trials. *Hum Vaccin Immunother* 9, 2505-2523 (2013).
Pluger et al., Specific role for cathepsin S in the generation of antigenic peptides in vivo. *Eur J Immunol* 32, 467-476 (2002).
Polonskaya et al., T cells control the generation of nanomolar-affinity anti-glycan antibodies. *J Clin Invest* 127, 1491-1504 (2017).
Raju et al., Epitopes for human CD4+ cells on diphtheria toxin: structural features of sequence segments forming epitopes recognized by most subjects. *Eur J Immunol* 25, 3207-3214 (1995).
Rammensee et al., MHC ligands and peptide motifs: first listing. *Immunogenetics* 41, 178-228 (1995).
Rannes et al., Glycoprotein labeling using engineered variants of galactose oxidase obtained by directed evolution. *J Am Chem Soc* 133, 8436-8439 (2011).
Rappuoli et al., On the mechanisms of conjugate vaccines. *Proc Natl Acad Sci U S A* 116, 14-16 (2019).
Reeves and Goebel, Chemoimmunological Studies on the Soluble Specific Substance of Pneumococcus V. The Structure of the Type Iii Polysaccharide, J. Biol. Chem, 139: 511-519 (1941).
Riaz et al., Surface Functionalization and Targeting Strategies of Liposomes in Solid Tumor Therapy: A Review. *Int J Mol Sci* 19, (2018).
Riniker et al., A General Strategy for the Synthesis of Large Peptides: rl~he Combined Solid-Phase and Solution Approach. Tetrahedron 49(41):9307-9320 (1993).
Roberts, Lysosomal cysteine proteases: structure, function and inhibition of cathepsins. *Drug News Perspect* 18, 605-614 (2005).
Rodrigues-Da-Silva et al., Immunogenicity of synthetic peptide constructs based on PvMSP9(E795-A808), a linear B-cell epitope of the P. vivax Merozoite Surface Protein-9. *Vaccine* 37, 306-313 (2019).
Sambrook et al., Molecular cloning: a laboratory manual, 2nd ed. Cold Spring Harbor Laboratory Press: Cold Spring Harbor, New York; 1989. Cover page, title page, and table of contents. 30 pgs.
Sanders et al., A next-generation cleaved, soluble HIV-1 Env trimer, BG505 SOSIP.664 gp140, expresses multiple epitopes for broadly neutralizing but not non-neutralizing antibodies. *PLoS Pathog* 9, e1003618 (2013).
Sanders et al., Native-like Env trimers as a platform for HIV-1 vaccine design. *Immunol Rev* 275, 161-182 (2017).
Schutze et al., Carrier-induced epitopic suppression, a major issue for future synthetic vaccines. *J Immunol* 135, 2319-2322 (1985).
Schutze et al., Epitopic suppression in synthetic vaccine models: analysis of the effector mechanisms. *Cell Immunol* 104, 79-90 (1987).
Scott et al., Crystal structures of two I-Ad-peptide complexes reveal that high affinity can be achieved without large anchor residues. *Immunity* 8, 319-329 (1998).
Sharma et al., Cleavage-independent HIV-1 Env trimers engineered as soluble native spike mimetics for vaccine design. *Cell Rep* 11, 539-550 (2015).

(56) References Cited

OTHER PUBLICATIONS

Shinomiya et al., The role of T cells in immunoglobulin class switching of specific antibody production system in vitro in humans. *Cell Immunol* 118, 239-249 (1989).
Singh et al., HaptenDB: a comprehensive database of haptens, carrier proteins and anti-hapten antibodies. *Bioinformatics* 22, 253-255 (2006).
Sinigaglia et al., A malaria T-cell epitope recognized in association with most mouse and human MHC class II molecules. *Nature* 336, 778-780 (1988).
Sliepen et al., Structure and immunogenicity of a stabilized HIV-1 envelope trimer based on a group-M consensus sequence. *Nat Commun* 10, 2355 (2019).
Slingluff, The present and future of peptide vaccines for cancer: single or multiple, long or short, alone or in combination? *Cancer J* 17, 343-350 (2011).
Snook et al., Preclinical Evaluation of a Replication-Deficient Recombinant Adenovirus Serotype 5 Vaccine Expressing Guanylate Cyclase C and the PADRE T-helper Epitope. *Hum Gene Ther Methods* 27, 238-250 (2016).
Southwood et al., Several common HLA-DR types share largely overlapping peptide binding repertoires. *J Immunol* 160, 3363-3373 (1998).
Stalnaker et al., Glycomic analyses of mouse models of congenital muscular dystrophy. *J Biol Chem* 286, 21180-21190 (2011).
Steede et al., Shaping T cell—B cell collaboration in the response to human immunodeficiency virus type 1 envelope glycoprotein gp120 by peptide priming. *PLoS One* 8, e65748 (2013).
Stewart-Jones et al., Trimeric HIV-1-Env Structures Define Glycan Shields from Clades A, B, and G. *Cell* 165, 813-826 (2016).
Streeck et al., Harnessing CD4(+) T cell responses in HIV vaccine development. *Nat Med* 19, 143-149 (2013).
Sun et al., Metabolic labeling of HIV-1 envelope glycoprotein gp 120 to elucidate the effect of gp120 glycosylation on antigen uptake. *J Biol Chem 293*, 15178-15194 (2018).
Sun et al., Carbohydrates as T-cell antigens with implications in health and disease. *Glycobiology* 26, 1029-1040 (2016).
Sun et al., Polysaccharide structure dictates mechanism of adaptive immune response to glycoconjugate vaccines. *Proc Natl Acad Sci U S A* 116, 193-198 (2019).
Surman et al., Localization of CD4+ T cell epitope hotspots to exposed strands of HIV envelope glycoprotein suggests structural influences on antigen processing. *Proc Natl Acad Sci U S A* 98, 4587-4592 (2001).
Tatusova et al., BLAST 2 Sequences, a new tool for comparing protein and nucleotide sequences. *FEMS Microbiol Lett* 174, 247-250 (1999).
Teo et al., Glycopeptide-specific monoclonal antibodies suggest new roles for O-GlcNAc. *Nat Chem Biol* 6, 338-343 (2010).
Tonomura et al., Antigen-specific human T-cell responses and T cell-dependent production of human antibodies in a humanized mouse model. *Blood* 111, 4293-4296 (2008).
Tran et al., Cancer immunotherapy based on mutation-specific CD4+ T cells in a patient with epithelial cancer. *Science* 344, 641-645 (2014).
Van Lith et al., HLA-DP, HLA-DQ, and HLA-DR have different requirements for invariant chain and HLA-DM. *J Biol Chem* 285, 40800-40808 (2010).
Van Montfort et al., HIV-1 N-glycan composition governs a balance between dendritic cell-mediated viral transmission and antigen presentation. *J Immunol* 187, 4676-4685 (2011).
Van Rompay, The use of nonhuman primate models of HIV infection for the evaluation of antiviral strategies. *AIDS Res Hum Retroviruses* 28, 16-35 (2012).
Velazquez et al., Quantitation of lysozyme peptides bound to class II MHC molecules indicates very large differences in levels of presentation. *J Immunol* 166, 5488-5494 (2001).
Wang, Synthetic carbohydrate antigens for HIV vaccine design. *Curr Opin Chem Biol* 17, 997-1005 (2013).
Wantuch et al., Current status and future directions of invasive pneumococcal diseases and prophylactic approaches to control them. *Hum Vaccin Immunother* 14, 2303-2309 (2018).
Wantuch et al., Invasive pneumococcal disease in relation to vaccine type serotypes. *Hum Vaccin Immunother* 15, 874-875 (2019).
Watanabe et al., Hematopoietic stem cell-engrafted NOD/SCID/IL2Rgamma null mice develop human lymphoid systems and induce long-lasting HIV-1 infection with specific humoral immune responses. *Blood* 109, 212-218 (2007).
Xu et al., Epitope-based vaccine design yields fusion peptide-directed antibodies that neutralize diverse strains of HIV-1. *Nat Med* 24, 857-867 (2018).
Yoshida-Moriguchi et al., O-mannosyl phosphorylation of alpha-dystroglycan is required for laminin binding. *Science* 327, 88-92 (2010).
Yu et al., Exploiting glycan topography for computational design of Env glycoprotein antigenicity. *PLoS Comput Biol* 14, e1006093 (2018).
Zeigler et al., Optimization of a multivalent peptide vaccine for nicotine addiction. *Vaccine* 37, 1584-1590 (2019).
Zhu et al., Characterizing O-linked glycopeptides by electron transfer dissociation: fragmentation rules and applications in data analysis. *Anal Chem* 85, 8403-8411 (2013).

* cited by examiner

FIG. 1

SEQ ID NO:1

MPITINNFRYSDPVNNDTIIMMEPPYCKGLDIYYKAFKITDRIWIVPERYEFGTKPEDFN
PPSSLIEGASEYYDPNYLRTDSDKDRFLQTMVKLFNRIKNNVAGEALLDKIINAIPYLGN
SYSLLDKFDTNSNSVSFNLLEQDPSGATTKSAMLTNLIIFGPGPVLNKNEVRGIVLRVDN
KNYFPCRDGFGSIMQMAFCPEYVPTFDNVIENITSLTIGKSKYFQDPALLLMHELIHVLH
GLYGMQVSSHEIIPSKQEIYMQHTYPISAEELFTFGGQDANLISIDIKNDLYEKTLNDYK
AIANKLSQVTSCNDPNIDIDSYKQIYQQKYQFDKDSNGQYIVNEDKFQILYNSIMYGFTE
IELGKKFNIKTRLSYFSMNHDPVKIPNLLDDTIYNDTEGFNIESKDLKSEYKGQNMRVNT
NAFRNVDGSGLVSKLIGLCKKIIPPTNIRENLYNRTASLTDLGGELCIKIKNEDLTFIAE
KNSFSEEPFQDEIVSYNTKNKPLNFNYSLDKIIVDYNLQSKITLPNDRTTPVTKGIPYAP
EYKSNAASTIEIHNIDDNTIYQYLYAQKSPTTLQRITMTNSVDDALINSTKIYSYFPSVI
SKVNQGAQGILFLQWVRDIIDDFTNESSQKTTIDKISDVSTIVPYIGPALNIVKQGYEGN
FIGALETTGVVLLLEYIPEITLPVIAALSIAESSTQKEKIIKTIDNFLEKRYEKWIEVYK
LVKAKWLGTVNTQFQKRSYQMYRSLEYQVDAIKKIIDYEYKIYSGPDKEQIADEINNLKN
KLEEKANKAMININIFMRESSRSFLVNQMINEAKKQLLEFDTQSKNILMQYIKANSKFIG
ITELKKLESKINKVFSTPIPFSYSKNLDCWVDNEEDIDVILKKSTILNLDINNDIISDIS
GFNSSVITYPDAQLVPGINGKAIHLVNNESSEVIVHKAMDIEYNDMFNNFTVSFWLRVPK
VSASHLEQYGTNEYSIISSMKKHSLSIGSGWSVSLKGNNLIWTLKDSAGEVRQITFRDLP
DKFNAYLANKWVFITITNDRLSSANLYINGVLMGSAEITGLGAIREDNNITLKLDRCNNN
NQYVSIDKFRIFCKALNPKEIEKLYTSYLSITFLRDFWGNPLRYDTEYYLIPVASSSKDV
QLKNITDYMYLTNAPSYTNGKLNIYYRRLYNGLKFIIKRYTPNNEIDSFVKSGDFIKLYV
SYNNNEHIVGYPKDGNAFNNLDRILRVGYNAPGIPLYKKMEAVKLRDLKTYSVQLKLYDD
KNASLGLVGTHNGQIGNDPNRDILIASNWYFNHLKDKILGCDWYFVPTDEGWTND

SEQ ID NO:2

GADDVVDSSKSFVMENFSSYHGTKPGYVDSIQKGIQKPKSGTQGNYDDDWKEFYSTDNKYDAAGYSVDNENPLSGKA
GGVVKVTYPGLTKVLALKVDNAETIKKELGLSLTEPLMEQVGTEEFIKRFGDGASRVVLSLPFAEGSSSVEYINNWE
QAKALSVELEINFETRGKRGQDAMYEYMAQACAGNRVRRSVGSSLSCINLDWDVIRDKTKTKIESLKEHGPIKNKMS
ESPNKTVSEEKAKQYLEEFHQTALEHPELSELKTVTGTNPVFAGANYAAWAVNVAQVIDSETADNLEKTTAALSILP
GIGSVMGIADGAVHHNTEEIVAQSIALSSLMVAQAIPLVGELVDIGFAAYNFVESIINLFQVVHNSYNRPAYSPGHK
TQPFLHDGYAVSWNTVEDSIIRTGFQGESGHDIKITAENTPLPIAGVLLPTIPGKLDVNKSKTHISVNGRKIRMRCR
AIDGDVTFCRPKSPVYVGNGVHANLHVAFHRSSSEKIHSNEISSDSIGVLGYQKTVDHTKVNSKLSLFFEIKS

SEQUENCE LISTING

```
<160> NUMBER OF SEQ ID NOS: 42

<210> SEQ ID NO 1
<211> LENGTH: 1315
<212> TYPE: PRT
<213> ORGANISM: Clostridium tetani

<400> SEQUENCE: 1

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140
```

-continued

```
Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
```

```
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990
```

```
Val Ser Leu Lys Gly Asn Asn Leu  Ile Trp Thr Leu Lys  Asp Ser Ala
        995                1000                1005

Gly Glu  Val Arg Gln Ile Thr  Phe Arg Asp Leu Pro  Asp Lys Phe
    1010                1015                1020

Asn Ala  Tyr Leu Ala Asn Lys  Trp Val Phe Ile Thr  Ile Thr Asn
    1025                1030                1035

Asp Arg  Leu Ser Ser Ala Asn  Leu Tyr Ile Asn Gly  Val Leu Met
    1040                1045                1050

Gly Ser  Ala Glu Ile Thr Gly  Leu Gly Ala Ile Arg  Glu Asp Asn
    1055                1060                1065

Asn Ile  Thr Leu Lys Leu Asp  Arg Cys Asn Asn Asn  Asn Gln Tyr
    1070                1075                1080

Val Ser  Ile Asp Lys Phe Arg  Ile Phe Cys Lys Ala  Leu Asn Pro
    1085                1090                1095

Lys Glu  Ile Glu Lys Leu Tyr  Thr Ser Tyr Leu Ser  Ile Thr Phe
    1100                1105                1110

Leu Arg  Asp Phe Trp Gly Asn  Pro Leu Arg Tyr Asp  Thr Glu Tyr
    1115                1120                1125

Tyr Leu  Ile Pro Val Ala Ser  Ser Ser Lys Asp Val  Gln Leu Lys
    1130                1135                1140

Asn Ile  Thr Asp Tyr Met Tyr  Leu Thr Asn Ala Pro  Ser Tyr Thr
    1145                1150                1155

Asn Gly  Lys Leu Asn Ile Tyr  Tyr Arg Arg Leu Tyr  Asn Gly Leu
    1160                1165                1170

Lys Phe  Ile Ile Lys Arg Tyr  Thr Pro Asn Asn Glu  Ile Asp Ser
    1175                1180                1185

Phe Val  Lys Ser Gly Asp Phe  Ile Lys Leu Tyr Val  Ser Tyr Asn
    1190                1195                1200

Asn Asn  Glu His Ile Val Gly  Tyr Pro Lys Asp Gly  Asn Ala Phe
    1205                1210                1215

Asn Asn  Leu Asp Arg Ile Leu  Arg Val Gly Tyr Asn  Ala Pro Gly
    1220                1225                1230

Ile Pro  Leu Tyr Lys Lys Met  Glu Ala Val Lys Leu  Arg Asp Leu
    1235                1240                1245

Lys Thr  Tyr Ser Val Gln Leu  Lys Leu Tyr Asp Asp  Lys Asn Ala
    1250                1255                1260

Ser Leu  Gly Leu Val Gly Thr  His Asn Gly Gln Ile  Gly Asn Asp
    1265                1270                1275

Pro Asn  Arg Asp Ile Leu Ile  Ala Ser Asn Trp Tyr  Phe Asn His
    1280                1285                1290

Leu Lys  Asp Lys Ile Leu Gly  Cys Asp Trp Tyr Phe  Val Pro Thr
    1295                1300                1305

Asp Glu  Gly Trp Thr Asn Asp
    1310                1315


<210> SEQ ID NO 2
<211> LENGTH: 535
<212> TYPE: PRT
<213> ORGANISM: Corynebacterium diphtheriae

<400> SEQUENCE: 2

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
```

-continued

```
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445
```

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 3
<211> LENGTH: 14
<212> TYPE: PRT
<213> ORGANISM: Artificial Sequence
<220> FEATURE:
<223> OTHER INFORMATION: TT-derived peptide

<400> SEQUENCE: 3

Leu Phe Asn Arg Ile Lys Asn Asn Val Ala Gly Glu Ala Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: TT-derived peptide

<400> SEQUENCE: 4

Asn Phe Ile Gly Ala Leu Glu Thr
1               5

<210> SEQ ID NO 5
<211> LENGTH: 12
<212> TYPE: PRT
<213> ORGANISM: Artificial Sequence
<220> FEATURE:
<223> OTHER INFORMATION: TT-derived peptide

<400> SEQUENCE: 5

Asn Ile Leu Met Gln Tyr Ile Lys Ala Asn Ser Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: TT-derived peptide

<400> SEQUENCE: 6

Cys Lys Ala Leu Asn Pro Lys Glu Ile Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: TT-derived peptide

<400> SEQUENCE: 7

Leu Tyr Asn Gly Leu Lys Phe Ile Ile Lys Arg
1 5 10

<210> SEQ ID NO 8
<211> LENGTH: 15
<212> TYPE: PRT
<213> ORGANISM: Artificial Sequence
<220> FEATURE:
<223> OTHER INFORMATION: TT-derived peptide

<400> SEQUENCE: 8

Asp Arg Ile Leu Arg Val Gly Tyr Asn Ala Pro Gly Ile Pro Leu
1 5 10 15

<210> SEQ ID NO 9
<211> LENGTH: 12
<212> TYPE: PRT
<213> ORGANISM: Artificial Sequence
<220> FEATURE:
<223> OTHER INFORMATION: TT-derived peptide

<400> SEQUENCE: 9

Gly Tyr Asn Ala Pro Gly Ile Pro Leu Tyr Lys Lys
1 5 10

<210> SEQ ID NO 10
<211> LENGTH: 14
<212> TYPE: PRT
<213> ORGANISM: Artificial Sequence
<220> FEATURE:
<223> OTHER INFORMATION: CRM-derived peptide

<400> SEQUENCE: 10

Gly Tyr Val Asp Ser Ile Gln Lys Gly Ile Gln Lys Pro Lys
1 5 10

<210> SEQ ID NO 11
<211> LENGTH: 11
<212> TYPE: PRT
<213> ORGANISM: Artificial Sequence
<220> FEATURE:
<223> OTHER INFORMATION: CRM-derived peptide

<400> SEQUENCE: 11

Gly Leu Thr Lys Val Leu Ala Leu Lys Val Asp
1 5 10

<210> SEQ ID NO 12
<211> LENGTH: 14
<212> TYPE: PRT
<213> ORGANISM: Artificial Sequence
<220> FEATURE:
<223> OTHER INFORMATION: CRM-derived peptide

<400> SEQUENCE: 12

Lys Thr Thr Ala Ala Leu Ser Ile Leu Pro Gly Ile Gly Ser
1 5 10

<210> SEQ ID NO 13
<211> LENGTH: 16
<212> TYPE: PRT
<213> ORGANISM: Artificial Sequence
<220> FEATURE:
<223> OTHER INFORMATION: CRM-derived peptide

<400> SEQUENCE: 13

Thr Pro Leu Pro Ile Ala Gly Val Leu Leu Pro Thr Ile Pro Gly Lys
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: TT-derived peptide

<400> SEQUENCE: 14

Gln Tyr Ile Lys Ala Asn Ser Lys Phe Ile Gly Ile Thr Glu Leu
1 5 10 15

<210> SEQ ID NO 15
<211> LENGTH: 12
<212> TYPE: PRT
<213> ORGANISM: Artificial Sequence
<220> FEATURE:
<223> OTHER INFORMATION: TT-derived peptide

<400> SEQUENCE: 15

Gly Gln Ile Gly Asn Asp Pro Asn Arg Asp Ile Leu
1 5 10

<210> SEQ ID NO 16
<211> LENGTH: 16
<212> TYPE: PRT
<213> ORGANISM: Artificial Sequence
<220> FEATURE:
<223> OTHER INFORMATION: TT-derived peptide

<400> SEQUENCE: 16

Val Ser Ile Asp Lys Phe Arg Ile Phe Cys Lys Ala Leu Asn Pro Lys
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: TT-derived peptide

<400> SEQUENCE: 17

Tyr Asp Thr Glu Tyr Tyr Leu Ile Pro Val Ala Ser Ser Ser Lys Asp
1 5 10 15

<210> SEQ ID NO 18
<211> LENGTH: 21
<212> TYPE: PRT
<213> ORGANISM: Artificial Sequence
<220> FEATURE:
<223> OTHER INFORMATION: TT-derived peptide

<400> SEQUENCE: 18

Phe Asn Asn Phe Thr Val Ser Phe Trp Leu Arg Val Pro Lys Val Ser
1 5 10 15

Ala Ser His Leu Glu
20

<210> SEQ ID NO 19
<211> LENGTH: 16
<212> TYPE: PRT
<213> ORGANISM: Artificial Sequence
<220> FEATURE:
<223> OTHER INFORMATION: TT-derived peptide

<400> SEQUENCE: 19

Lys Phe Ile Ile Lys Arg Tyr Thr Pro Asn Asn Glu Ile Asp Ser Phe
1               5                   10                  15

<210> SEQ ID NO 20
<211> LENGTH: 27
<212> TYPE: PRT
<213> ORGANISM: Artificial Sequence
<220> FEATURE:
<223> OTHER INFORMATION: TT-derived peptide

<400> SEQUENCE: 20

Tyr Asp Pro Asn Tyr Leu Arg Thr Asp Ser Asp Lys Asp Arg Phe Leu
1               5                   10                  15

Gln Thr Met Val Lys Leu Phe Asn Arg Ile Lys
            20                  25

<210> SEQ ID NO 21
<211> LENGTH: 20
<212> TYPE: PRT
<213> ORGANISM: Artificial Sequence
<220> FEATURE:
<223> OTHER INFORMATION: TT-derived peptide

<400> SEQUENCE: 21

Ile Asp Lys Ile Ser Asp Val Ser Thr Ile Val Pro Tyr Ile Gly Pro
1               5                   10                  15

Ala Leu Asn Ile
            20

<210> SEQ ID NO 22
<211> LENGTH: 21
<212> TYPE: PRT
<213> ORGANISM: Artificial Sequence
<220> FEATURE:
<223> OTHER INFORMATION: TT-derived peptide

<400> SEQUENCE: 22

Asn Asn Phe Thr Val Ser Phe Trp Leu Arg Val Pro Lys Val Ser Ala
1               5                   10                  15

Ser His Leu Glu Thr
            20

<210> SEQ ID NO 23
<211> LENGTH: 19
<212> TYPE: PRT
<213> ORGANISM: Artificial Sequence
<220> FEATURE:
<223> OTHER INFORMATION: CRM-derived peptide

<400> SEQUENCE: 23

Pro Val Phe Ala Gly Ala Asn Tyr Ala Ala Trp Ala Val Asn Val Ala
1               5                   10                  15

Gln Val Ile

<210> SEQ ID NO 24
<211> LENGTH: 20
<212> TYPE: PRT
<213> ORGANISM: Artificial Sequence
<220> FEATURE:
<223> OTHER INFORMATION: CRM-derived peptide

<400> SEQUENCE: 24

Val His His Asn Thr Glu Glu Ile Val Ala Gln Ser Ile Ala Leu Ser
1 5 10 15

Ser Leu Met Val
20

<210> SEQ ID NO 25
<211> LENGTH: 20
<212> TYPE: PRT
<213> ORGANISM: Artificial Sequence
<220> FEATURE:
<223> OTHER INFORMATION: CRM-derived peptide

<400> SEQUENCE: 25

Gln Ser Ile Ala Leu Ser Ser Leu Met Val Ala Gln Ala Ile Pro Leu
1 5 10 15

Val Gly Glu Leu
20

<210> SEQ ID NO 26
<211> LENGTH: 20
<212> TYPE: PRT
<213> ORGANISM: Artificial Sequence
<220> FEATURE:
<223> OTHER INFORMATION: CRM-derived peptide

<400> SEQUENCE: 26

Val Asp Ile Gly Phe Ala Ala Tyr Asn Phe Val Glu Ser Ile Ile Asn
1 5 10 15

Leu Phe Gln Val
20

<210> SEQ ID NO 27
<211> LENGTH: 20
<212> TYPE: PRT
<213> ORGANISM: Artificial Sequence
<220> FEATURE:
<223> OTHER INFORMATION: CRM-derived peptide

<400> SEQUENCE: 27

Gln Gly Glu Ser Gly His Asp Ile Lys Ile Thr Ala Glu Asn Thr Pro
1 5 10 15

Leu Pro Ile Ala
20

<210> SEQ ID NO 28
<211> LENGTH: 20
<212> TYPE: PRT
<213> ORGANISM: Artificial Sequence
<220> FEATURE:
<223> OTHER INFORMATION: CRM-derived peptide

<400> SEQUENCE: 28

Gly Val Leu Leu Pro Thr Ile Pro Gly Lys Leu Asp Val Asn Lys Ser
1 5 10 15

Lys Thr His Ile
20

<210> SEQ ID NO 29
<211> LENGTH: 27
<212> TYPE: PRT
<213> ORGANISM: Artificial Sequence
<220> FEATURE:
<223> OTHER INFORMATION: CRM-derived peptide

<400> SEQUENCE: 29

```
Ala Tyr Asn Phe Val Glu Ser Ile Ile Asn Leu Phe Gln Val Val His
1               5                   10                  15

Asn Ser Tyr Asn Arg Pro Ala Tyr Ser Pro Gly
            20                  25


<210> SEQ ID NO 30
<211> LENGTH: 16
<212> TYPE: PRT
<213> ORGANISM: Artificial Sequence
<220> FEATURE:
<223> OTHER INFORMATION: CRM-derived peptide

<400> SEQUENCE: 30

Pro Gly Lys Leu Asp Val Asn Lys Ser Lys Thr His Ile Ser Val Asn
1               5                   10                  15


<210> SEQ ID NO 31
<211> LENGTH: 16
<212> TYPE: PRT
<213> ORGANISM: Artificial Sequence
<220> FEATURE:
<223> OTHER INFORMATION: CRM-derived peptide

<400> SEQUENCE: 31

Asp Val Asn Lys Ser Lys Thr His Ile Ser Val Asn Gly Arg Lys Ile
1               5                   10                  15


<210> SEQ ID NO 32
<211> LENGTH: 29
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (15)..(15)
<223> OTHER INFORMATION: Xaa can be any naturally occurring amino acid

<400> SEQUENCE: 32

Lys Thr Thr Ala Ala Leu Ser Ile Leu Pro Gly Ile Gly Ser Xaa Lys
1               5                   10                  15

Thr Thr Ala Ala Leu Ser Ile Leu Pro Gly Ile Gly Ser
            20                  25


<210> SEQ ID NO 33
<211> LENGTH: 33
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (1)..(1)
<223> OTHER INFORMATION: cysteine
<220> FEATURE:
<221> NAME/KEY: misc_feature
<222> LOCATION: (16)..(16)
<223> OTHER INFORMATION: valine
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: cysteine
<220> FEATURE:
<221> NAME/KEY: misc_feature
<222> LOCATION: (33)..(33)
```

<223> OTHER INFORMATION: valine

<400> SEQUENCE: 33

Xaa Lys Thr Thr Ala Ala Leu Ser Ile Leu Pro Gly Ile Gly Ser Xaa
1               5                   10                  15

Xaa Xaa Lys Thr Thr Ala Ala Leu Ser Ile Leu Pro Gly Ile Gly Ser
            20                  25                  30

Xaa

<210> SEQ ID NO 34
<211> LENGTH: 30
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (15)..(15)
<223> OTHER INFORMATION: Xaa can be any naturally occurring amino acid

<400> SEQUENCE: 34

Lys Thr Thr Ala Ala Leu Ser Ile Leu Pro Gly Ile Gly Ser Xaa Lys
1               5                   10                  15

Thr Thr Ala Ala Leu Ser Ile Leu Pro Gly Ile Gly Ser Val
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (16)..(16)
<223> OTHER INFORMATION: Xaa can be any naturally occurring amino acid

<400> SEQUENCE: 35

Cys Lys Thr Thr Ala Ala Leu Ser Ile Leu Pro Gly Ile Gly Ser Xaa
1               5                   10                  15

Cys Lys Thr Thr Ala Ala Leu Ser Ile Leu Pro Gly Ile Gly Ser Val
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (15)..(15)
<223> OTHER INFORMATION: Xaa can be any naturally occurring amino acid

<400> SEQUENCE: 36

Lys Thr Thr Ala Ala Leu Ser Ile Leu Pro Gly Ile Gly Ser Xaa Lys
1               5                   10                  15

Thr Thr Ala Ala Leu Ser Ile Leu Pro Gly Pro Ile Gly Ser Val
            20                  25                  30

<210> SEQ ID NO 37
<211> LENGTH: 21
<212> TYPE: PRT
<213> ORGANISM: Artificial Sequence
<220> FEATURE:
<223> OTHER INFORMATION: TT-derived peptide
<220> FEATURE:
<221> NAME/KEY: misc_feature
<222> LOCATION: (11)..(11)
<223> OTHER INFORMATION: Xaa can be any naturally occurring amino acid

<400> SEQUENCE: 37

Cys Lys Ala Leu Asn Pro Lys Glu Ile Glu Xaa Cys Lys Ala Leu Asn
1 5 10 15

Pro Lys Glu Ile Glu
20

<210> SEQ ID NO 38
<211> LENGTH: 21
<212> TYPE: PRT
<213> ORGANISM: Artificial Sequence
<220> FEATURE:
<223> OTHER INFORMATION: Multimer
<220> FEATURE:
<221> NAME/KEY: misc_feature
<222> LOCATION: (11)..(11)
<223> OTHER INFORMATION: Xaa can be any naturally occurring amino acid

<400> SEQUENCE: 38

Cys Lys Ala Leu Asn Pro Lys Glu Ile Glu Xaa Cys Lys Ala Leu Asn
1 5 10 15

Pro Lys Glu Ile Glu
20

<210> SEQ ID NO 39
<211> LENGTH: 25
<212> TYPE: PRT
<213> ORGANISM: Artificial Sequence
<220> FEATURE:
<223> OTHER INFORMATION: CRM-derived peptide
<220> FEATURE:
<221> NAME/KEY: misc_feature
<222> LOCATION: (1)..(1)
<223> OTHER INFORMATION: cysteine
<220> FEATURE:
<221> NAME/KEY: misc_feature
<222> LOCATION: (13)..(13)
<223> OTHER INFORMATION: valine
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: valine

<400> SEQUENCE: 39

Xaa Leu Tyr Asn Gly Leu Lys Phe Ile Ile Lys Arg Xaa Xaa Cys Lys
1 5 10 15

Ala Leu Asn Pro Lys Glu Ile Glu Xaa
20 25

<210> SEQ ID NO 40
<211> LENGTH: 23
<212> TYPE: PRT
<213> ORGANISM: Artificial Sequence
<220> FEATURE:
<223> OTHER INFORMATION: TT-derived peptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 40

-continued

```
Cys Leu Tyr Asn Gly Leu Lys Phe Ile Ile Lys Arg Xaa Cys Lys Ala
1               5                   10                  15

Leu Asn Pro Lys Glu Ile Glu
            20


<210> SEQ ID NO 41
<211> LENGTH: 17
<212> TYPE: PRT
<213> ORGANISM: Artificial Sequence
<220> FEATURE:
<223> OTHER INFORMATION: TT-derived peptide

<400> SEQUENCE: 41

Thr Val Ser Phe Trp Leu Arg Val Pro Lys Val Ser Ala Ser His Leu
1               5                   10                  15

Glu


<210> SEQ ID NO 42
<211> LENGTH: 4
<212> TYPE: PRT
<213> ORGANISM: Artificial Sequence
<220> FEATURE:
<223> OTHER INFORMATION: Peptide

<400> SEQUENCE: 42

Gly Phe Leu Gly
1
```

TETANUS TOXOID AND CRM-BASED PEPTIDES AND METHODS OF USE

CROSS-REFERENCE TO RELATED APPLICATIONS

This application is a § 371 National Stage application of PCT/US2020/061699, which claims the benefit of U.S. Provisional Application Ser. No. 62/939,299, filed Nov. 22, 2019, which is incorporated by reference herein in its entirety.

SEQUENCE LISTING

This application contains a Sequence Listing electronically submitted via EFS-Web to the United States Patent and Trademark Office as an ASCII text file entitled "0235.000289US01_ST25.txt" having a size of 27 kilobytes and created on Feb. 22, 2021. The information contained in the Sequence Listing is incorporated by reference herein.

GOVERNMENT FUNDING

This invention was made with government support under R01 AI123383, GM061126, and K01 OD026569, awarded by the National Institutes of Health. The government has certain rights in the invention.

BACKGROUND

The ability to cause immune responses to specific antigens is fundamental to treating and preventing infectious diseases. Many potentially useful antigens do not elicit an immune response when administered, or the immune response to the antigen is weak. One method for overcoming this is to attach or conjugate a weakly immunogenic antigen to a carrier protein, where the presence of the carrier protein significantly increases the immunogenicity. Two carrier proteins often used increase the immunogenicity of capsular polysaccharides are $CRM_{197}$ and tetanus toxoid (TT). Researchers have identified synthetic short fragments of $CRM_{197}$ and TT that can be used as carrier proteins instead of the full length $CRM_{197}$ and TT.

SUMMARY OF THE APPLICATION

As described herein, the inventors have identified short fragments of $CRM_{197}$ and TT that are naturally processed and presented by human B cells and able to stimulate CD4+ T cells. These fragments elicit T cell responses that are more significant than previously characterized synthetic short fragments of $CRM_{197}$ and TT.

Accordingly, provided herein are isolated peptides and multimers of isolated peptides. Also provided are compositions that include the isolated peptide or the multimer. Further provided are methods, including (i) methods for increasing the antigenicity of a compound, such as an antigen, and (ii) methods for inducing an immune response in a subject The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided. The term "consisting of" means including, and limited to, whatever follows the phrase "consisting of." That is, "consisting of" indicates that the listed elements are required or mandatory, and that no other elements may be present. The term "consisting essentially of" indicates that any elements listed after the phrase are included, and that other elements than those listed may be included provided that those elements do not interfere with or contribute to the activity or action specified in the disclosure for the listed elements.

Unless otherwise specified, "a," "an," "the," and "at least one" are used interchangeably and mean one or more than one.

Conditions that are "suitable" for an event to occur, such as proliferation of a T cell, or "suitable" conditions are conditions that do not prevent such events from occurring. Thus, these conditions permit, enhance, facilitate, and/or are conducive to the event.

As used herein, "providing" in the context of, for instance, a protein or a composition, means making the protein or composition, purchasing the protein or composition, or otherwise obtaining the protein or composition.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

Terms used herein will be understood to take on their ordinary meaning in the relevant art unless specified otherwise. Several terms used herein and their meanings are set forth below.

BRIEF DESCRIPTION OF THE FIGURES

The following detailed description of illustrative embodiments of the present disclosure may be best understood when read in conjunction with the following drawings.

FIG. 1 shows exemplary amino acid sequences discussed in the present disclosure.

FIG. 5C) PBMCs were enriched for CD4+ T cells and APCs. APCs were treated with mitomycin-C or fixed with paraformaldehyde then incubated with respective antigen supplemented with IL-2. Proliferation was measured by gating CD4+ T cells and measuring percent of CFSE− in CD4+ populations. Student's t test was performed for statistical value with $p<0.05$ for all assays.

FIG. 10A shows the enzymatic activity of a wild-type galactose oxidase on polysaccharide from *S. pneumoniae* Type 14, and FIG. 10B shows the enzymatic activity of the mutant galactose oxidase on polysaccharide from *S. pneumoniae* Type 3 and Type 4.

DETAILED DESCRIPTION

Peptides

Figure 2:
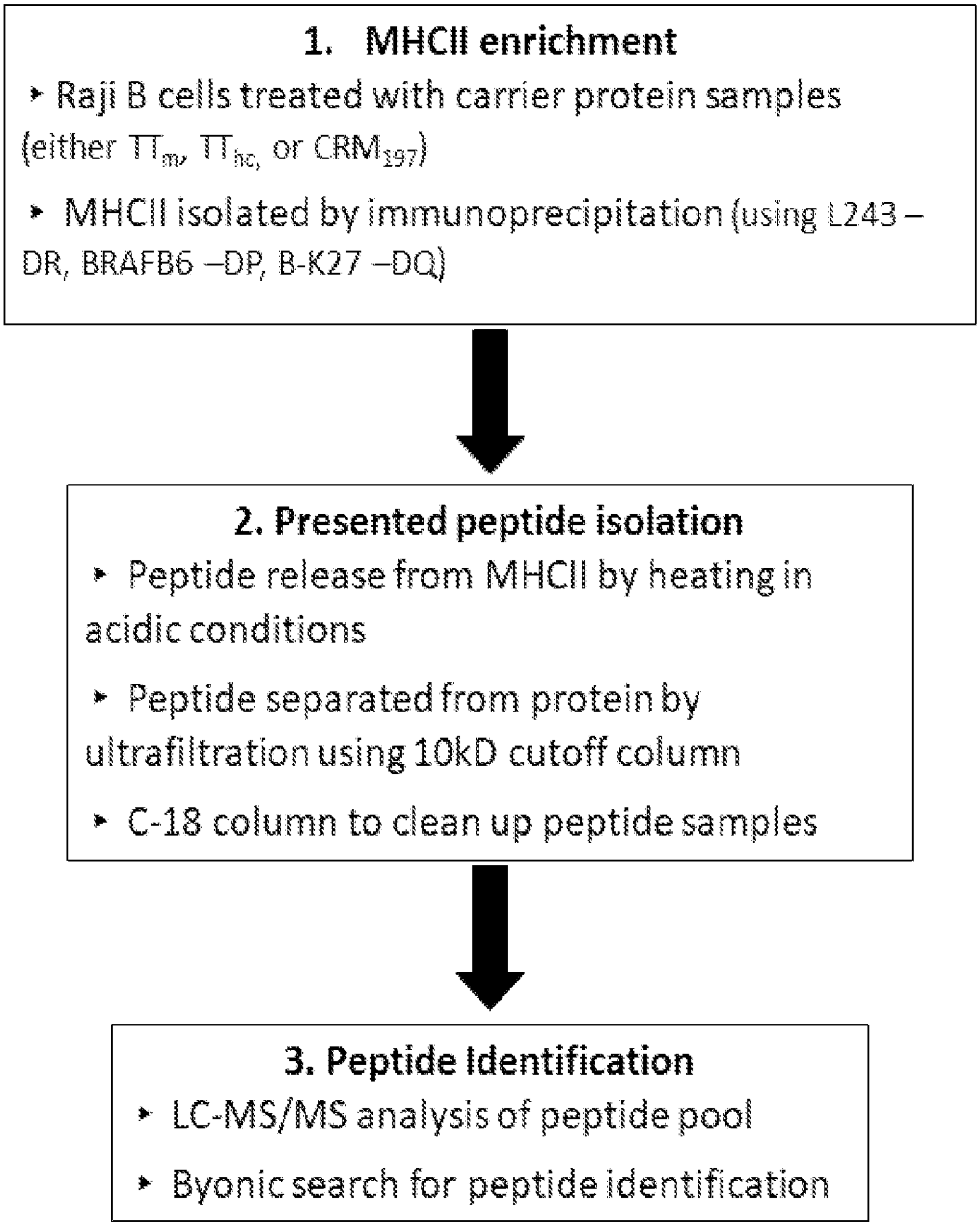
FIG. 2 shows a schematic representation of experimental design to identify peptides presented on differing isotypes of MHCII molecules on human B cells after treatment with common carrier proteins used in vaccine design ($CRM_{197}$ and tetanus toxoid [TT]). Diagram shows steps from cell treatment through peptide identification.

The present disclosure provides isolated peptides. As used herein, the term "peptide" refers broadly to a polymer of two or more amino acids joined together by peptide bonds. The term "peptide" also includes molecules which contain more than one protein joined by a disulfide bond, or complexes of proteins that are joined together, covalently or noncovalently, as multimers (e.g., dimers, tetramers). As described herein, a peptide of the present disclosure can be used to increase the immunogenicity of a molecule (a reduced immunogenicity antigen, or RIA) by attaching the peptide and molecule. A peptide that is joined to a RIA is often referred to as a carrier, thus, the terms oligopeptide, protein, polypeptide, and carrier are all included within the definition of peptide and these terms are used interchangeably.

In one embodiment, a peptide includes consecutive amino acids selected from a tetanus toxoid (TT) protein. An example of a TT protein is available at Genbank accession number WP_011100836.1. A peptide having consecutive amino acids selected from a TT protein is referred to herein as a TT-derived peptide. In one embodiment, a peptide includes consecutive amino acids selected from a diphtheria toxin (CRM) protein. An example of a CRM protein is available at Genbank accession number WP_003850266.1 modified to not include the signal peptide (amino acids 1-25) and modified to include substitution of the amino acid at position 77 in the full length protein from glycine to glutamic acid (SEQ ID NO: 2). A peptide having consecutive amino acids selected from a CRM protein is referred to herein as a CRM-derived peptide.

A TT-derived peptide and a CRM-derived peptide can include at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 consecutive amino acids selected from a TT protein or a CRM protein, such as SEQ ID NO: 1 or SEQ ID NO:2, respectively. A TT-derived peptide and a CRM-derived peptide can include no greater than 30, no greater than 29, no greater than 28, no greater than 27, no greater than 26, no greater than 25, no greater than 24, no greater than 23, no greater than 22, no greater than 21, no greater than 20, no greater than 19, no greater than 18, no greater than 17, no greater than 16, no greater than 15, no greater than 14, no greater than 13, no greater than 12, no greater than 11, no greater than 10, or no greater than 9 consecutive amino acids selected from a TT protein or a CRM protein, such as SEQ ID NO: 1 or SEQ ID NO:2, respectively. In one embodiment, a TT-derived peptide or a CRM-derived peptide can be at least 8 to no greater than 30 amino acids in length, or any combination of lower and upper range selected from the numbers listed above.

Specific examples of TT-derived peptides include LFNRIKNNVAGEAL (SEQ ID NO:3; amino acids 94-107 of SEQ ID NO:1), NFIGALET (SEQ ID NO:4; amino acids 660-667 of SEQ ID NO:1), NILMQYIKANSK (SEQ ID NO:5; amino acids 826-837 of SEQ ID NO: 1), CKALNPKEIE (SEQ ID NO:6; amino acids 1093-1102 of SEQ ID NO:1), LYNGLKFIIKR (SEQ ID NO:7; amino acids 1169-1179 of SEQ ID NO:1), DRILRVGYNAPGIPL (SEQ ID NO:8; amino acids 1222-1236 of SEQ ID NO:1), and GYNAPGIPLYKK (SEQ ID NO:9; amino acids 1228-1239 of SEQ ID NO:1).

In some embodiments, a TT-derived peptide does not include QYIKANSKFIGITEL (SEQ ID NO: 14; amino acids 830-844 of SEQ ID NO:1), GQIGNDPNRDIL (SEQ ID NO:15; amino acids 1273-1284 of SEQ ID NO:1), VSIDKFRIFCKALNPK (SEQ ID NO:16; amino acids 1084-1099 of SEQ ID NO:1), YDTEYYLIPVASSSKD (SEQ ID NO:17; amino acids 1124-1139 of SEQ ID NO:1), FNNFTVSFWLRVPKVSASHLE (SEQ ID NO:18; amino acids 947-967 of SEQ ID NO:1), KFIIKRYTPNNEIDSF (SEQ ID NO:19; amino acids 1174-1189 of SEQ ID NO:1), YDPNYLRTDSDKDRFLQTMVKLFNRIK (SEQ ID NO: 20; amino acids 73-99 of SEQ ID NO:1), IDKISDVSTIVPYIGPALNI (SEQ ID NO: 21; amino acids 632-651 of SEQ ID NO:1), NNFTVSFWLRVPKVSASHLET (SEQ ID NO: 22; amino acids 950-969 of SEQ ID NO:1), or TVSFWLRVPKVSASHLE (SEQ ID NO: 41; amino acids 950-967 of SEQ ID NO:1).

Specific examples of CRM-derived peptides include GYVDSIQKGIQKPK (SEQ ID NO: 10; amino acids 26-39 of SEQ ID NO:2), GLTKVLALKVD (SEQ ID NO:11; amino acids 87-97 of SEQ ID NO:2), KTTAALSILPGIGS (SEQ ID NO:12; amino acids 299-312 of SEQ ID NO:2), and TPLPIAGVLLPTIPGK (SEQ ID NO:13; amino acids 425-440 of SEQ ID NO:2).

In some embodiments, a CRM-derived peptide does not include PVFAGANYAAWAVNVAQVI (SEQ ID NO:23; amino acids 271-290 of SEQ ID NO:2), VHHNTEEIVAQSIALSSLMV (SEQ ID NO:24; amino acids 321-350 of SEQ ID NO:2), QSIALSSLMVAQAIPLVGEL (SEQ ID NO:25; amino acids 331-350 of SEQ ID NO:2), VDIGFAAYNFVESIINLFQV (SEQ ID NO:26; amino acids 351-370 of SEQ ID NO:2), QGESGHDIKITAENTPLPIA (SEQ ID NO:27; amino acids 411-430 of SEQ ID NO:2), GVLLPTIPGKLDVNKSKTHI (SEQ ID NO:28; amino acids 431-450 of SEQ ID NO:2), AYNFVESIINLFQVVHNSYNRPAYSPG (SEQ ID NO:29; amino acids 357-383 of SEQ ID NO: 2), PGKLDVNKSKTHISVN (SEQ ID NO:30; amino acids 245-260 of SEQ ID NO: 2), or DVNKSKTHISVNGRKI (SEQ ID NO:31; amino acids 249-264 of SEQ ID NO: 2).

Other examples of peptides of the present disclosure include those having structural similarity with the amino acid sequence of one of SEQ ID NOs: 3-13. As used herein, a peptide may be "structurally similar" to a reference peptide if the amino acid sequence of the peptide possesses a specified amount of structural similarity and/or structural identity compared to the reference peptide. Thus, a peptide may have structural similarity to a reference peptide if, compared to the reference peptide, it possesses a sufficient level of amino acid structural identity, amino acid structural similarity, or a combination thereof. A peptide can be isolated from a cell or from an MHC II complex or can be produced using routine recombinant techniques, or chemically or enzymatically synthesized using routine methods. Methods for determining whether a protein has structural similarity with the amino acid sequence of one of SEQ ID NOs: 3-13 are described herein.

The amino acid sequence of a peptide having structural similarity to one of SEQ ID NOs: 3-13 can include one or more conservative substitutions of amino acids present in one of SEQ ID NOs: 3-13. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this disclosure, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

Whether a peptide is structurally similar to a protein of one of SEQ ID NOs: 3-13 can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. In one embodiment, a reference protein is a protein described at one of SEQ ID NOs: 3-13. A candidate protein is the protein being compared to the reference protein. A candidate protein can be produced using recombinant techniques, or chemically or enzymatically synthesized. In some embodiments when a reference protein includes one or more spacer, the one or more spacer is not considered when determining whether a protein is structurally similar to a reference protein.

Unless modified as otherwise described herein, a pairwise comparison analysis of amino acid sequences can be carried out using the Blastp program of the Blastp suite-2sequences search algorithm, as described by Tatusova et al., (FEMS Microbiol Lett, 174, 247-250 (1999)), and available on the National Center for Biotechnology Information (NCBI) website. The default values for all blastp suite-2sequences search parameters may be used, including general parameters: expect threshold=10, word size=3, short queries=on; scoring parameters: matrix=BLOSUM62, gap costs-existence: 11 extension: 1, compositional adjustments=conditional compositional score matrix adjustment. Alternatively, proteins may be compared using other commercially available algorithms, such as the BESTFIT algorithm in the GCG package (version 10.2, Madison WI).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions.

In one embodiment, the amino acid sequence of a peptide having structural similarity to one of SEQ ID NOs: 3-13 can include at least 1, at least 2, at least 3, at least 4, or at least 5 conservative substitutions of amino acids present in one of SEQ ID NOs: 3-13. In one embodiment, the amino acid sequence of a peptide having structural similarity to one of SEQ ID NOs: 3-13 can include no greater than 5, no greater than 4, no greater than 3, no greater than 2, or no greater than 1 conservative substitutions of amino acids present in one of SEQ ID NOs: 3-13.

Thus, as used herein, reference to an amino acid sequence disclosed at one of SEQ ID NOs: 3-13 can include a protein with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to an amino acid sequence disclosed at one of SEQ ID NOs: 3-13 can include a protein with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Unless a specific level of sequence similarity and/or identity is expressly indicated herein (e.g., at least 80% sequence similarity, at least 90% sequence identity, etc.), reference to the amino acid sequence of an identified SEQ ID NO includes variants having sequence similarity or sequence identity of at least 80%.

A peptide described herein can be a fusion protein, where the additional amino acids can be heterologous amino acids. As used herein, "heterologous amino acids" refers to amino acids that are not normally or naturally found flanking the sequences depicted at, for instance, SEQ ID NOs: 1-31. For instance, the additional amino acid sequence may be useful for purification of the fusion protein by affinity chromatography. Various methods are available for the addition of such affinity purification moieties to proteins. Representative examples may be found in Hopp et al. (U.S. Pat. No. 4,703,004), Hopp et al. (U.S. Pat. No. 4,782,137), Sgarlato (U.S. Pat. No. 5,935,824), and Sharma Sgarlato (U.S. Pat. No. 5,594,115).

In one embodiment a fusion protein is a series of two or more peptides described herein covalently joined together as a multimer. The number of peptides joined together is not limiting and in one embodiment there is no upper number of peptides that can be present in a multimer. In one embodiment, the number of peptides can be at least 2, at least 5, at least 10, at least 50, or at least 100. In one embodiment, the number of peptides can be no greater than 150, no greater than 50, no greater than 10, or no greater than 5.

In one embodiment, each of the peptides of a multimer are TT-derived peptides. In those embodiments where the number of peptides of a multimer is at least 2, the multimer can include 2 peptides that are the same and adjacent to each other within the multimer, or as described herein further including a spacer between the peptides (e.g., a multimer of at least 2 peptides of SEQ ID NO:3, a multimer of at least 2 peptides of SEQ ID NO:4, a multimer of at least 2 peptides of SEQ ID NO:5, a multimer of at least 2 peptides of SEQ ID NO:6, a multimer of at least 2 peptides of SEQ ID NO:7, a multimer of at least 2 peptides of SEQ ID NO: 8, or a multimer of at least 2 peptides of SEQ ID NO:9). In one embodiment, the multimer can include 2 peptides, a first peptide chosen from SEQ ID NO:3-9 and a second peptide being one that is recognized in the art as being a useful carrier, such as one chosen from SEQ ID NO:14-22. Such a multimer of TT-derived peptides can also include one or more additional peptides described herein. In one embodiment, the additional one or more additional peptides are TT-derived peptides, and in one embodiment the additional one or more additional peptides are CRM-derived peptides.

In one embodiment, each of the peptides of a multimer are CRM-derived peptides. In those embodiments where the number of peptides of a multimer is at least 2, the multimer can include 2 peptides that are the same and adjacent to each other within the multimer, or as described herein further including a spacer between the peptides (e.g., a multimer of at least 2 peptides of SEQ ID NO:10, a multimer of at least 2 peptides of SEQ ID NO:11, a multimer of at least 2 peptides of SEQ ID NO:12, or a multimer of at least 2 peptides of SEQ ID NO:13). In one embodiment, the multimer can include 2 peptides, a first peptide chosen from SEQ ID NO:10-13 and a second peptide being one that is recognized in the art as being a useful carrier, such as one chosen from SEQ ID NO:23-31. Such a multimer of CRM-derived peptides can also include one or more additional peptides described herein. In one embodiment, the additional one or more additional peptides are CRM-derived peptides, and in one embodiment the additional one or more additional peptides are TT-derived peptides.

In one embodiment, the peptides of a multimer are joined as a fusion protein where the carboxy-terminal end of one peptide is attached to the amino-terminal end of the next one. In some embodiments, a multimer includes a spacer between the peptides of a multimer. In one embodiment, a spacer is a non-amino acid compound located between the peptides of a multimer and joins the peptides of a multimer. In another embodiment, a spacer is one or more amino acids located between the peptides of a multimer and joins the peptides of a multimer. The amino acids of a spacer can be one or more natural amino acids, one or more unnatural amino acids, or a combination thereof. A spacer can be flexible or rigid, and in one embodiment is flexible. In one embodiment, a spacer can be at least 2, at least 3, at least 4, at least 5, or at least 6 amino acids in length. It is expected that there is no upper limit on the length of a linker used in a multimer described herein; however, in one embodiment, a spacer is no greater than 10, no greater than 9, no greater than 8, no greater than 7, no greater than 6, no greater than 5, or no greater than 4 amino acids in length. A spacer sequence can be any amino acid sequence, and can include amino acids that reduce steric hindrance.

In one embodiment, a spacer includes a cleavable moiety, e.g., an amino acid sequence that is recognized and cleaved by an enzyme such as a protease, or a chemical moiety that is acid labile. A number of such cleavable moieties are known in the art. For example, cleavable sequences can include those recognized by cathepsins such as, but not limited to, valine-citrulline, the amino acid sequence GLFG, and the like (Conus and Simon, 2008, Biochem. Pharmacol., 76:1374-1382; Arnold et al., 1997, Eur: J. Biochm. 249: 171-179; Roberts, 2005, Drug News Perspect., 18 (10): 605; and Plüger et al., 2002, Eur: J. Immunol. 32:467-476). In some embodiments, the cleavable sequence is a recognition sequence for a protease, such as a protease present in an endosome. Acid labile moieties are also known in the art, and can include 4-(4-Hydroxymethyl-3-methoxyphenoxy) butyric acid (SIGMA) (Riniker et al., 1993, Tetrahedron (49) 41:9307-9320). The skilled person will recognize that some methods of joining two peptides, for instance native chemical ligation, are aided by modifying the N-terminal end of a peptide with a cysteine residue, and/or modifying the C-terminal end of a peptide with a valine residue. Accordingly, in some embodiments the peptides of a multimer further include a heterologous amino acid, such as a cysteine residue at one or more N-terminal ends, a valine residue at one or more C-terminal ends, or a combination thereof.

An example of a multimer that includes at least 2 CRM-derived peptides includes a first peptide selected from any one of SEQ ID NO:10-13 and a second peptide selected from any one of SEQ ID NO: 10-13. In one embodiment, an example of a multimer that includes at least 2 CRM-derived peptides includes, but is not limited to, at least 2 peptides of SEQ ID NO: 12. One example is SEQ ID NO:12-optional spacer-SEQ ID NO:12 (KTTAALSILPGIGSXKTTAALSILPGIGS, SEQ ID NO:32), where X is an optional spacer such as valine-citrulline or GFLG (SEQ ID NO:42). In another embodiment, a multimer that includes at least 2 CRM-derived peptides includes, but is not limited to, $X_1$KTTAALSILPGIGS$X_2X_3X_4$KTTAALSILPGIGS$X_5$ (SEQ ID NO:33) where $X_1$ and $X_4$ are each independently an optional modification of the N-terminal end of a peptide that makes up the multimer, such as a cysteine, $X_2$ and $X_5$ are each independently an optional modification of the C-terminal end of a peptide, such as a valine, and $X_3$ is an optional spacer). Examples of multimers described by SEQ ID NO:33 include, but are not limited to, KTTAALSILPGIGSXKTTAALSILPGIGSV (SEQ ID NO:34) where X is spacer such as valine-citrulline or GFLG (SEQ ID NO:42), CKTTAALSILPGIGSXCKTTAALSILPGIGSV (SEQ ID NO:35) where X is spacer such as valine-citrulline or GFLG, and KTTAALSILPGIGSXKTTAALSILPGPIGSV (SEQ ID NO: 36) where X is spacer such as valine-citrulline or GFLG (SEQ ID NO:42).

An example of a multimer that includes at least 2 TT-derived peptides includes a first peptide selected from any one of SEQ ID NO:3-9 and a second peptide selected from any one of SEQ ID NO:3-9. An example of a multimer that includes at least 2 TT-derived peptides includes, but is not limited to, a first peptide chosen from SEQ ID NO:6 or SEQ ID NO: 7 and a second peptide SEQ ID NO:6 (first peptide-optional spacer-SEQ ID NO:6, or $X_1X_2$CKALNPKEIE SEQ ID NO:37, where $X_1$ is SEQ ID NO:6 or 7, and where $X_2$ is an optional spacer such as valine-citrulline or GFLG). One example is SEQ ID NO:6-optional spacer-SEQ ID NO:6 (CKALNPKEIEXCKALNPKEIE, SEQ ID NO:38), where X is an optional spacer such as valine-citrulline or GFLG). In another embodiment, a multimer that includes at least 2 CRM-derived peptides includes, but is not limited to, SEQ ID NO: 7-spacer-SEQ ID NO:6 (XILYNGLKFIIKR$X_2X_3$CKALNPKEIE$X_4$, SEQ ID NO: 39) where $X_1$ is an optional modification of the N-terminal end of the peptide SEQ ID NO: 7, such as a cysteine, $X_2$ and $X_4$ are each independently an optional modification of the C-terminal end of a peptide, such as a valine, and $X_3$ is an optional spacer). An example of a multimer described by SEQ ID NO:39 includes, but is not limited to, CLYNGLKFIIKRXCKALNPKEIE (SEQ ID NO:40) where X is valine-citrulline.

Antigens

A TT-derived peptide or a CRM-derived peptide described herein, such as a multimer, can include one or more antigen. An antigen can be any compound that is immunogenic, such as, but not limited to, a carbohydrate, a lipid, a nucleic acid, or a peptide. In one embodiment, the compound is expressed by a prokaryotic cell, a eukaryotic cell (including, for instance a fungus, yeast, or protozoan) or a virus, including a prokaryotic pathogen, a eukaryotic pathogen, or a viral pathogen. Antigenic compounds encoded by a prokaryotic cell, a eukaryotic cell, or a virus are known to the skilled person in the art.

In one embodiment, an antigen is immunogenic, e.g., it is a compound that can, by itself when administered as a monomer, elicit an immune response. In one embodiment, an antigen is a reduced immunogenicity antigen (RIA). As used herein, a "reduced immunogenicity antigen," also referred to herein as RIA, is an antigen which is poorly immunogenic by itself. In some examples, a RIA is a molecule which cannot, by itself, elicit an immune response. In other examples, a RIA is a molecule which can, by itself, elicit an immune response. Some RIAs may be able to induce an immune response when several molecules of the RIA are linked together as a multimer. As described herein, immunogenicity of a RIA may be achieved or increased by covalently attaching (referred to herein as linking, joining, or conjugating) the RIA to one or more peptides (e.g., a monomer or a multimer) of the present disclosure. Typically, antibody produced in response to a RIA-carrier conjugate will specifically bind to the RIA in its free state.

It is expected that the immunogenicity of any antigen or RIA can be increased by attachment to one or more peptides (e.g., a monomer or a multimer) described herein. Databases that describe thousands of RIAs are available in the art (see, e.g., Gunther et al., 2007, Nucl. Acids Res. 35: D906-D910; Singh et al., 2006, Bioinformatics 2006, 22:253-255). Specific examples include, but are not limited to, a small organic molecule, a carbohydrate (e.g., a monosaccharide, a disaccharide, or an oligosaccharide), a lipid, a nucleic acid, or a peptide.

In one embodiment, a RIA can include a carbohydrate, such as a carbohydrate of a pathogenic microorganism or a carbohydrate from a self-antigen, such as a tumor antigen. In some embodiments, the carbohydrate RIA is derived from a pathogenic microorganism (e.g., bacterium, virus, fungus, protozoan, parasite). Carbohydrates associated with pathogenic microorganisms can be expressed on their surface, secreted, shed, or on the surface of infected host cells. Carbohydrate RIAs from a pathogenic microorganism may be from capsules that include a polysaccharide (e.g., a capsular polysaccharide), a lipopolysaccharide, an exopolysaccharide (e.g., polysaccharide that form a biofilm), an O-linked polysaccharide, a mannan (e.g., from *Candida albicans*), a lipophosphoglycan (e.g., from *Leishmania major*), or a viral glycoprotein. Examples of pathogenic microbes that can be the source of polysaccharides include, but are not limited to, *Staphylococcus aureus*, group A *Streptococcus, Klebsiella* spp., *Clostridium difficile, Neisseria meningitidis, S. agalactiae* (group B *Streptococcus*) and *Shigella flexneri*. In another embodiment, a carbohydrate RIA is a self-antigen, for example a tumor antigen. In some embodiments, the carbohydrate RIA is derived from a self-antigen. Examples of a carbohydrate RIA from a tumor include, for example, a glycosphingolipid, a mucin-type carbohydrate, a lactosylceramide, $Le^x$, $Le^Y$, GD3, GD2, Globo-H, GB3, or Tn antigen.

In one embodiment, a polysaccharide includes one or more terminal galactose residues. In one embodiment, a polysaccharide includes one or more terminal glucose, n-acetylglucosamine (GlcNAc), mannose, or n-acetylmannosamine (ManNAc) residues, or a combination thereof.

In one embodiment, a carbohydrate RIA includes a capsular polysaccharide of *Streptococcus pneumoniae*. Examples of capsular polysaccharides of *S. pneumoniae* include, but are not limited to serotypes 2, 3, 4, 5, 6A, 6B, 6C, 6D, 7A, 7F, 8, 9N, 10A, 12F, 13, 14, 15A, 15A, 15F, 17A, 17F, 19A, 19C, 19F, 22F, 32A, 32F, 33A, 33B, 33C, 33D, 33F, 35A, 37, 39, and 42.

In one embodiment, the capsular polysaccharide is a type III capsular polysaccharide of *S. pneumoniae*. This capsular polysaccharide is also known as Pneumococcal type-3 polysaccharide (Pn3P) and is expressed by serotype 3 (also referred to as type 3) *S. pneumoniae* (WO 2019/036373). In one embodiment, a Pn3P oligosaccharide is native, and in another embodiment, it is a reduced-molecular weight Pn3P oligosaccharide. In one embodiment, a Pn3P oligosaccharide is a monomer. In one embodiment a Pn3P oligosaccharide conjugated to a peptide is specifically sized as a 2, 3, 4, 5, 6, 7, 8 or greater. In one embodiment, the Pn3P oligosaccharide includes the repeating glucuronic acid-glucose [-3)-β-D-GlcA-(1-4)-β-D-Glc-(1-] glycan structure. In one embodiment, the Pn3P oligosaccharide has a reducing end monosaccharide differ that differs based upon which strategy is harnessed to depolymerize the full length Pn3P into oligosaccharides (Reeves and Goebel, 1941, J. Biol. Chem., 139:511-519; Geno et al., 2015, Clinical Microbiology Reviews, 28 (3): 871-899). In one embodiment, a carbohydrate RIA includes one or more of the other *S. pneumoniae* polysaccharides that make up the 13-valent conjugate vaccine or the 23-valent polysaccharide vaccine (Wantuch and Avci, 2018, Human Vaccines and Immunotherapeutics, 14:2303-2309).

In one embodiment, a carbohydrate RIA includes a capsular polysaccharide of *Neisseria meningitidis* serogroup Y or W135; *S. agalactiae* (group B *Streptococcus*) type II or IV; or *Shigella flexneri* serotype D1, B4, B5, B14, D3, O164, O40, D11, D13, X, Xv, or 2A LPS.

Naturally occurring carbohydrates can be processed using known and routine methods to obtain useful RIAs. For instance, enzymatic degradation to oligosaccharides with GlcA reducing ends can be achieved using the type 3-specific glycoside hydrolase Pn3Pase (Middleton et al., 2018, Infect. Immun. 86: e00316-18). In another example, trifluoroacetic acid treatment of a carbohydrate such as Pn3P can be used to hydrolyze the polysaccharide, which can be monitored by treatment time to provide oligosaccharides with Glc reducing ends (Middleton et al., 2017, J. Immunol., 199 (2): 598-603). In another example, hydrogen peroxide and cupric acetate can be used for reactive oxygen species generation to partially depolymerize a carbohydrate, such as Pn3P, by radical oxidative depolymerization into oligosaccharides with both Glc and GlcA reducing ends (Li et al., 2015, J. Chroma. A, 1397:43-51). In another example, galactose oxidase (GOase) can be used. Methods for using GOase are described herein.

In one embodiment, an antigen, such as a RIA includes a toxin. Examples of toxins, including RIA toxins, include but are not limited to, a pathogenic microorganism (e.g., bacterium, virus, fungus, protozoan, parasite), a venomous organism, or a chemical weapon. In one embodiment, a RIA includes a hazardous environmental agent.

In one embodiment, an antigen, such as a RIA includes a protein. A protein, such as a RIA peptide, may be a foreign antigen, for example, a protein from a pathogenic microorganism pathogenic microorganism (e.g., bacterium, virus, fungus, protozoan, parasite), or a self-antigen. A self-antigen may be, for instance, a cancer disease antigen, autoimmune disease antigen, alloantigen, xenoantigen, or metabolic disease enzyme. The use of self-antigens or a pathogenic microorganism antigen in cancer or infectious disease peptide vaccine development is known in the art and routine.

Attachment of the antigen, such as a RIA, and carrier (e.g., a monomer or a multimer) of the present disclosure can be achieved in a variety of different ways. The carrier and RIA may be directly associated with one another, e.g., by one or more covalent bonds, or may be associated by one or more linkers. Any suitable linker can be used. One or more linkers can be used to form an amide linkage, an ester linkage, a disulfide linkage, etc. Typically, a linker is 1 to 50 atoms long. In one embodiment, a RIA is attached to a lysine or aspartic acid residue of a carrier. More than one RIA can be attached to a carrier.

In those embodiments where the carbohydrate RIA is a Pn3P, the formation of glycoconjugates can be performed through multiple methods. The reducing end monosaccharide of Pn3P shifts conformation from a cyclic to open-chain form, thus exposing an aldehyde. This aldehyde can be used to couple, either through direct reductive amination to carrier by conjugation to lysines, or through further formation of a permanent aldehyde handle by first reducing the transient aldehyde into a permanent diol that is susceptible to low concentrations of sodium periodate for the oxidative cleavage and formation of a permanent reducing end aldehyde (Gildersleeve et al., 2008, Bioconjug. Chem., 19 (7): 1485-1490; Jennings and Lugowski, J. Immunol., 127 (3): 1011-1018). Functionalization of the reducing end can be accomplished through attachment with adipic acid dihydrazide by hydrazine-aldehyde chemistry, which can be further oxidatively converted into an acyl azide and then a thioester capable of transthioesterification with cysteine residues on a peptide (Cheng et al., 2019, Org. Biomol. Chem., 17:2646-2650). Non-reducing end chemistries include: EDC carbodiimide coupling using the carboxylic acid found on GlcA to attach to lysine residues (Farkas et al., 2013, International Journal of Biological Macromolecules, 60:325-327). Formation of aldehydes can be accomplished along the structure of Pn3P using higher concentrations of sodium periodate to act on the glucose residues, oxidizing and opening the ring to form aldehyde handles for conjugation (Middleton et al., 2017, J. Immunol., 199:598-603.

Activity

A peptide (e.g., a monomer or a multimer) described herein has immunoregulatory (IR) activity. IR activity includes the ability to elicit a T cell response (including a CD4+ T cell response), and/or increase the immunogenicity of an attached RIA, and/or induce the production of RIA-specific antibodies.

Whether a peptide (e.g., a monomer or a multimer) has IR activity can be determined by in vitro or in vivo assays. In one embodiment, an assay determines T-cell proliferation and can be carried out as described in Example 1. For instance, peripheral blood mononuclear cells (PBMCs) can be isolated and stimulated with a peptide of the present disclosure and IL-2, and after exposure to suitable conditions the extent of proliferation can be measured by, for example, CFSE depletion and cytokine production. In those embodiments where the source of PBMCs is an outbred population, such as humans, IR activity of a peptide can be and preferably is determined using PBMCs from several donors, where it is expected that PBMCs of some but not all donors will proliferate (see Example I). In one embodiment, the T cells that proliferate are CD4+ T cells.

In one embodiment, a peptide (e.g., a monomer or a multimer) described herein elicits a T cell response that is greater than a reference peptide. In one embodiment, the increased T cell response to a peptide of the present disclosure is statistically significant when compared to the T cell response of a reference peptide. In one embodiment, significance can be determined using Student's t test with $p<0.05$.

Examples of reference peptides for evaluating a TT-derived peptide include QYIKANSKFIGITEL (SEQ ID NO:14, amino acids 830-844 of SEQ ID NO:1), GQIGND-PNRDIL (SEQ ID NO:15, amino acids 1273-1284 of SEQ ID NO: 1), VSIDKFRIFCKALNPK (SEQ ID NO: 16, amino acids 1084-1099 of SEQ ID NO: 1), YDTEYYLIP-VASSSKD (SEQ ID NO:17, amino acids 1124-1139 of SEQ ID NO: 1), FNNFTVSFWLRVPKVSASHLE (SEQ ID NO:18, amino acids 947-967 of SEQ ID NO: 1), KFIIKRYTPNNEIDSF (SEQ ID NO:19, amino acids 1174-1189 of SEQ ID NO: 1), YDP-NYLRTDSDKDRFLQTMVKLFNRIK (SEQ ID NO:20, amino acids 73-99 of SEQ ID NO:1), IDKISDVS-TIVPYIGPALNI (SEQ ID NO:21, amino acids 632-651 of SEQ ID NO:1), NNFTVSFWLRVPKVSASHLET (SEQ ID NO:22, amino acids 950-969 of SEQ ID NO:1), and TVSFWLRVPKVSASHLE (SEQ ID NO:41; amino acids 950-967 of SEQ ID NO:1). These peptides are referred to herein as TT reference peptides. In one embodiment, the reference peptide for evaluating a TT-derived peptide is QYIKANSKFIGITEL (referred to herein as P2, SEQ ID NO:14) or KFIIKRYTPNNEIDSF (referred to herein as P32, SEQ ID NO:19).

Examples of reference peptides for evaluating a CRM-derived peptide include PVFAGANYAAWAVNVAQVI (SEQ ID NO:23, amino acids 271-290 of SEQ ID NO:2), VHHNTEEIVAQSIALSSLMV (SEQ ID NO:24, amino acids 321-350 of SEQ ID NO:2), QSIALSSLMVAQAIPLV-GEL (SEQ ID NO:25, amino acids 331-350 of SEQ ID NO:2), VDIGFAAYNFVESIINLFQV (SEQ ID NO:26, amino acids 351-370 of SEQ ID NO:2), QGESGHDIKI-TAENTPLPIA (SEQ ID NO:27, amino acids 411-430 of SEQ ID NO:2), GVLLPTIPGKLDVNKSKTHI (SEQ ID NO:28, amino acids 431-450 of SEQ ID NO:2), AYNFVESIINLFQVVHNSYNRPAYSPG (SEQ ID NO:29, amino acids 357-383 of SEQ ID NO: 2), PGKLDVNK-SKTHISVN (SEQ ID NO:30, amino acids 245-260 of SEQ ID NO: 2), or DVNKSKTHISVNGRKI (SEQ ID NO:31, amino acids 249-264 of SEQ ID NO: 2). These peptides are referred to herein as CRM reference peptides.

Polynucleotides

The present disclosure also includes isolated polynucleotides encoding a peptide (e.g., a monomer or a multimer) described herein. A polynucleotide encoding a protein described herein can have a nucleotide sequence encoding a protein having the amino acid sequence of a peptide described herein, such as any one of SEQ ID NOs: 3-13, or a peptide that is structurally similar. A nucleotide sequence of a polynucleotide encoding a peptide described herein can be readily determined by one skilled in the art by reference to the standard genetic code, where different nucleotide triplets (codons) are known to encode a specific amino acid. As is readily apparent to a skilled person, the class of nucleotide sequences that encode any protein described herein is large as a result of the degeneracy of the genetic code, but it is also finite.

A polynucleotide encoding a peptide described herein can be present in a vector. A vector is a replicating polynucleotide, such as a plasmid, phage, or cosmid, to which another polynucleotide may be attached so as to bring about the replication of the attached polynucleotide. Construction of vectors containing a polynucleotide employs standard ligation techniques known in the art. See, e.g., Sambrook et al, Molecular Cloning: A Laboratory Manual, Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, adenoviral vectors, adeno-associated viral vectors, lentiviral vectors, retroviral vectors, and herpes virus vectors. Typically, a vector is capable of replication in a microbial host, for instance, a prokaryotic bacterium, such as *E. coli*. Preferably the vector is a plasmid.

Selection of a vector depends upon a variety of desired characteristics in the resulting construct, such as a selection marker, vector replication rate, and the like. Suitable host cells for cloning or expressing the vectors herein include prokaryotic and eukaryotic cells. Suitable prokaryotic cells include eubacteria, such as gram-negative microbes, for example, *E. coli*. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides can be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known.

An expression vector optionally includes regulatory sequences operably linked to the coding region. The disclosure is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell.

An expression vector may optionally include a ribosome binding site and a start site (e.g., the codon ATG) to initiate translation of the transcribed message to produce the peptide. It may also include a termination sequence to end translation. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, and neomycin.

A peptide (e.g., a monomer or a multimer) described herein may be produced using recombinant DNA techniques, such as an expression vector present in a cell (e.g., a genetically modified cell described herein). Such methods are routine and known in the art. A peptide can also be synthesized in vitro, e.g., by solid phase peptide synthetic methods. The solid phase peptide synthetic methods are routine and known in the art. A peptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

Genetically Modified Cells

The present disclosure also includes genetically modified cells that have an exogenous polynucleotide encoding a peptide (e.g., a monomer or a multimer) described herein. As used herein, "genetically modified cell" refers to a cell into which has been introduced an exogenous polynucleotide. For example, a cell is a genetically modified cell by virtue of introduction into a suitable cell of an exogenous polynucleotide. Compared to a control cell that is not genetically modified, a genetically modified cell can exhibit production of a peptide described herein. A polynucleotide encoding a peptide can be present in the organism as a vector or integrated into a chromosome. A genetically engineered cell can stably express a peptide, or the expression can be transient.

Examples of cells include, for instance, prokaryotic (e.g., microbial) and eukaryotic. Examples of eukaryotic cells include yeast, insect, and animal cells. Examples of animal cells include vertebrate cells, such as mammalian cells. An animal cell can be an in vitro cell (e.g., a cell that is capable of long term culture in tissue culture medium), or an ex vivo cell (e.g., a cell that has been removed from the body of a subject and capable of limited growth in tissue culture medium).

Compositions

Also provided are compositions that include a peptide described herein or a polynucleotide encoding a peptide. The peptide present in a composition can be in monomer form (e.g., a population of a single peptide) or a multimer (e.g., a population of at least two peptides joined as a fusion protein), or a combination thereof. In one embodiment, the peptide present in a composition can include an antigen, such as a RIA. As described herein, the RIA can be a single molecule or a multimer of antigens, and a peptide can include one type of antigen or more than one type of antigen. Reference to an "active agent" refers to each of these embodiments, e.g., a peptide monomer or multimer that optionally includes one or more antigens.

A composition can include a pharmaceutically acceptable excipient. As used herein "pharmaceutically acceptable excipient" includes saline, solvents, dispersion media, coatings, antibacterial and antifungal agents, isotonic and absorption delaying agents, and the like, compatible with pharmaceutical administration.

A composition may be prepared by methods well known in the art of pharmaceutics. In general, a composition can be formulated to be compatible with its intended route of administration. Administration may be systemic or local. Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of the compound of the present disclosure include, but are not limited to, tablets, capsules, or liquids. Appropriate dosage forms for parenteral administration may include intravenous or intraperitoneal administration. Appropriate dosage forms for topical administration include, but are not limited to, nasal sprays, metered dose inhalers, dry-powder inhalers, or by nebulization.

Solutions or suspensions can include the following components: a sterile diluent such as water for administration, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide.

Compositions can include sterile aqueous solutions (where water soluble) or dispersions and sterile powders for the extemporaneous preparation of sterile solutions or dispersions. For parenteral administration, suitable excipients include physiological saline, bacteriostatic water, phosphate buffered saline (PBS), and the like. A composition is typically sterile and, when suitable for injectable use, should be fluid to the extent that easy syringability exists. It should be stable under the conditions of manufacture and storage and preserved against the contaminating action of microorganisms such as bacteria and fungi. The excipient can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active agent in the required amount in an appropriate solvent with one or a combination of ingredients routinely used in pharmaceutical compositions, as required, followed by filtered sterilization. Generally, dispersions are prepared by incorporating the active agent into a sterile vehicle, which contains a basic dispersion medium and any other appropriate ingredients. In the case of sterile powders for the preparation of sterile injectable solutions, methods of preparation include but are not limited to vacuum drying and freeze-drying which yields a powder of the active agent plus any additional desired ingredient from a previously sterilized solution thereof.

Oral compositions generally include an inert diluent or an edible excipient. For the purpose of oral therapeutic administration, the active agent can be incorporated with inert substances and used in the form of tablets, troches, or capsules, e.g., gelatin capsules. Oral compositions can also be prepared using a fluid excipient. Pharmaceutically compatible binding agents and/or other useful materials can be included as part of the composition. The tablets, pills, capsules, troches and the like can contain any of the following ingredients, or compounds of a similar nature: a binder such as microcrystalline cellulose, gum tragacanth or gelatin; an inert substance such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation (e.g., topical administration), the active agent can be delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and/or fusidic acid derivatives. Transmucosal administration can be accomplished through the use of nasal sprays or suppositories. For transdermal administration, the active agent is formulated into ointments, salves, gels, or creams as generally known in the art.

The active agent may be prepared with excipients that will protect the agent against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions can also be used as pharmaceutically acceptable excipient. These can be prepared according to methods known to those skilled in the art.

Toxicity and therapeutic efficacy of an active agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Recombinant peptides exhibiting high therapeutic indices are preferred.

The data obtained from cell culture assays and animal studies can be used in formulating a range of dosage for use in humans. The dosage of an active agent lies preferably within a range of circulating concentrations that include the ED50 with little or no toxicity. The dosage may vary within this range depending upon the dosage form employed and the route of administration used. For an agent used in the methods described herein, the therapeutically effective dose can be estimated initially from animal models. A dose may be formulated in animal models to achieve an immune response. Such information can be used to more accurately determine useful doses in humans. Levels in plasma may be measured using routine methods.

A composition is administered in an amount sufficient to provide an immunological response to a peptide (e.g., a monomer or a multimer), peptide-antigen, or peptide-RIA conjugate described herein. The amount of peptide present in a composition can vary. For instance, the dosage of peptide can be between 0.01 micrograms (μg) and 1000 milligrams (mg), typically between 10 μg and 10000 μg. For an injectable composition (e.g. subcutaneous, intramuscular, etc.) the peptide can be present in the composition in an amount such that the total volume of the composition administered is 0.1 ml to 5.0 ml, typically 0.5-1.0 ml. The compositions can be administered one or more times per day to one or more times per week, including once every other day. The skilled artisan will appreciate that certain factors may influence the dosage and timing required to effectively treat a subject, including but not limited to the severity of the condition, previous treatments, physical condition, health, age, weight, type and extent of the disease or disorder of the recipient, frequency of treatment, the nature of concurrent therapy, if required, and the nature and scope of the desired effect(s). Moreover, treatment of a subject with an effective amount of an active agent can include a single treatment or, preferably, can include a series of treatments. Such factors can be determined by one skilled in the art.

A composition including a pharmaceutically acceptable excipient can also include an adjuvant. An "adjuvant" refers to an agent that can act in a nonspecific manner to enhance an immune response to that peptide (e.g., a monomer or a multimer), peptide-antigen, or peptide-RIA conjugate, thus potentially reducing the quantity of antigen necessary in any given immunizing composition, and/or the frequency of injection necessary in order to generate an adequate immune response. Adjuvants include, but are not limited to, ALUM, Freund's (complete or incomplete), IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (available from under the tradename EMULSIGEN from MVP Laboratories, Ralston, Nebraska), ISA-70, RIBI and other substances known in the art.

Additional agents can also be incorporated into a composition. In one embodiment, a composition can include a biological response modifier, such as, for example, IL-2, IL-4 and/or IL-6, TNF, IFN-alpha, IFN-gamma, and other cytokines that effect immune cells. In another embodiment, a composition can include an inhibitor of degradation of the peptide.

A composition can be included in a container, pack, or dispenser together with instructions for administration. In one aspect, a pharmaceutical composition can be included as a part of a kit.

Methods

Also provided are methods. In one embodiment, a method is for making an antigen-carrier, such as a RIA-carrier conjugate, described herein. In one embodiment, the method includes contacting a peptide of the present disclosure and a RIA under conditions suitable for the RIA to be covalently attached to the peptide. Suitable conditions for conjugating an antigen, such as a small organic molecule, a carbohydrate (e.g., a monosaccharide, a disaccharide, or an oligosaccharide), a lipid, a nucleic acid, or a peptide to a carrier described herein (e.g., a monomer or a multimer) are known in the art and routine.

In one embodiment, a conjugate of a carbohydrate, such as a capsular polysaccharide, and a carrier is made using galactose oxidase (GOase) and reductive amination. Typically, the polysaccharide is modified to a desired size, for instance, by ozonolysis. Examples of suitable sizes of polysaccharides are from at least 25 kDa, at least 50 kDa, or at least 75 kDa, and no greater than 150 kDa, no greater than 200 kDa, or no greater than 300 kDa. In one embodiment, the polysaccharides used are from 50 kDa to 150 kDa.

The polysaccharide is exposed to the GOase under conditions suitable for oxidation of the polysaccharide by the GOase. For instance, a buffer such as sodium carbonate can be used, and catalase can be included to decompose the hydrogen peroxide formed by the reaction. Other conditions can include high oxygen and a temperature 37° C. The GOase can be a wild-type enzyme or one that has been modified to have an altered and expanded substrate specificity (Rannes et al., 2011, J. Am. Chem. Soc., 133:8436-8439, dx.doi.org/10.1021/ja201847). The result is multiple sites of oxidation along the polysaccharide chain. When a wild-type GOase is used, terminal galactose residues are oxidized. When the mutant GOase is used, the terminal carbohydrates glucose, n-acetylglucosamine (GlcNAc), mannose, and n-acetylmannosamine (ManNAc) are oxidized. The enzyme can be inactivated, for instance by heat shock, and the oxidized polysaccharide isolated using standard methods.

The conjugation of the oxidized polysaccharide to the carrier (e.g., a monomer or a multimer) can occur by combining the two under suitable conditions. For instance, the two can be mixed, and optionally the volume of the reaction decreased, where the conditions include a reducing agent, such as sodium cyanoborohydride. After reductive amination occurs, the reaction can be treated with a suitable agent, such as sodium borohydride, to quench the reaction and convert any unreacted aldehyde groups back into the native alcohol. The conjugated polysaccharide-carrier can be isolated using routine methods, and routine methods can also be used to identify the presence of the conjugate. The product can be desalted using routine methods. Optionally, the product can be subjected to conditions suitable for long term storage, such as freezing followed by lyophilization.

In one embodiment, a method includes administering to a subject an effective amount of a composition described herein. As used herein, an "effective amount" of a composition described herein is the amount able to elicit the desired response in the recipient. The subject can be, for instance, murine (e.g., a mouse or rat), or a primate, such as a human.

In one embodiment, a method includes inducing in a subject an immune response to the antigen, such as a RIA. In this embodiment, an "effective amount" is an amount effective to result in the production of an immune response to the RIA in the animal. The immune response can be humeral, cell-based, or a combination thereof. A humeral immune response includes the production of antibodies that are antigen-specific and bind the RIA component of the carrier-RIA conjugate used to induce the immune response. In one embodiment, antibody produced binds the RIA in the free state (e.g., the RIA not bound to the carrier). Methods for determining whether a subject has produced antibodies that specifically bind a carrier-RIA conjugate and a RIA described herein can be determined using routine methods. A cell-based response includes the production of T cells that produce interleukin-4 and/or interferon-gamma after stimulation by the carrier-RIA or by the RIA used to induce the immune response. The subject can be, for instance, murine (e.g., a mouse or rat), or a primate, such as a human.

As used herein, an antibody that can "specifically bind" an antigen, e.g., a carrier or a RIA, is an antibody that interacts with the epitope of the carrier-RIA conjugate that induced the synthesis of the antibody or interacts with a structurally related epitope. Antibody can specifically bind the carrier, the RIA, and/or the carrier-RIA conjugate.

In one embodiment, a method includes treating an infection in a subject. As used herein, the term "infection" refers to the presence of a pathogen in a subject's body, which may or may not be clinically apparent. A pathogen can be a prokaryotic (a bacterium), a virus, a fungus, a protozoan, or a parasite. In one embodiment, the pathogen is a prokaryote that includes a capsular polysaccharide. An example of such a pathogen includes, but is not limited to, a *Streptococcus pneumoniae, Staphylococcus aureus*, group A *Streptococcus, Klebsiella* spp., *Clostridium difficile, Neisseria meningitidis, S. agalactiae* (group B *Streptococcus*) and *Shigella flexneri* such as a serotype 3 *S. pneumoniae*. The subject can be, for instance, murine (e.g., a mouse or rat), or a primate, such as a human.

Treating an infection can be prophylactic or, alternatively, can be initiated after the animal is infected by the pathogen. Treatment that is prophylactic—e.g., initiated before a subject is infected by the pathogen or while any infection remains subclinical—is referred to herein as treatment of a subject that is "at risk" of infection. As used herein, the term "at risk" refers to a subject that may or may not actually be infected by the pathogen. Thus, typically, a subject "at risk" of infection by a pathogen is a subject that is a member of a population at increased risk of being exposed to the pathogen. Accordingly, administration of a composition can be performed before, during, or after the subject has first contact with the pathogen. Treatment initiated after the subject's first contact with the pathogen may result in decreasing the severity of symptoms and/or clinical signs of infection by the pathogen, completely removing the pathogen, and/or decreasing the likelihood of experiencing a clinically evident infection. As used herein, the term "symptom" refers to subjective evidence of a disease or condition experienced by a subject and caused by an infection. As used herein, the term "clinical sign" or, simply, "sign" refers to objective evidence of disease or condition caused by infection by a pathogen. Symptoms and/or clinical signs associated with conditions referred to herein and the evaluations of such symptoms are routine and known in the art.

The method includes administering an effective amount of a composition described herein to a subject having, or at risk of having, an infection. In one embodiment, whether the amount of pathogen in the subject has decreased is determined. In this embodiment, an "effective amount" is an amount effective to reduce the amount of the pathogen in a subject, or reduce the likelihood that the subject experiences a clinically-evident infection. Methods for determining whether a subject has an infection are routine for essentially all pathogens and known in the art, as are methods for determining whether the infection has decreased.

In another embodiment, a method includes treating one or more symptoms or clinical signs of certain conditions in a subject that may be caused by infection by a pathogen. The method includes administering an effective amount of a composition described herein to an animal having or at risk of having a condition, or exhibiting symptoms and/or clinical signs of a condition, and determining whether at least one symptom and/or clinical sign of the condition is changed, preferably, reduced.

A method of the present disclosure can further include additional administrations (e.g., one or more booster administrations) of the composition to the subject to enhance or stimulate a secondary immune response. A booster can be administered at a time after the first administration, for instance, one to eight weeks, such as two to four weeks, after the first administration of the composition. Subsequent boosters can be administered one, two, three, four, or more times annually.

ILLUSTRATIVE EMBODIMENTS

Embodiment 1 is (i) a multimer that includes a first peptide selected from an amino acid sequence having at least 80% identity to SEQ ID NO:12, 10, 11, or 13 and a second peptide selected from an amino acid sequence having at least 80% identity to SEQ ID NO: 12, 10, 11, or 13, or (ii) a multimer that includes a first peptide selected from an amino acid sequence having at least 80% identity to any one of SEQ ID NO:3-9 and a second peptide selected from an amino acid sequence having at least 80% identity to any one of SEQ ID NO: 3-9, where the multimer optionally includes a spacer between the first peptide and the second peptide.

Embodiment 2 is a multimer that includes (i) an amino acid sequence having at least 80% identity to KTTAALSILPGIGSXKTTAALSILPGIGS (SEQ ID NO:32) wherein X includes a spacer, or (ii) an amino acid sequence having at least 80% identity to $X_1X_2$CKALNPKEIE (SEQ ID NO:37) wherein $X_1$ is SEQ ID NO:6 or 7, and wherein $X_2$ includes a spacer. For instance, the multimer can include at least two copies of the amino acid sequence having at least 80% identity to KTTAALSILPGIGSXKTTAALSILPGIGS (SEQ ID NO:32), or the multimer can include at least two copies of the amino acid sequence having at least 80% identity to $X_1X_2$CKALNPKEIE (SEQ ID NO:37). The multimer of Embodiment 2 can include a spacer between (i) the at least two copies of the amino acid sequence having at least 80% identity to KTTAALSILPGIGSXKTTAALSILPGIGS (SEQ ID NO:32), or (ii) the at least two copies of the amino acid sequence having at least 80% identity to $X_1X_2$CKALNPKEIE (SEQ ID NO: 37).

Embodiment 3 is the spacer of the multimer of Embodiments 1 or 2, where the spacer includes a cleavable sequence, such as a cathepsin-sensitive sequence or an acid labile chemical moiety. The multimer of Embodiment 4 is the multimer of Embodiments 1 to 3 further including one or more heterologous amino acids at the amino terminal end, the carboxy terminal end, or both amino terminal and carboxy terminal ends. The one or more heterologous amino acids can include a cysteine residue at one or more N-terminal ends, a valine residue at one or more C-terminal ends, or a combination thereof.

Embodiment 5 is an isolated peptide that includes an amino acid sequence having structural similarity to an amino acid sequence of at least 8 and no greater than 30 consecutive amino acids selected from SEQ ID NO:1, wherein the isolated peptide (i) binds a major histocompatibility complex class II (MHCII) molecule expressed by a cell of human B-cell lymphoblast line ATCC CCL-86, (ii) stimulates proliferation of CD4+ T-cells that is a statistically significant increase compared to a negative control of no peptide, or (iii) stimulates proliferation of CD4+ T-cells that is a statistically significant increase compared to a TT reference peptide, or a combination thereof. Examples of isolated peptides of Embodiment 5 include, but are not limited to, LFNRIKNNVAGEAL (SEQ ID NO:3), NFIGALET (SEQ ID NO:4), NILMQYIKANSK (SEQ ID NO:5), CKALNPKEIE (SEQ ID NO: 6), LYNGLKFIIKR (SEQ ID NO:7), DRILRVGYNAPGIPL (SEQ ID NO:8), and GYNAPGIPLYKK (SEQ ID NO:9). In one aspect, examples of isolated peptides of Embodiment 5 do not include QYIKANSKFIGITEL (SEQ ID NO:14), GQIGNDPNRDIL (SEQ ID NO:15), VSIDKFRIFCKALNPK (SEQ ID NO:16), YDTEYYLIPVASSSKD (SEQ ID NO:17), FNNFTVSFWLRVPKVSASHLE (SEQ ID NO:18), KFIIKRYTPNNEIDSF (SEQ ID NO:19), YDPNYLRTDSDKDRFLQTMVKLFNRIK (SEQ ID NO:20), IDKISDVSTIVPYIGPALNI (SEQ ID NO:21), NNFTVSFWLRVPKVSASHLET (SEQ ID NO:22), or TVSFWLRVPKVSASHLE (SEQ ID NO: 41).

Embodiment 6 is an isolated peptide that includes an amino acid sequence having structural similarity to an amino acid sequence of at least 8 and no greater than 30 consecutive amino acids selected from SEQ ID NO:2, wherein the isolated peptide (i) binds a major histocompatibility complex class II (MHCII) molecule expressed by a cell of human B-cell lymphoblast line ATCC CCL-86, (ii) stimulates proliferation of CD4+ T-cells that is a statistically significant increase compared to a negative control of no peptide, or (iii) stimulates proliferation of CD4+ T-cells that is a statistically significant increase compared to a CRM reference peptide, or a combination thereof. Examples of isolated peptides of Embodiment 5 include, but are not limited to, GYVDSIQKGIQKPK (SEQ ID NO:10), GLTKVLALKVD (SEQ ID NO:11, KTTAALSILPGIGS (SEQ ID NO:12), and TPLPIAGVLLPTIPGK (SEQ ID NO:13). In one aspect, examples of isolated peptides of Embodiment 5 do not include PVFAGANYAAWAVNVAQVI (SEQ ID NO:23), VHHNTEEIVAQSIALSSLMV (SEQ ID NO:24), QSIALSSLMVAQAIPLVGEL (SEQ ID NO: 25), VDIGFAAYNFVESIINLFQV (SEQ ID NO:26), QGESGHDIKITAENTPLPIA (SEQ ID NO:27), GVLLPTIPGKLDVNKSKTHI (SEQ ID NO:28), AYNFVESIINLFQVVHNSYNRPAYSPG (SEQ ID NO:29), PGKLDVNKSKTHISVN (SEQ ID NO:30), or DVNKSKTHISVNGRKI (SEQ ID NO:31).

Embodiment 7 is the isolated peptide of Embodiment 5 or 6, further including one or more heterologous amino acids at the amino terminal end, the carboxy terminal end, or both amino terminal and carboxy terminal ends. The one or more heterologous amino acids can include a cysteine residue at one or more N-terminal ends, a valine residue at one or more C-terminal ends, or a combination thereof.

Embodiment 8 is the multimer of Embodiments 1 to 4 or the isolated peptide of Embodiment 5 to 7, wherein the multimer or isolated peptide includes at least one covalently attached antigen, such as a reduced immunogenicity antigen. A reduced immunogenicity antigen can include carbohydrate, such as a capsular polysaccharide. Examples of capsular polysaccharide include, but are not limited to, a *S. pneumoniae* polysaccharide, such as serotype 2, 3, 4, 5, 6A, 6B, 6C, 6D, 7A, 7F, 8, 9N, 10A, 12F, 13, 14, 15A, 15A, 15F, 17A, 17F, 19A, 19C, 19F, 22F, 32A, 32F, 33A, 33B, 33C, 33D, 33F, 35A, 37, 39, and 42; *Neisseria meningitidis* serogroup Y; *N. meningitidis* serogroup W135; *S. agalactiae* type II; *S. agalactiae* type IV; *Shigella flexneri* serotype D1; *Shigella flexneri* serotype B4; *Shigella flexneri* serotype B5; *Shigella flexneri* serotype B14; *Shigella flexneri* serotype D3; *Shigella flexneri* serotype 0164; *Shigella flexneri* serotype 040; *Shigella flexneri* serotype D11; *Shigella flexneri* serotype D13; *Shigella flexneri* serotype X; *Shigella flexneri* serotype Xv; and *Shigella flexneri* serotype 2A LPS.

Embodiment 9 is a composition that includes the multimer of Embodiments 1 to 4 and 8, or the isolated peptide of Embodiment 5 to 8. The composition can include a pharmaceutically acceptable carrier, and can optionally include an adjuvant.

Embodiment 10 is a method for increasing the antigenicity of a compound, and includes attaching the multimer of Embodiment 1 to 4 or 8, the isolated peptide of Embodiment 5 to 8, or the multimer or isolated peptide of the composition of Embodiment 9 to an antigen, such as a reduced immunogenicity antigen. A reduced immunogenicity antigen can include carbohydrate, such as a capsular polysaccharide. Examples of capsular polysaccharide include, but are not limited to, a *S. pneumoniae* polysaccharide, such as serotype 2, 3, 4, 5, 6A, 6B, 6C, 6D, 7A, 7F, 8, 9N, 10A, 12F, 13, 14, 15A, 15A, 15F, 17A, 17F, 19A, 19C, 19F, 22F, 32A, 32F, 33A, 33B, 33C, 33D, 33F, 35A, 37, 39, and 42; *Neisseria meningitidis* serogroup Y; *N. meningitidis* serogroup W135; *S. agalactiae* type II; *S. agalactiae* type IV; *Shigella flexneri* serotype D1; *Shigella flexneri* serotype B4; *Shigella flexneri* serotype B5; *Shigella flexneri* serotype B14; *Shigella flexneri* serotype D3; *Shigella flexneri* serotype O164; *Shigella flexneri* serotype 040; *Shigella flexneri* serotype D11;

*Shigella flexneri* serotype D13; *Shigella flexneri* serotype X; *Shigella flexneri* serotype Xv; and *Shigella flexneri* serotype 2A LPS.

Embodiment 11 is the method of Embodiment 10, where the antigen is a polysaccharide, and wherein the attaching includes (i) exposing the polysaccharide to a galactose oxidase under conditions suitable for oxidizing the polysaccharide, and (ii) combining the oxidized polysaccharide and the multimer or the isolated peptide under conditions suitable for conjugating the oxidized polysaccharide to the multimer or the isolated peptide. The polysaccharide can include one or more terminal galactose residues, one or more terminal glucose residues, one or more terminal n-acetylglucosamine residues, one or more terminal mannose residues, one or more terminal n-acetylmannosamine residues, or a combination thereof.

Embodiment 12 is a method for inducing an immune response in a subject, and includes administering to the subject the multimer of Embodiment 1 to 4, or 8, the isolated peptide of Embodiment 5 to 8, or the composition of Embodiment 9, wherein the multimer or the isolated peptide includes an antigen, such as a reduced immunogenicity antigen. A reduced immunogenicity antigen can include carbohydrate, such as a capsular polysaccharide. Examples of capsular polysaccharide include, but are not limited to, a *S. pneumoniae* polysaccharide, such as serotype 2, 3, 4, 5, 6A, 6B, 6C, 6D, 7A, 7F, 8, 9N, 10A, 12F, 13, 14, 15A, 15A, 15F, 17A, 17F, 19A, 19C, 19F, 22F, 32A, 32F, 33A, 33B, 33C, 33D, 33F, 35A, 37, 39, and 42; *Neisseria meningitidis* serogroup Y; *N. meningitidis* serogroup W135; *S. agalactiae* type II; *S. agalactiae* type IV; *Shigella flexneri* serotype D1; *Shigella flexneri* serotype B4; *Shigella flexneri* serotype B5; *Shigella flexneri* serotype B14; *Shigella flexneri* serotype D3; *Shigella flexneri* serotype 0164; *Shigella flexneri* serotype 040; *Shigella flexneri* serotype D11; *Shigella flexneri* serotype D13; *Shigella flexneri* serotype X; *Shigella flexneri* serotype Xv; and *Shigella flexneri* serotype 2A LPS. The immune response can include an antibody response to the antigen or a T cell response.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

Isolation and Characterization of New Human CD4+ T Cell Epitopes from Two Important Vaccine Immunogens In the preparation of conjugate vaccines in clinical practice, two highly immunogenic carrier proteins, $CRM_{197}$ and tetanus toxoid (TT), are predominantly used to conjugate with the capsular polysaccharides (CPSs) of bacterial pathogens. In addition, TT has long been used as an effective vaccine to prevent tetanus. While these carrier proteins play an important role in immunogenicity and vaccine design alike, their defined human major histocompatibility complex class II (MHCII) T cell epitopes are inadequately characterized. In this current work, we use mass spectrometry to identify the peptides from these carrier proteins that are naturally processed and presented by human B cells via MHCII pathway. The MHCII-presented peptides are screened for their T cell stimulation using primary CD4+ T cells from four healthy adult donors. These combined methods reveal a subset of eleven CD4+ T cell epitopes that proliferate and stimulate human T cells with diverse MHCII allelic repertoire. Six of these peptides stand out as potential immunodominant epitopes by responding in three or more donors. Additionally, we provide evidence of these new natural epitopes eliciting more significant T cell responses in donors than previously published synthetic peptides selected from T cell epitope screening. This study serves toward understanding carrier protein immune responses and aids in developing novel knowledge-based vaccines to combat persisting problems in conjugate vaccine design.

Introduction

The introduction of conjugate vaccines to clinical practice in the late 80s has led to great strides in combating infections against bacterial pathogens (1-4). Conjugate vaccines against a number of highly infective serotypes of *S. pneumoniae, H. influenzae* type b, and *N. meningitidis* are currently available (3). These vaccines are composed of the bacterial capsular polysaccharide (CPS) covalently conjugated to a carrier protein. The most common carrier proteins include tetanus toxoid (TT) and a non-toxic mutant of diphtheria toxin, $CRM_{197}$ (1, 3). Surprisingly, while these carrier proteins play a prominent role in conjugate vaccine design, the precise nature of their major histocompatibility complex class II (MHCII) epitopes has not been extensively studied.

Upon administration, vaccine components are endocytosed by antigen presenting cells (APCs) processed into smaller peptide fragments that bind with MHCII (5-7). This allows the processed peptide epitopes to be shuttled to the APCs surface to interact with T cell receptors (TCR) of CD4+ helper T cells. There are two working models for how glycoconjugate vaccines induce CD4+ T cell stimulation. According to the first model, when the polysaccharide portion of the conjugate vaccine is not fully degraded in the endolysosomes, a peptide-bound, processed carbohydrate T cell epitope is presented on the surface of APCs (8-10). In the second model, the polysaccharide portion of the glycoconjugate is fully degraded in the endolysosomes and the free peptide is presented on the APCs surface (10). Both models require processing of the carrier protein into MHCII-binding peptides with or without a covalently bound, processed glycan for T cell presentation (11-13). This in turn stimulates the T cells to help B cells produce high-affinity IgG antibodies against the CPS (8). Thus, it is evident that the immunogenicity of the given conjugate vaccine is dependent upon the endosomal processing of conjugate vaccine to yield peptide-containing epitopes that bind to a wide variety of MHCII alleles for T cell stimulation (14). The trimolecular complex, consisting of TCR, MHCII, and the epitope are crucial for immune activation and therefore our understanding of the immune responses elicited by conjugate vaccines.

The intimate knowledge of the nature of the trimolecular complex can then be exploited for the production of knowledge-based, new-generation conjugate vaccines. Due to their empirical design and synthesis, current conjugate vaccines have variable immunogenicity, especially in high-risk populations, such as elderly and immunocompromised individuals (2, 15). Carrier-specific suppression wherein antibody response to the polysaccharide portion of the conjugate vaccine can be inhibited due to pre-existing immune response to the carrier protein from prior immunizations is also a rising concern (16-19). Carrier-specific suppression may be contributing to lowered immunogenicity and efficacy of conjugate vaccines as continued exposure to the same carrier proteins continues to rise with generation of new vaccines. Carrier-specific suppression stems, in part, from the presence of carrier-specific B cells and suppressor T cells (18). Therefore, one approach to eliminate this is the identification of immunogenic peptide epitopes with T cell helper function as has been the focus of multiple studies (16-18).

Importantly, the advantage of using immunogenic peptide epitopes as carriers for conjugate vaccines over the traditional carrier proteins has been demonstrated in previous studies (8, 19-28). For example, one study showed that the use of a peptide as a carrier led to higher IgG titers against the polysaccharide and greater protection in a survival assay compared to a protein carrier (8). Another study showed that peptide as carrier leads to reduced anti-carrier antibody titers compared to protein carrier, indicating reduced carrier-specific suppression (28). These studies mark an important point in understanding immune activation and mechanism behind conjugate vaccines. Only a very small subset of peptides generated from any protein carrier in the endolysosome will bind to MHC. Implementing the use of MHCII-binding peptides as carriers will lead to effective T cell mediated responses. To date, there have been a number of peptides derived from carrier protein TT for this very task. Some of the more common, often referred to as universal TT epitopes, are P2, P30, and P32 (14, 18, 29-34). Additionally, a subset of peptides has been identified for $CRM_{197}$, although research into T cell epitopes of this carrier protein is less extensive (19-21, 35, 36). While the insights gleaned from these works are significant and important, it remains that these peptides were identified through indirect approaches; namely, prediction softwares or T cell screening of overlapping synthetic peptides spanning the proteins.

In this study, we aimed to identify naturally processed and presented immunogenic peptide epitopes derived from carrier proteins TT and $CRM_{197}$, through immunoprecipitation and mass spectrometry. The identified peptides were then probed for T cell proliferation in four healthy adult donors primed with TT and $CRM_{197}$. We determine peptide epitopes for both carrier proteins, in addition to variants of previously published peptides, which are capable of binding MHCII and stimulating human CD4+ T cells. Additionally, we present evidence that these defined peptide epitopes discovered through natural MHCII presentation perform better in activating CD4+ T cells than previously reported universal TT epitopes. This information will be valuable for generating peptide-based carriers to be used in future vaccine design.

Material and Methods

Study Subjects

The studies described herein utilized human samples approved by the University of Georgia Institutional Review Board as STUDY00005127. Four adult donors from Athens, GA USA who were vaccinated with PCV13 (Prevnar-13) less than one year prior to their blood collection, and with verbally confirmed Tdap vaccination within the past 10 years were recruited to the University of Georgia Clinical and Translational Research Unit. Participants provided written informed consent for participation in this study. Peripheral blood mononuclear cells (PBMCs) were purified by Ficoll-gradient density centrifugation and were used fresh in all assays.

Affinity Purification of MHCII Molecules

Approximately $5\times10^7$ human B lymphoblasts (Raji ATCC CCL-86) were incubated with 1 mg of carrier protein ($CRM_{197}$ [Fina Biosolutions, LLC], Tetanus toxoid [TT], or TT heavy chain [$TT_{hc}$][Fina Biosolutions, LLC]) in RPMI 1640 (Corning) medium containing 2 g/L sodium bicarbonate, 2 mM L-glutamine, 1 mM sodium pyruvate, 1% penicillin/streptomycin, and 10% heat inactivated FBS. Cells were incubated for 18 hrs at 37 degrees in 5% $CO_2$. After incubation MHCII molecules were obtained via immunoprecipitation after lysis of the cells in NP-40 buffer for 1 hour at room temperature. The lysate was cleared by centrifugation at 15,000×g for 15 minutes. The MHCII molecules were immunoprecipitated from the cleared lysate using 15 ng of each anti-human HLA-DR antibody (L243 Biolegend), HLA-DP antibody (BRAFB6 Santa Cruz Biotechnology), or HLA-DQ antibody (B-K27 Santa Cruz Biotechnology) bound to Protein A agarose beads (Sigma-Aldrich). The affinity column was washed with PBS four times. The MHCII molecules were then eluted from the affinity column with 10% acetic acid at room temperature for 3 minutes with 4 elution fractions collected. Eluted MHCII proteins were evaluated for purity via mass spectrometry. Immunoprecipitation for mass spectrometry analysis was performed three independent times to select the peptide epitopes displayed here.

Separation of Peptides from MHCII Molecules

Eluted MHCII molecules were heated at 70 degrees for 10 minutes to denature MHCII and release bound peptides. Peptides were separated out from denatured HLA protein subunits by ultrafiltration using a 10 kDa cutoff membrane filter (Millipore) at 4000×g. The filter was washed two times using deionized water before loading samples. Recovered peptides in the filtrate were dried down and resuspended in 8M urea in 50 mM ammonium bicarbonate before sonication. Samples were desalted prior to mass spectrometry analysis with ZipTip C-18 columns per product protocol (Millipore). The eluted peptides were diluted to 10% acetonitrile with 0.1% formic acid and spun through a 0.2 μM nylon centrifugal filter (VWR) at 1000×g to remove any precipitants. The retentate fraction containing denatured HLA proteins was dried down and resuspended in 8M urea in 50 mM ammonium bicarbonate containing 10 mM TCEP. Samples were treated with 10 mM iodoacetamide and sonicated. Trypsin (250 ng) was added and the samples were incubated overnight at 37° C. The resulting peptides were desalted on ZipTips as described above.

Analysis by Mass Spectrometry\

The samples were injected onto a PepMap RSLC C18 column (Thermo Scientific) with an Easy nano HPLC coupled to a Q-Exactive Plus mass spectrometry system (Thermo Scientific) at a flow rate of 300 nl/min with a 25 min 0-40% acetonitrile gradient in 0.1% formic acid followed by a 3 min gradient to 80% acetonitrile. Spectra were recorded with a resolution of 35,000 in the positive polarity mode over the range of m/z 350-2,000 and an automatic gain control target value was $1\times10^6$. The 10 most prominent precursor ions in each full scan were isolated for higher energy collisional dissociation-tandem mass spectrometry (HCD-MS/MS) fragmentation with normalized collision energy of 35%, an automatic gain control target of $2\times10^5$, an isolation window of m/z 3.0, dynamic exclusion enabled, and fragment resolution of 17,500.

Database Search

Targeted searches against tetanus toxin protein (Uniprot P04958) and diphtheria toxin protein (Uniprot Q6NK15) were performed by Byonic v (Protein Metrics) software. Non-specific cleavage was selected with a parent ion mass error of 10 ppm and MS2 ion mass error of 20 ppm. Peptides identified after 2% False Discovery Rate were manually evaluated. Byonic scores for positive identifications were greater than 50 but under 100, so spectra with discernable isotopic distributions and few MS2 contaminants were considered. Proteome Discoverer 2.1 was used for Sequest searches against the human proteome (UniProt ID UP000005640) to identify MHCII molecules in retentate fractions.

Synthesis of Discovered Peptides

We synthesized 11 peptides that were observed through mass spectrometry analysis. Peptides were derived from either $CRM_{197}$ or tetanus toxoid (TT) proteins. Additionally, we synthesized two "universal" CD4+ cell epitopes of TT, P2 and P32. Sequences and protein positions of peptides can be found in Table 1. All couplings for peptides were carried out on an automated microwave-assisted solid-phase peptide synthesizer (CEM Corp. Liberty microwave synthesizer) using the standard protocols in the instrument software. Peptides were synthesized on Rink amide resin (0.6 meq/g; Novabiochem) via $N^R$—N-(9-fluorenyl) methoxycarbonyl (Fmoc) approach in the primary solvent N,N-dimethylformamide (DMF). 20% 4-methylpiperidine in DMF was used for Fmoc removal. 2-(1H-Benzotriazole-1-yl)-oxy-1,1,3,3-tetramethyluronium hexafluorophosphate/1-hydroxybenzotriazole in the presence of N,N-diisopropylethylamine (DIPEA) were used as the coupling reagents. Peptides were cleaved from the resin through TFA/triisopropylsilane/$H_2O$ (95:2.5:2.5) cocktail for ~2 hours. The cleavage cocktail was added dropwise through a filter to cold ether to precipitate the crude peptide and centrifuged to remove the ether supernatant. Purity was verified by analytical HPLC and MALDI-TOF MS.

with 2 μg/mL protein ($CRM_{197}$, $TT_m$, $TT_{hc}$, or BSA as negative control). Wells were blocked with 1% BSA in PBS and washed with 0.05% PBS-Tween (PBST) all subsequent washes were the same. Serial dilutions of donor serum starting at 1:200 was added to wells for 2 hours at room temperature and washed. Total IgG titers were detected by HRP conjugated anti-human IgG (Santa Cruz Biotechnology) (1:2000 dilution) added to wells for 2 hours at room temperature. After washing, plates were developed using 3,3,5,5' tetramethyl benzidine (TMB) substrate (Biolegend) and stopped with 2 N $H_2SO_4$. The optical densities were determined at 450 nm using a microplate reader (Synergy H1, Bio-Tek). Serum titers were determined at OD 0.5 and significance determined using 2-tailed Student's t test with $p<0.05$.

MHCII Binding Assays

MHCII binding was assessed using an ELISA based assay as previously described (37). Approximately $1\times10^7$ Raji cells or MHCII-deficient Raji derived RJ2.2.5 cells were plated per well in 3 mL supplemented RPMI medium in a 6-well plate. Cells were incubated with 100 ug of biotinylated peptides ($CRM_{299-312}$ or $TT_{1093-1102}$) in RPMI 1640 (Corning) medium containing 2 mM L-glutamine, 1% penicillin/streptomycin, and 10% heat inactivated FBS. After 18 hrs incubation at 37 degrees, cells were lysed in NP-40 buffer for 1 hour at room temperature. The lysate was cleared by centrifugation at 15,000×g for 15 minutes. ELISA assay was performed to detect the presence of MHCII bound biotinylated peptides. Briefly, 96-well plates (Costar) were coated in duplicate overnight with 5 μg/mL L243 anti-HLA-DR (Biolegend). Wells were blocked with 1% BSA in PBS and washed with 0.05% PBS-Tween (PBST). Whole cell lysates were incubated for 1 hour at

TABLE 1

List of peptides identified through LC-MS/MS analysis of MHCII immunoprecipitation. Table lists the peptide sequences identified from B cells treated with carrier protein and the amino acid residues at which they occur, the MHCII isotype used for their pulldown, and the calculated and observed parent ion masses (all masses converted to singly charged M+H+ m/z) from mass spectra.

| Peptide | Sequence | Observed in Isotypes | Parent ion $[M + H]^+$ | Predicted $[M + H]^+$ |
|---|---|---|---|---|
| $TT_{94-107}$ | LFNRIKNNVAGEAL | DR | 1558.881 | 1558.870 |
| $TT_{660-667}$ | NFIGALET | DR | 864.454 | 864.446 |
| $TT_{825-837}$ | NILMQYIKANSK | DR | 1294.704 | 1294.682 |
| $TT_{1093-1102}$ | CKALNPKEIE | DR, DQ | 1144.596 | 1144.603 |
| $TT_{1169-1179}$ | LYNGLKFIIKR | DR | 1364.850 | 1364.841 |
| $TT_{1222-1236}$ | DRILRVGYNAPGIPL | DR | 1653.943 | 1653.943 |
| $TT_{1228-1239}$ | GYNAPGIPLYKK | DQ | 1320.733 | 1320.731 |
| $CRM_{26-39}$ | GYVDSIQKGIQKPK | DR | 1560.873 | 1560.874 |
| $CRM_{87-97}$ | GLTKVLALKVD | DR | 1156.723 | 1156.730 |
| $CRM_{299-312}$ | KTTAALSILPGIGS | DR, DP, DQ | 1328.778 | 1328.787 |
| $CRM_{425-440}$ | TPLPIAGVLLPTIPGK | DR, DQ | 1586.984 | 1586.988 |

ELISA of Donor Serum

Anti-carrier protein IgG titers were determined using enzyme-linked immunosorbent assay (ELISA). Briefly, 96-well plates (Costar) were coated in duplicate overnight room temperature. Presence of MHCII bound biotinylated peptide was detected by adding HRP conjugated Avidin (Biolegend) (1:1000 dilution) for 1 hour at room temperature. After washing, plates were developed using TMB (Biolegend) and stopped with 2 N $H_2SO_4$. The optical densities were determined at 450 nm using a microplate reader (Synergy $H_1$, Bio-Tek). Significance was determined using 2-tailed Student's/test with $p<0.05$ comparing no antigen negative control wells to experimental cell groups incubated with biotinylated peptides.

T Cell Proliferation

PBMCs were collected freshly from healthy donors and separated using Ficoll extraction. The culture medium for the PBMCs was RPMI 1640 (Corning) supplemented with 2 g/L sodium bicarbonate, 50 UM 2-mercaptoethanol, 2 mM L-glutamine, 1 mM sodium pyruvate, 1% nonessential amino acids, 1% penicillin/streptomycin, and 10% heat inactivated FBS. CD4+ T cells were separated out from PBMCs using a negative selection CD4 enrichment kit (BD Biosciences) and stained with 2 μM carboxyfluorescein diacetate succinimidyl ester (CFSE). CD4-depleted PBMCs were treated with mitomycin-C at 25 μg/mL. Proliferation assays were performed with CFSE stained CD4+ T cells using $10^5$ cells/well and mitomycin-C treated PBMCs ($2\times10^5$ cells/well) as APCs. Cells were plated in quadruplicate per antigen in 200 μL supplemented RPMI in 96-well flat bottom plate. Cells were stimulated with 2.5 ng/mL IL-2 and each of the following antigens at 50 μg/ml: $CRM_{197}$ protein (Fina Biosolutions, LLC), $TT_{hc}$ protein (Fina Biosolutions, LLC), $TT_m$, P2, P32, $TT_{94-107}$, $TT_{660-667}$, $TT_{826-837}$, $TT_{1093-1102}$, $TT_{1169-1179}$, $TT_{1222-1236}$, $TT_{1228-1239}$, $CRM_{26-39}$, $CRM_{87-97}$, $CRM_{299-312}$, and $CRM_{425-440}$. After 72 hours cells were supplemented with 2.5 ng/ml IL-2 and 50 μg/ml antigen in 50 μL supplemented RPMI media. Cells were harvested after 6 days for proliferation assessment. The extent of proliferation was measured by CFSE depletion among CD4+ T cells using anti-human CD4 antibody (Biolegend) in flow cytometry analysis (CytoFLEX, Beckman Coulter). Proliferating cells were gated as CFSE− in CD4+ populations. Basal growth rate was determined from quadruplicate wells that contained CD4+ cell enriched PBMCs without stimuli.

To determine whether the T cell response is dependent on antigen processing and presentation, T cell proliferation was performed using 2% paraformaldehyde-fixed APCs compared to mitomycin-C treated APCs. The following antigens were used in the T cell stimulation: $CRM_{299-312}$ or $TT_{1093-1102}$. To determine significance of depleted CFSE populations in response to antigen compared to the basal growth rate, we used 2-tailed Student's t test. A p value of $<0.05$ was considered to be statistically significant.

IFN-γ Cytokine ELISA

Cytokine production from T cell stimulation was determined by ELISA. 96-well plates (Costar) were coated overnight with anti-IFN-γ antibody (1:200 dilution; Biolegend) and blocked with 1% BSA in PBS. Plates were washed with 0.05% PBST, all subsequent washes were the same. After washing, wells were incubated with cell supernatants from T cell assays for 2 hours at room temperature. After washing, biotinylated anti-IFN-γ (1:200 dilution; Biolegend) was added for 1 hour at room temperature followed by HRP-Avidin (1:1000 dilution; Biolegend) for 30 minutes at room temperature. Plates were developed using TMB substrate (Biolegend) and stopped with 2 N $H_2SO_4$. The optical densities were determined at 450 nm using a microplate reader (Synergy $H_1$, Bio-Tek). Significance was determined using Student's/test with $p<0.05$.

HLA Locus Genotyping of Donors

HLA typing of each donor was performed by CD Genomics. Alleles of DPA1, DPB1, DQA1, DQB1, DRB1, and DR345 locus were genotyped for each donor.

Results

Immunoprecipitation to Pulldown Peptide-Loaded MHCII Proteins

To identify peptides generated through processing of $CRM_{197}$, $TT_m$, or $TT_{hc}$ by human APCs and presented by MHCII, we adapted previously described methods of immunoprecipitation (IP) and mass spectrometry (38-41) (FIG. 1). We utilized a human B cell lymphoblast line, Raji cells (ATCC CCL-86) as APCs and incubated with either $CRM_{197}$, $TT_m$, or $TT_{hc}$. The use of two TT proteins, $TT_m$ (full protein: light chain and heavy chain) and TT heavy chain ($TT_{hc}$) was to assess if T-ell epitopes existed in the light chain of the protein as the majority of reported T cell epitopes are in the heavy chain (42). Raji cells are known to express multiple alleles of –DRB1 and B3, –DPB1, and –DQA1 and B1 (43). To observe a full spectrum of peptides presented via Raji MHCII proteins, we used antibodies against all three isotypes of MHCII, HLA-DR-DP and –DQ (FIG. 1). Mass spectrometry analysis of the retentate revealed that we were able to successfully pull down each isotype of MHCII protein selectively with little cross contamination between isotypes (FIG. 2). Elution fractions were heated to dissociate the MHCII protein into releasing the bound peptides, which were then separated using ultrafiltration. Importantly, mass spectrometry confirmed the presence of MHCII in the cutoff column retentate and absence in the filtrate, which contained the eluted peptides. Taken together, these results indicate the IP protocol is efficiently pulling down each isotype of MHCII proteins with few contaminants or isotype crossover.

Mass Spectrometry Analysis Reveals a Subset of New MHCII Binding Peptides

To determine the identity of the eluted peptides from each MHCII IP, we used LC-MS/MS (FIG. 1). Mass spectral analysis of eluted peptide pools revealed a set of eleven MHCII binding peptides from either TT or $CRM_{197}$ of varying lengths naturally presented via MHCII from human APCs (Table 1). The majority of peptides were discovered through HLA-DR IP. Four peptides were isolated from HLA-DQ IP, and only one from HLA-DP IP. Three of the peptides were observed in IP with multiple alleles (Table 1). We found the average length of peptide epitopes from TT processing and presentation to be 12 residues, with peptides ranging from 8-15 residues. Peptides found for $CRM_{197}$, on the other hand, had an average length of 14 residues, ranging from 11-16 amino acids (Table 1). We found two peptides ($TT_{826-837}$ and $TT_{1169-1179}$) that shared overlapping sequences with known "universal" TT peptides P2 (QYIKANSKFIGITEL, SEQ ID NO:14) and P32 (LKFIIKRYTPNNEIDS, SEQ ID NO:19) respectively (14). $TT_{826-837}$ shares 8 amino acid residues with P2 at the N-terminus of P2. Similarly, $TT_{1169-1179}$ shares 7 residues with P32 at the N-terminus of P32. Additionally, we observed one peptide from the TT light chain $TT_{94-107}$. To our best knowledge, none of these peptides have been reported previously with the specific amino acid sequences observed here. However, some peptide epitopes described here share overlapping sequences in various degrees with epitopes reported on the Immune Epitope Database and Analysis Resource (IEDB).

Human Donors have IgG Titers Against $CRM_{197}$ and TT

Figure 3:
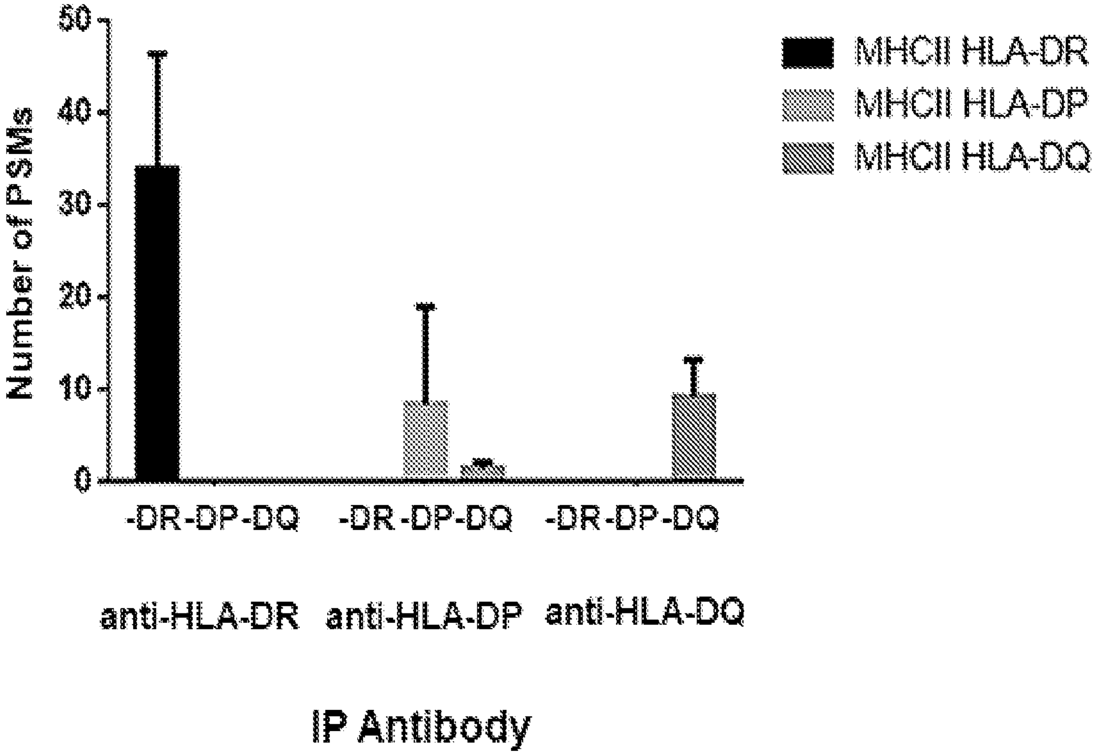
FIG. 3 shows mass spectral analysis of immunoprecipitation products. Identified MHCII proteins in bead bound product from each immunoprecipitated isotype compared via number of peptide spectral matches (PSMs). The data represents the average of number of PSMs from three biological replicates. The error bars are standard deviation.

To determine if these identified peptides were able to stimulate antigen-specific T cell response in a physiological scenario, human PBMCs were utilized. We first screened human sera for reactivity to both carrier proteins used in this study to confirm that each donor had existing IgG titers, therefore responsive B and T cells. Donors were previously immunized with both PCV13 and Tdap. Serum titers against each carrier protein and a negative control of BSA were determined using ELISA (FIG. 3). Serum IgG titers against carrier proteins were significantly higher than negative control BSA for all donors (FIG. 3). The variability in serum titers, particularly for TT proteins compared to $CRM_{197}$, most likely results from timing of vaccination for donors. Donors received PCV13 in the preceding months before this study, but the time of vaccination for Tdap was as early as 10 years prior to the study. These results indicate that the selected donors had significant IgG titers against all three carrier proteins and would be sufficient to study T cell response against identified peptides.

Identified Peptides Bind to MHCII

Figure 4A:
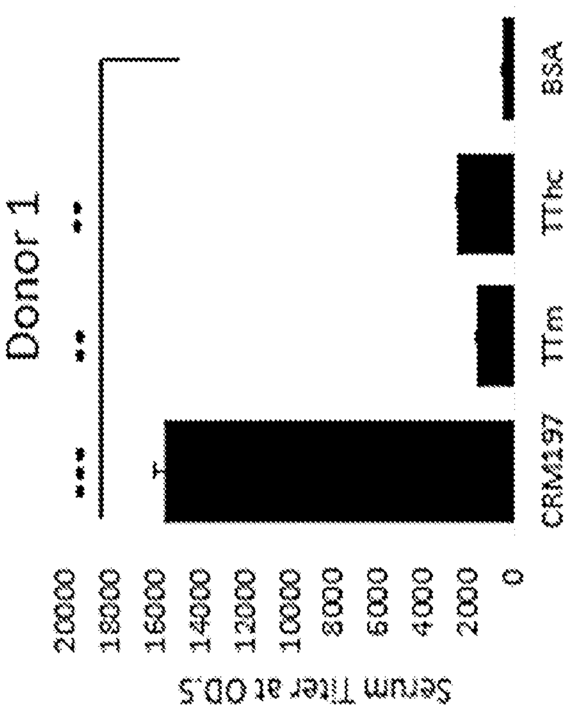
FIGS. 4A-D show serum IgG titers of four human donors. Serum titers are for three carrier proteins $CRM_{197}$, TTm, and TThc. BSA was used as a negative control. Donor 1 (FIG. 4A), Donor 2 (FIG. 4B), Donor 3 (FIG. 4C), and Donor 4 (FIG. 4D) serum titers were determined at OD 0.5. Significance was determined using Student's t test with $p<0.05$.
Figure 4B:
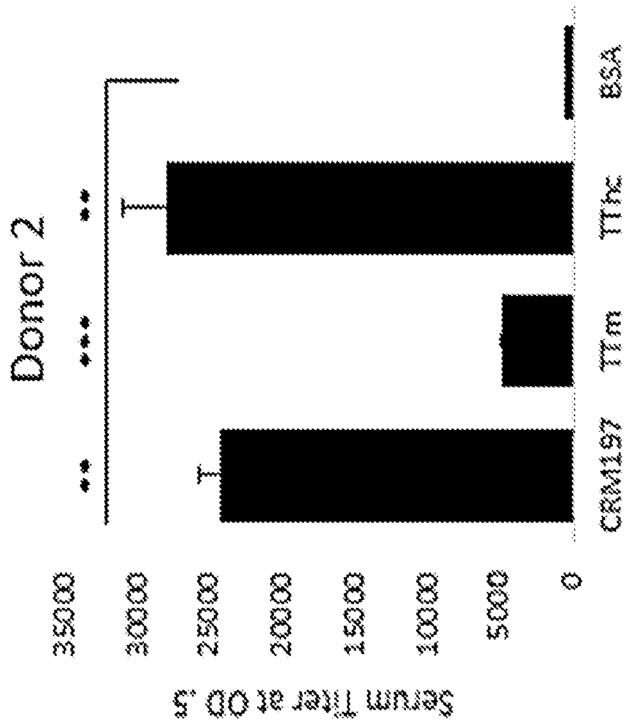

To corroborate immunoprecipitation data on MHCII binding, we performed an ELISA-based in vitro binding assay (FIG. 4) adopting a previously described method (37). One peptide from each TT and CRM subsets was selected and biotinylated for MHCII binding evaluation based on their significant T cell activity (Table 2, FIGS. 5 and 6). Biotinylated peptides were incubated with Raji B cells or MHCII-deficient, Raji-derived RJ2.2.5 B cells and binding was assessed. MHCII-bound biotinylated peptides were pulled down together with MHCII molecules and detected by Avidin-HRP. Compared to no antigen control, both peptides showed a significant binding to MHCII (FIG. 4*a*). Importantly, RJ2.2.5 cells were used as a control of MHCII binding as these B cells lack MHCII expression (FIG. 4*b*). There was no detection of biotinylated peptides bound with MHCII compared to the no antigen negative control when incubated with RJ2.2.5 cells, suggesting a lack of MHCII binding and presentation.

TABLE 2

List of peptides that gave a positive response in at least one donor. Results are shown for CFSE staining and IFN-γ ELISA per donor. Significance was determined using student's t test and is given as * $p < 0.05$  $p < 0.005$ * $p < 0.0005$.

| | Donor 1 | | Donor 2 | | Donor 3 | | Donor 4 | |
|---|---|---|---|---|---|---|---|---|
| | CFSE | IFN-γ | CFSE | IFN-γ | CFSE | IFN-γ | CFSE | IGN-γ |
| P2 | | | | | * | | *** | * |
| P32 | | | *** | ** | ** | ** | *** | * |
| $TT_{94-107}$ | | | *** | ** | *** | ** | ** | * |
| $TT_{550-557}$ | | * | | | ** | * | *** | * |
| $TT_{826-837}$ | | | | | | * | | |
| $TT_{1093-1102}$ | | * | | * | ** | ** | *** | * |
| $TT_{1169-1179}$ | * | | *** | * | * | * | | * |
| $TT_{1222-1236}$ | * | | *** | *** | | | * | |
| $TT_{1228-1239}$ | | | | | ** | ** | *** | ** |
| $CRM_{26-39}$ | * | ** | | ** | * | * | *** | *** |
| $CRM_{57-97}$ | | * | | ** | ** | *** | *** | ** |
| $CRM_{255-312}$ | *** | * | *** | ** | ** | * | *** | ** |
| $CRM_{425-440}$ | | | *** | ** | ** | ** | *** | *** |

Figure 4C:
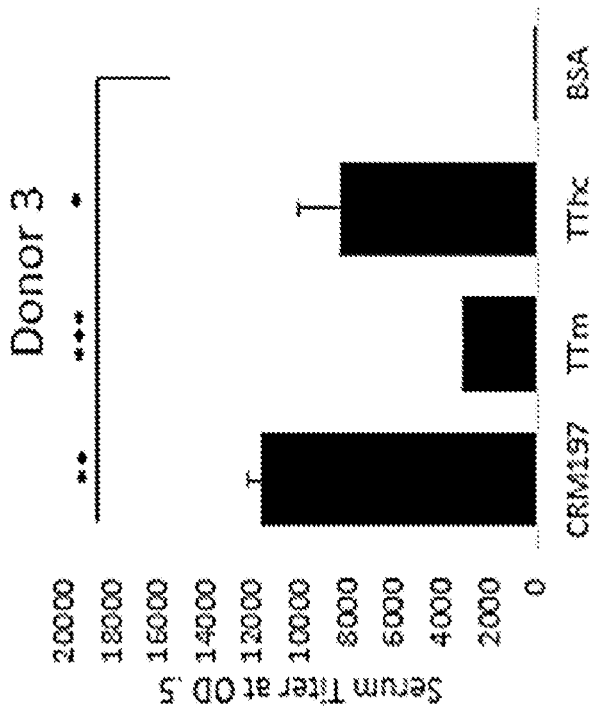
Figure 4D:
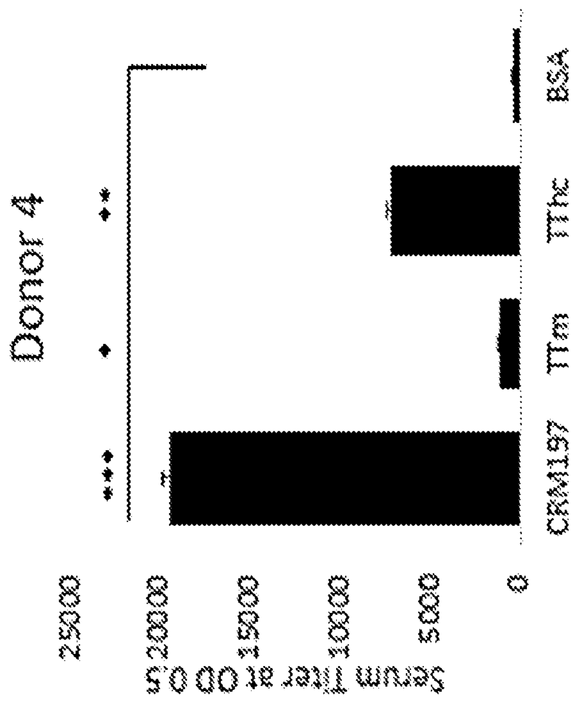
Figure 5A:
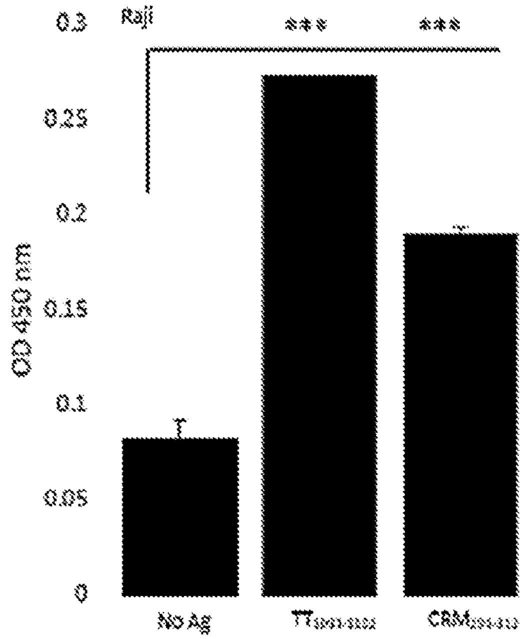
FIGS. 5A-C show MHCII presentation of peptides for T cell recognition. Raji B (FIG. 5A) or RJ2.2.5 cells (FIG. 5B) were incubated with biotinylated peptides. Whole cell lysates were incubated on L243 anti-HLA-DR (Biolegend) coated ELISA plates and binding to MHCII was measured by Avidin-HRP.

Lastly, we tested whether T cell response stimulated by these peptides are dependent on antigen uptake, processing and presentation via MHCII in APCs (FIG. 4*c*). Donor PBMCs were separated for CD4+ T cells and APCs. A subset of APCs was treated with paraformaldehyde for fixation and inhibition of antigen processing and presentation. With unfixed APCs, both peptides stimulated donor T cell proliferation. However, peptides in fixed APCs group were unable to stimulate T cells (FIG. 4*c*). Taken together this data further supports that selected peptides bind to MHCII and these peptides are processed and presented via MHCII in APCs to stimulate T cell response.

Identified Peptides are Able to Stimulate Donor CD4+ T Cell Response

Figure 5B:
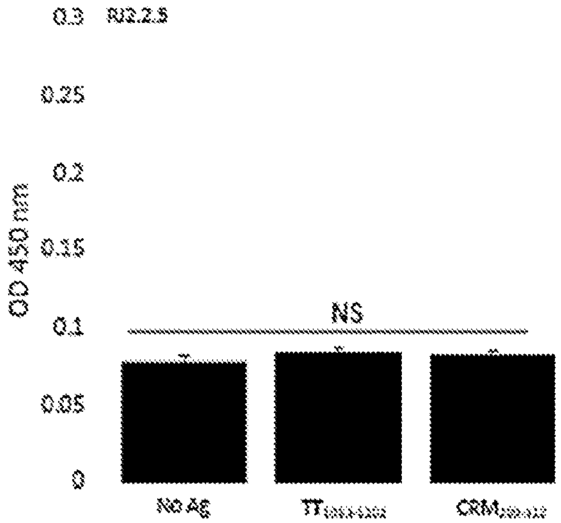
Figure 5C:
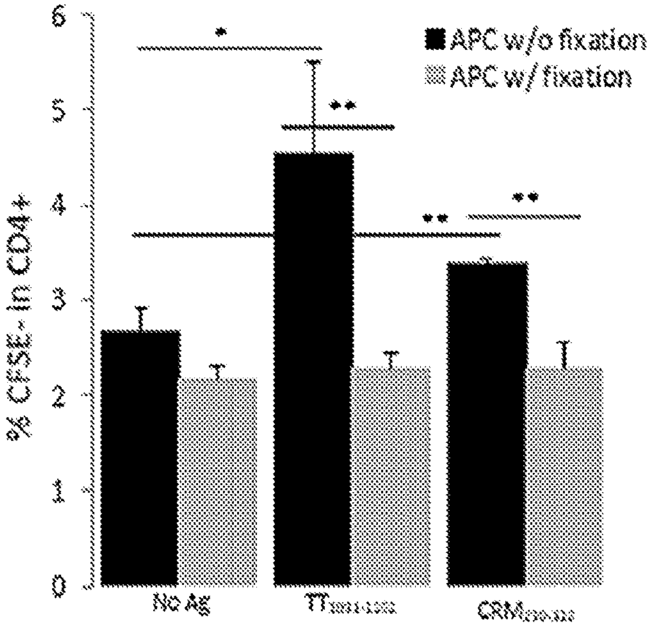
Figure 6A:
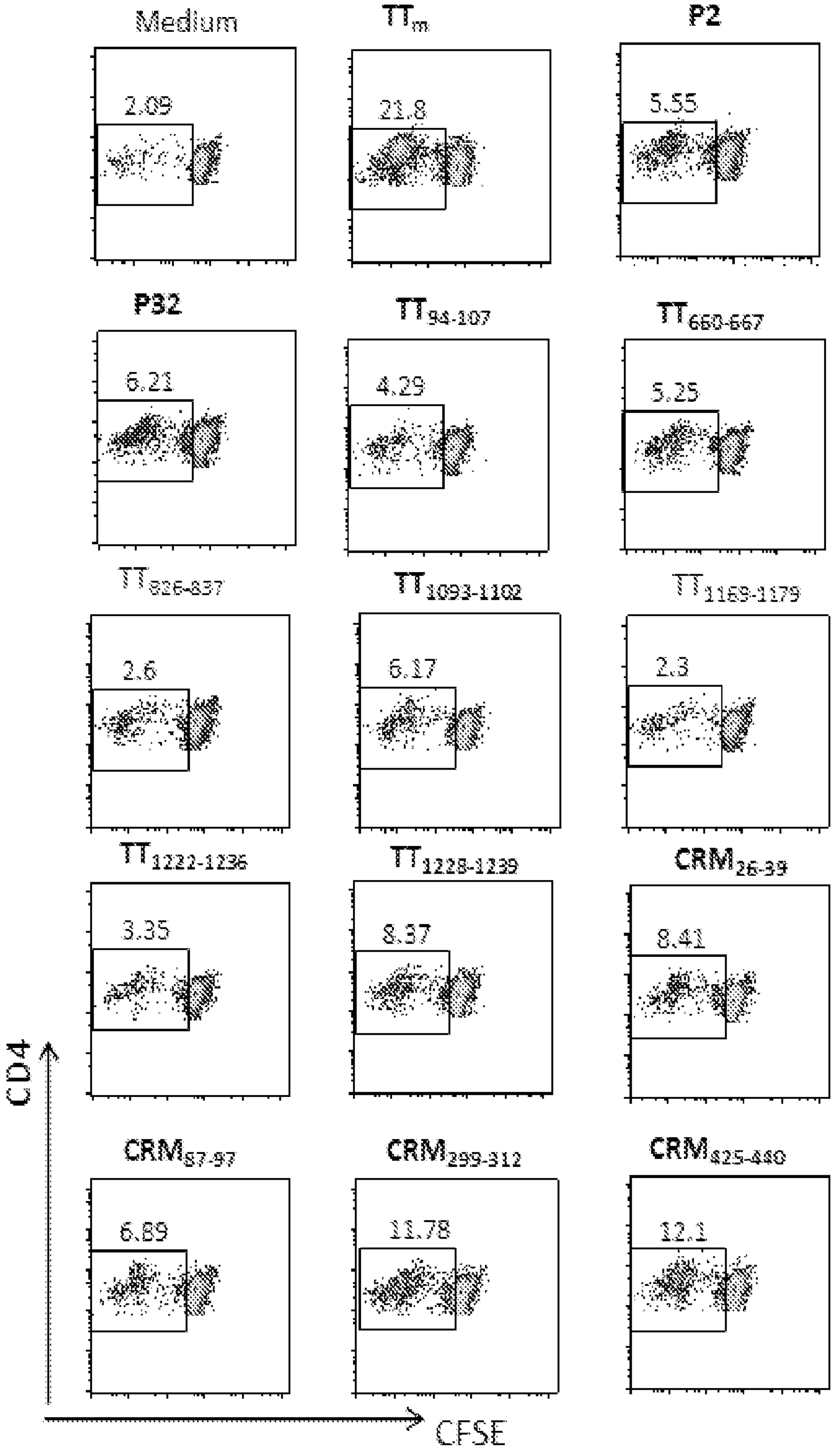
FIGS. 6A-E show proliferation of CD4+ enriched PBMCs from four donors. Donor 4 (FIG. 6A) gating of CD4+ cells with CFSE− populations squared off. CFSE responsive peptide stimulations are bold. TTm is shown as positive control and medium as negative. % CFSE− in CD4+ for Donor 1 (FIG. 6B), Donor 2 (FIG. 6C), Donor 3 (FIG. 6D), and Donor 4 (FIG. 6E). PBMCs were enriched for CD4+ T cells and APCs then incubated with respective antigen supplemented with IL-2. Proliferation was measured by gating CD4+ T cells and measuring percent of CFSE− in CD4+ populations. Student's t test was performed for statistical value with $p<0.05$.
Figure 6B:
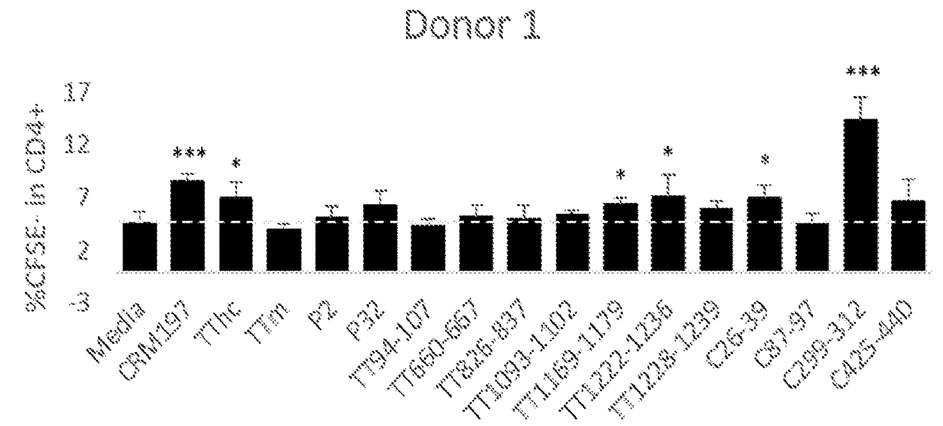
Figure 6C:
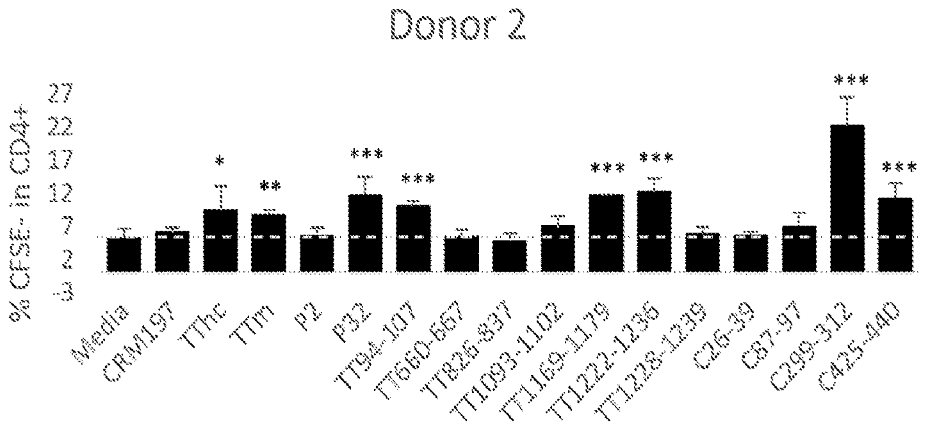
Figure 6D:
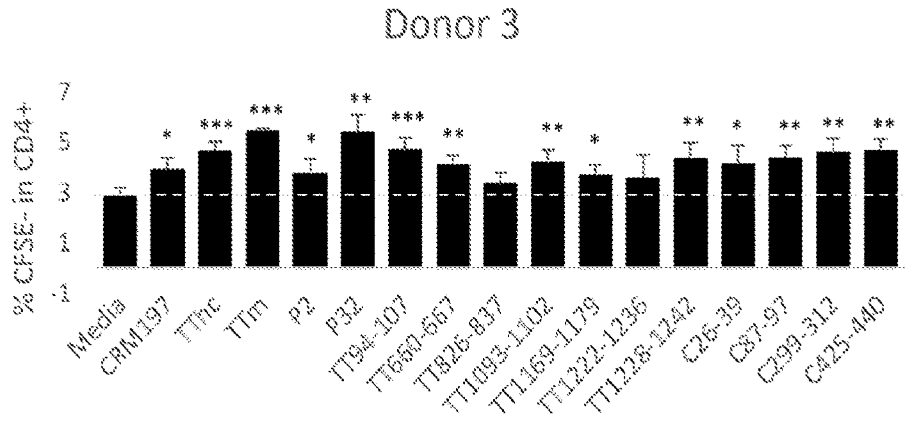
Figure 6E:
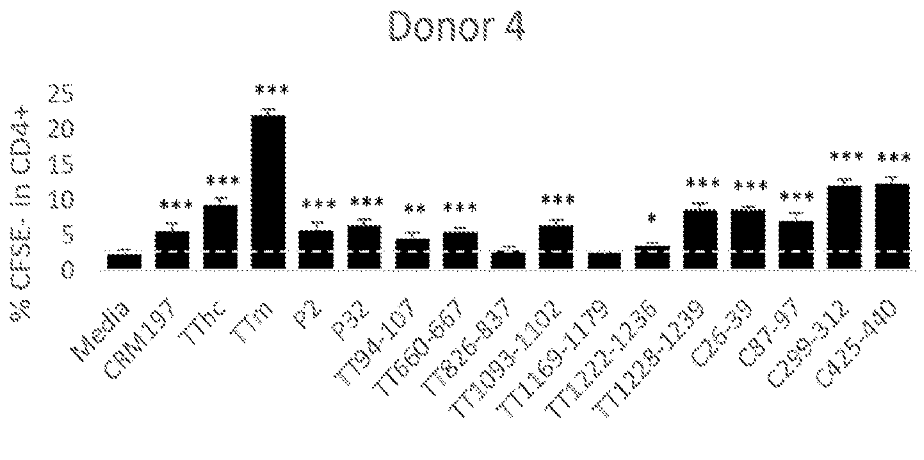
Figure 7A:
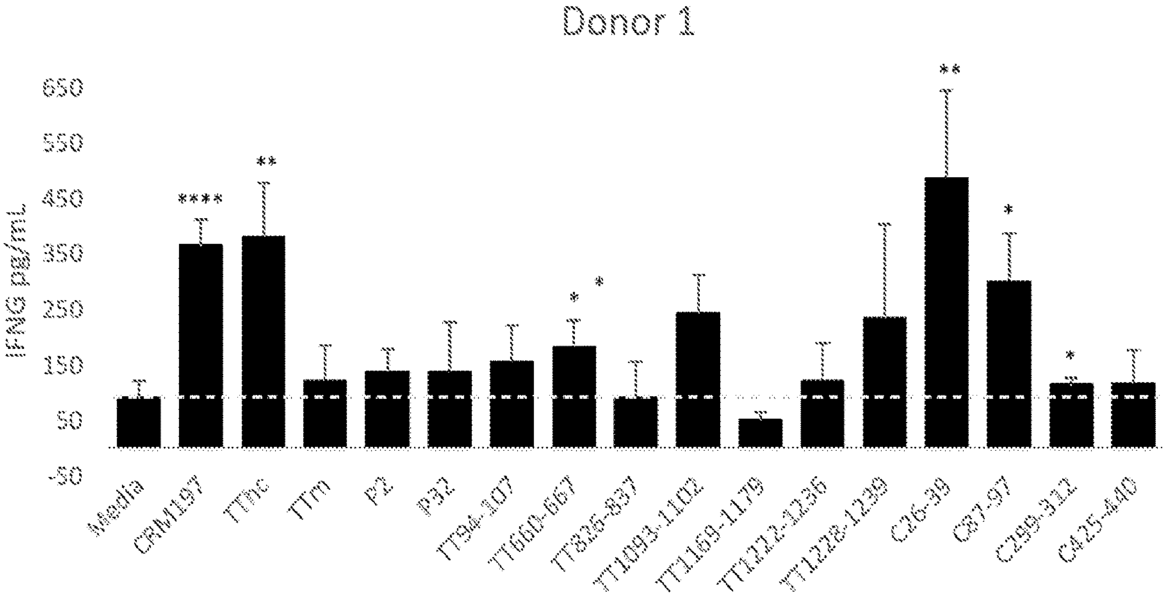
FIGS. 7A-D show IFN-γ cytokine secretion of human PBMCs from four donors. Donor 1 (FIG. 7A), Donor 2 (FIG. 7B), Donor 3 (FIG. 7C), Donor 4 (FIG. 7D). PBMCs were enriched for CD4+ T cells and APCs then incubated with respective antigen supplemented with IL-2. Cytokine secretion was measured using ELISA assay and output was converted to product formed in pg/mL using IFN-γ human standards. Student's t test was performed for statistical value against media blank with $p<0.05$.
Figure 7B:
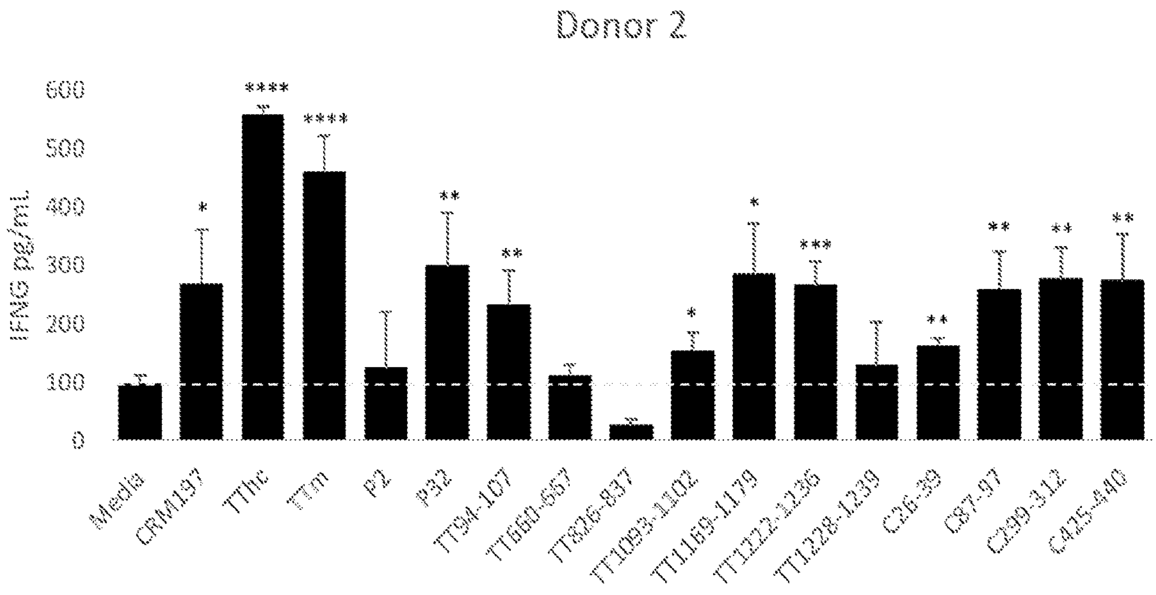
Figure 7C:
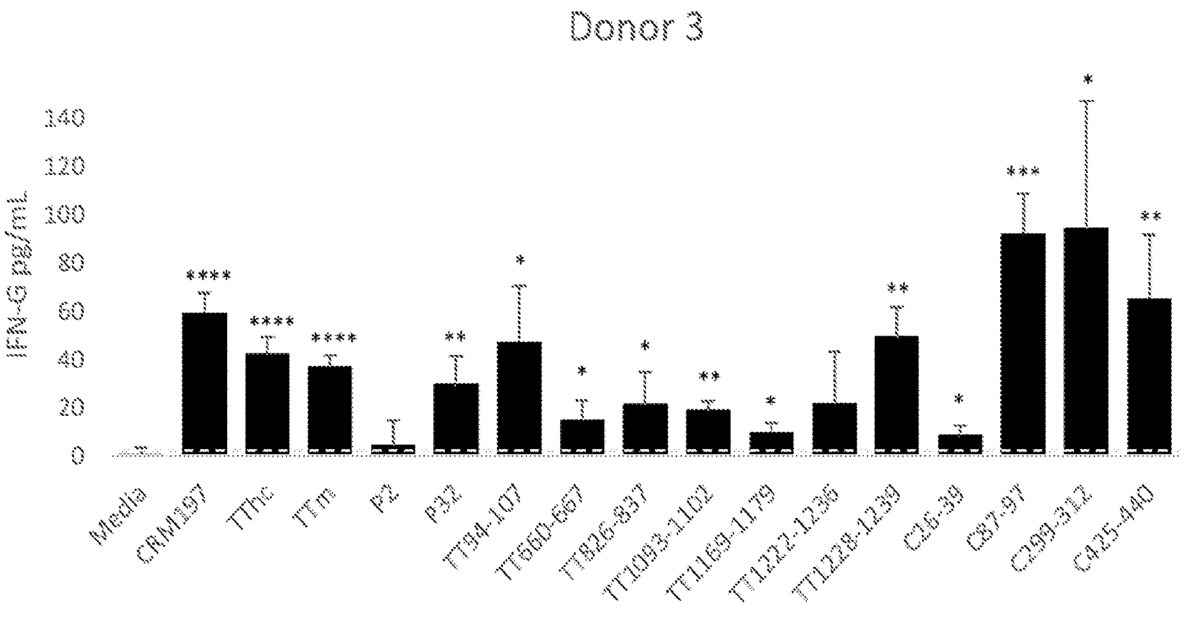
Figure 7D:
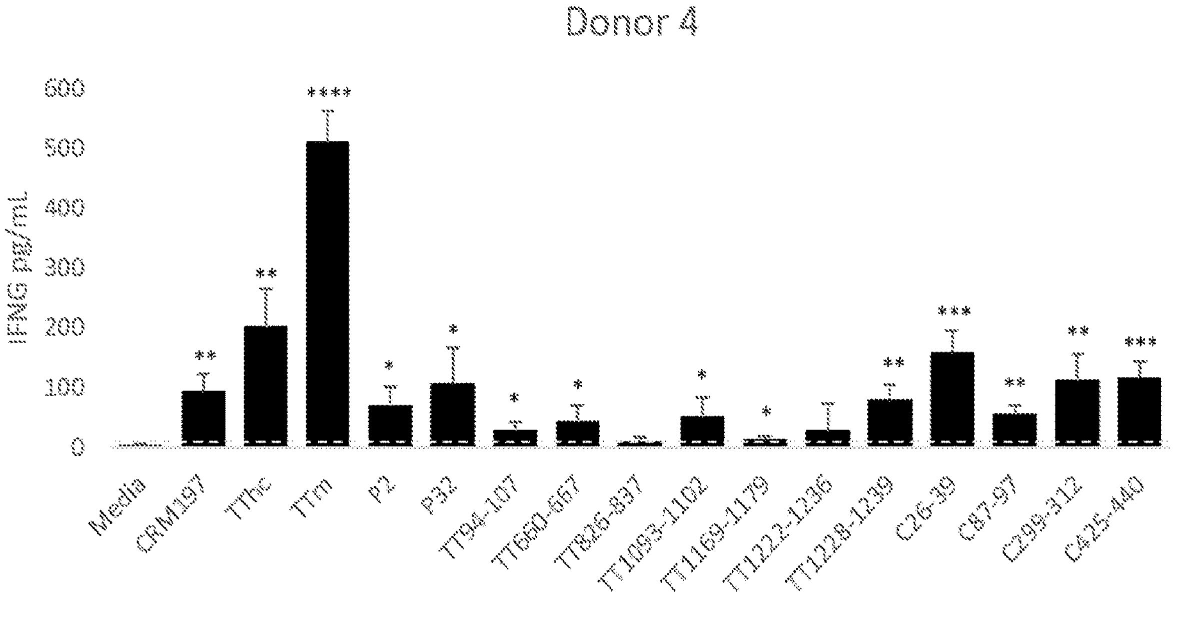
Figure 8A:
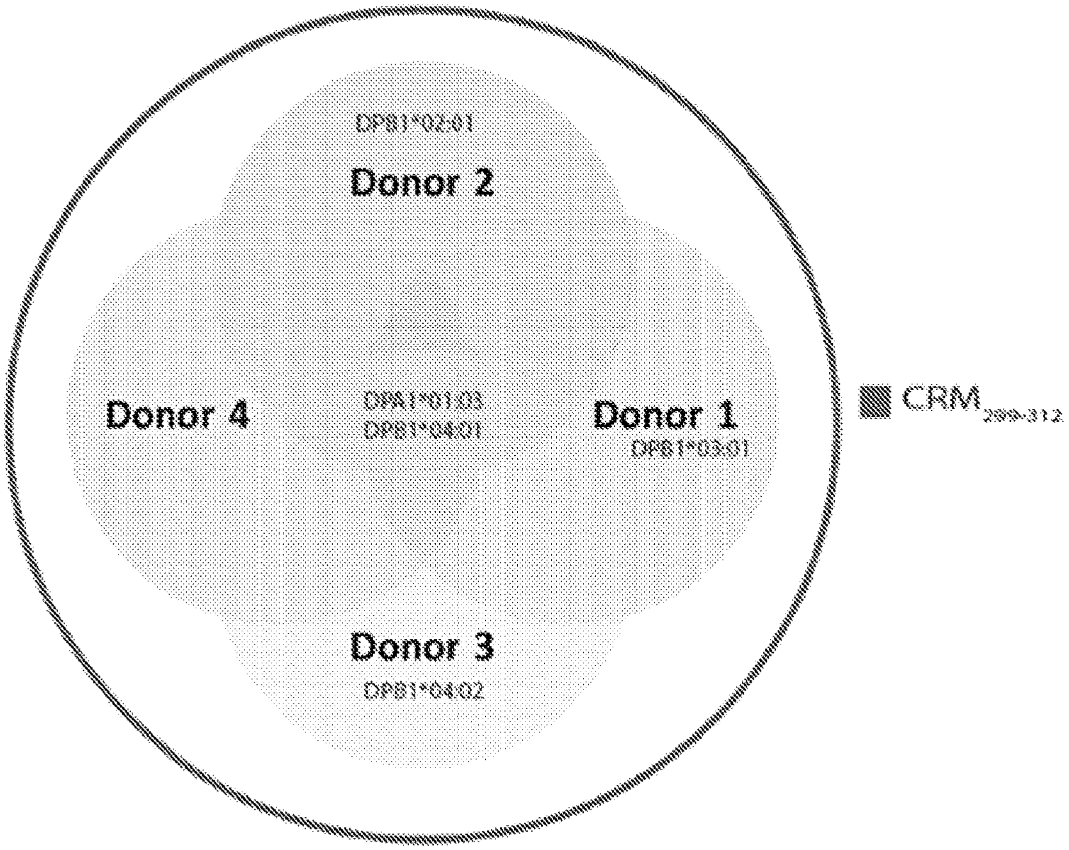
FIGS. 8A-C show a three-tier comparison of the class II alleles expressed in each donor for each isotype of MHCII and the peptides presented by that isotype. Venn diagram depicts comparison of class II alleles expressed in each donor for DP (FIG. 8A), DQ (FIG. 8B) and DR (FIG. 8C) isotypes of MHCII. The outer colored lines represent the peptides that were identified via mass spectrometry for that isotype of MHCII. These lines surround the donors which had a positive T cell proliferative response (as determined by CFSE staining).
Figure 8B:
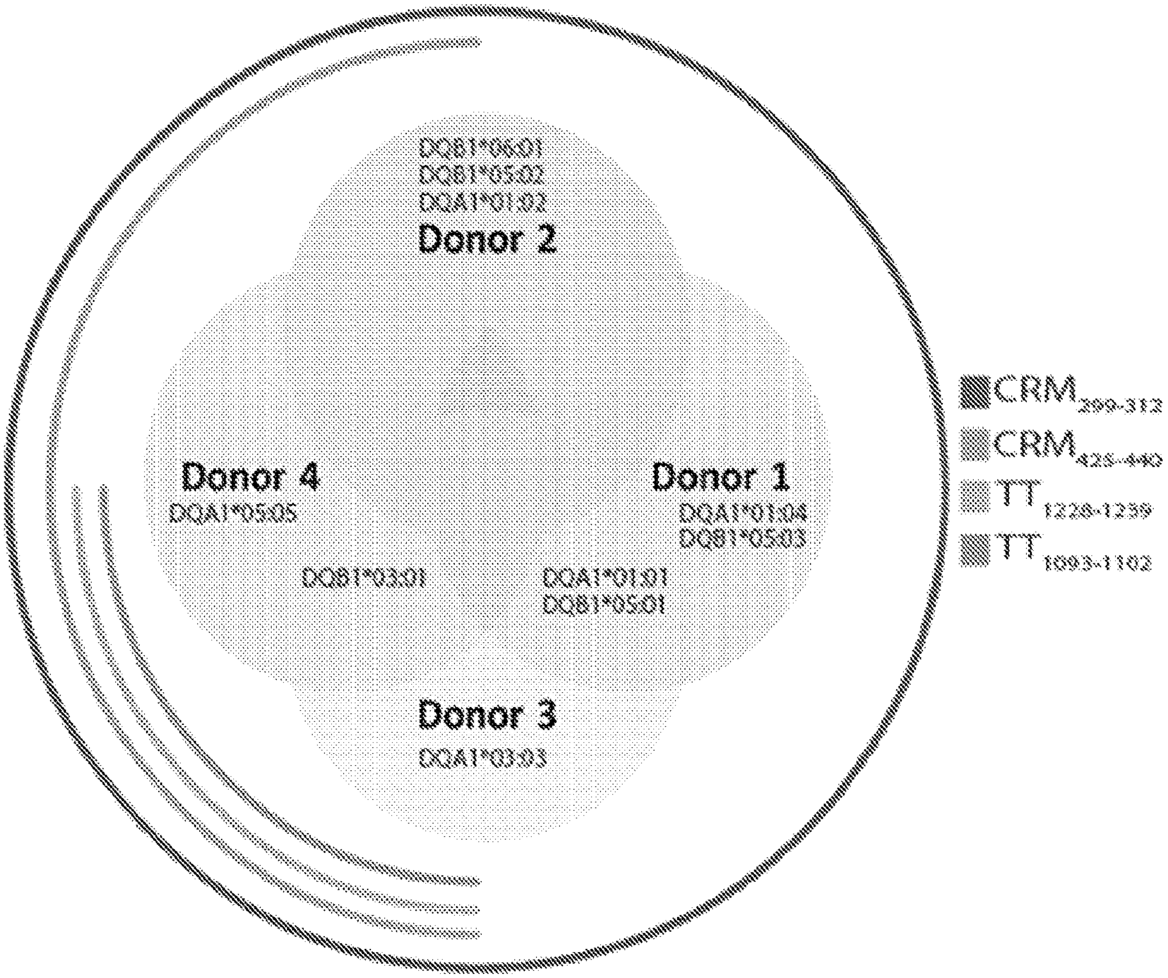
Figure 8C:
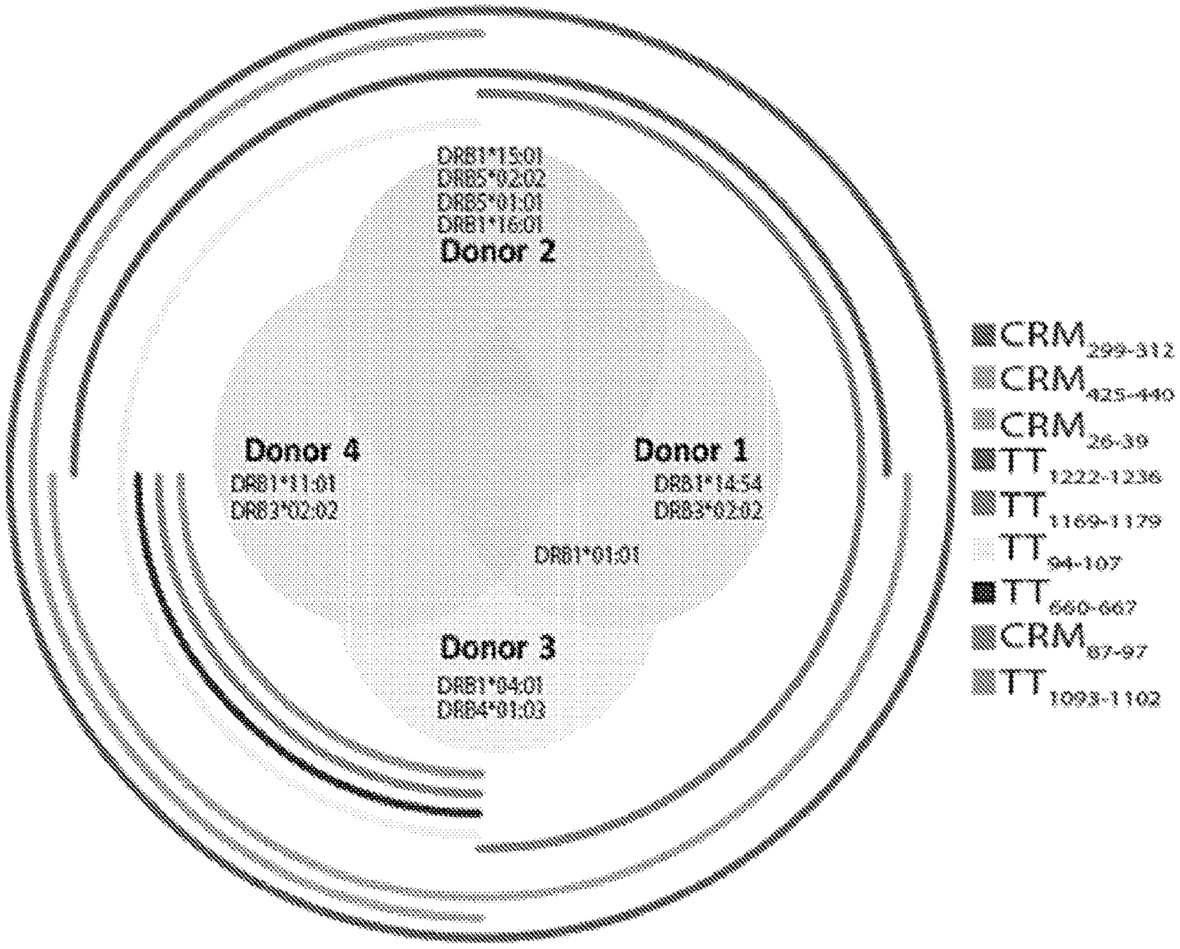
Figure 9A:
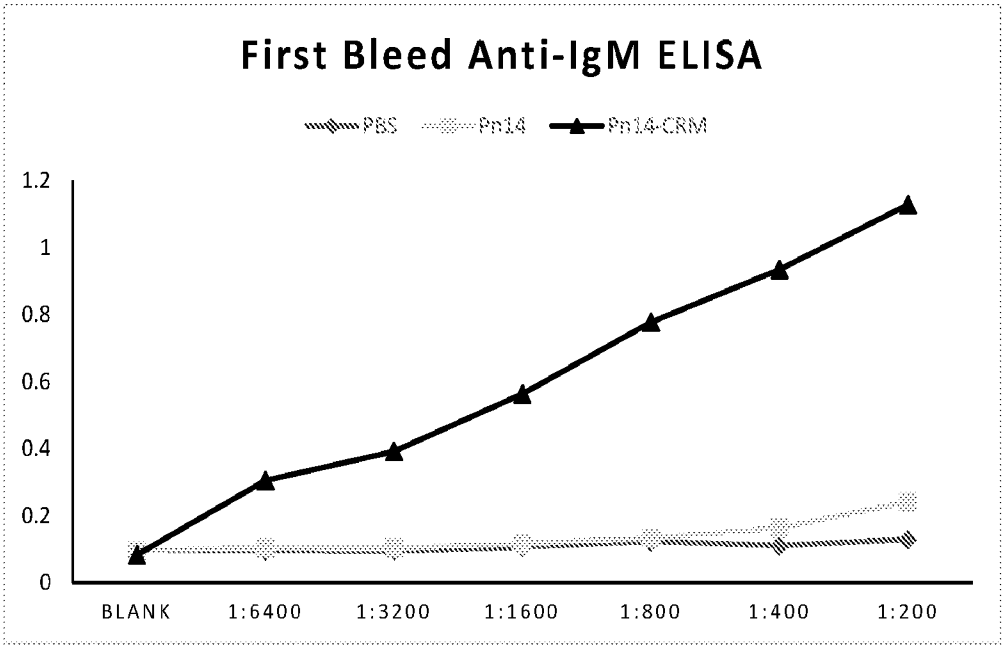
FIGS. 9A-D show the immune response after immunization with conjugate. IgM response (FIG. 9A) and IgG response (FIG. 9B) 14 days after first immunization. IgM response (FIG. 9C) and IgG response (FIG. 9D) 14 days after second immunization.
Figure 9B:
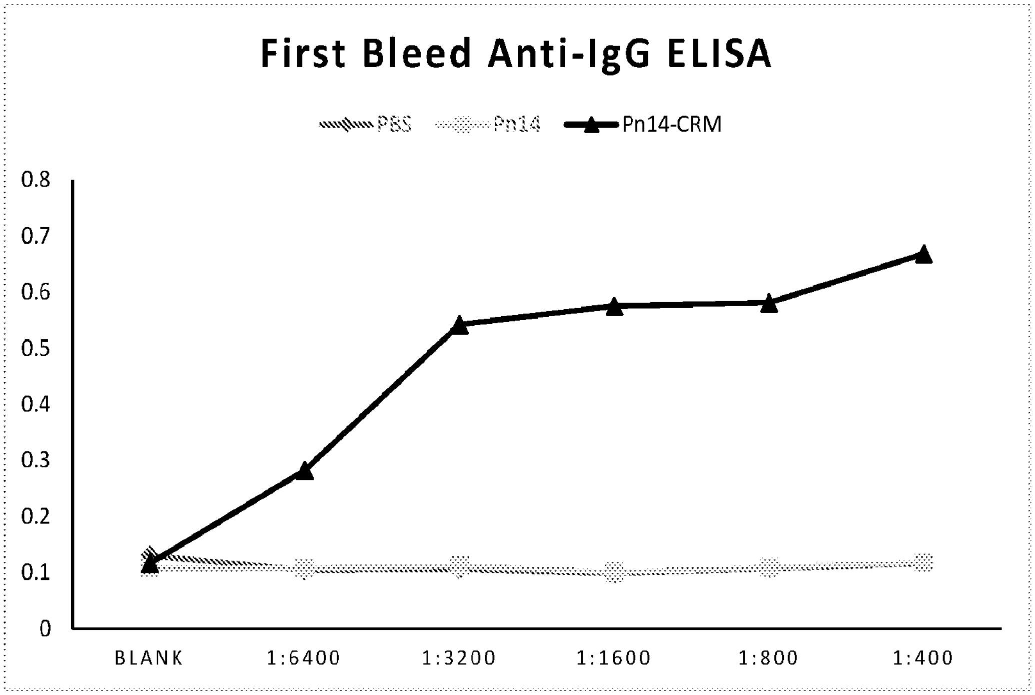
Figure 9C:
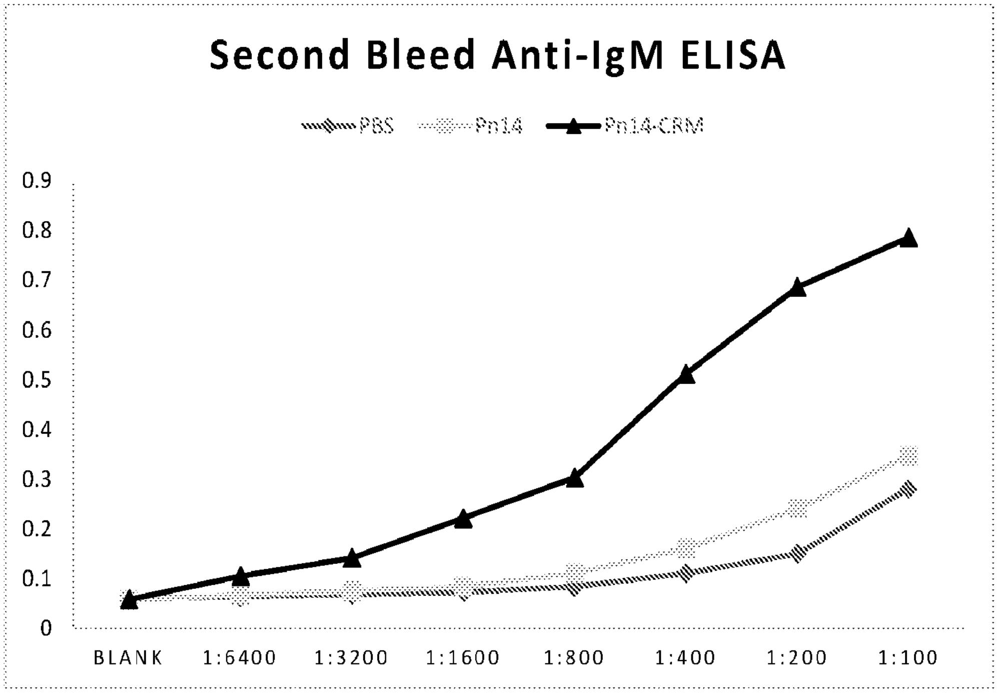
Figure 9D:
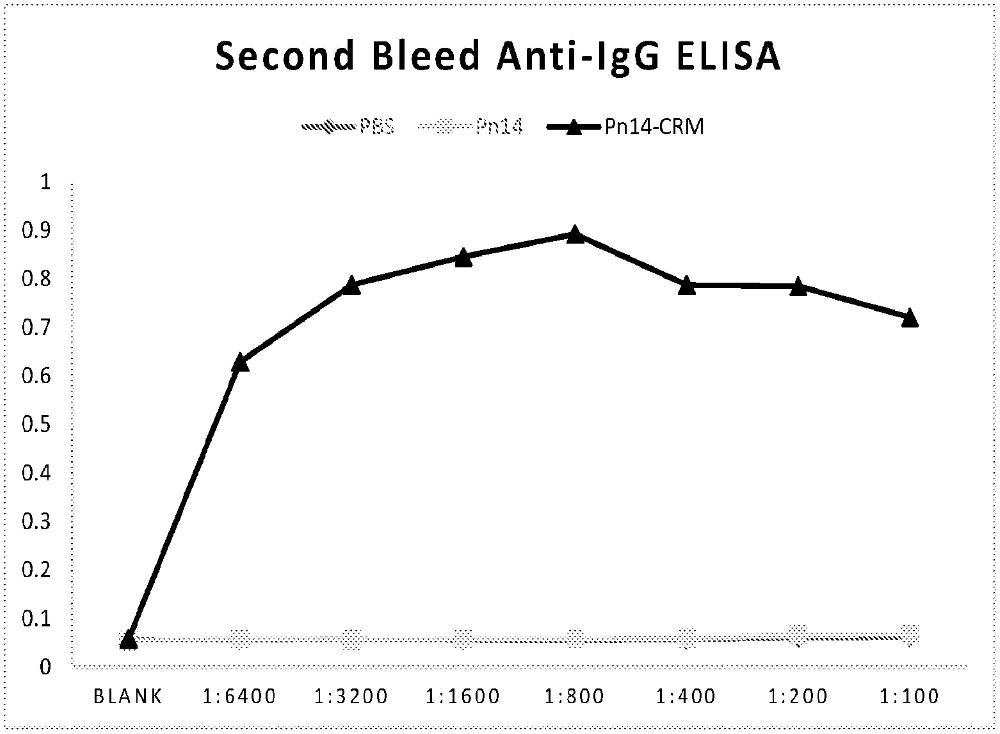

Next, we assessed the ability of the newly identified $CRM_{197}$ and TT peptides to stimulate CD4+ T cells. For this purpose, we used CD4+ enriched donor PBMCs and monitored percent of CFSE depletion in CD4+ T cells after 6 days of incubation with each peptide. We observed that each donor responded to one or more of the identified peptides as well as the full carrier proteins (Table 2). Donor 1 displayed increased proliferation to peptides $TT_{1169-1179}$ (P32-like peptide), $TT_{1222-1236}$, $CRM_{26-39}$, and $CRM_{299-312}$ (FIG. 5*b*). Several other peptides showed slight increase compared to the basal growth rate but were not significant. Interestingly, Donor 1 did not show increased proliferation to "universal" TT peptides P2 or P32 (FIG. 5*b*). Donor 2 had increased proliferation compared to basal growth for peptides P32, $TT_{94-107}$, $TT_{1169-1179}$, $TT_{1222-1236}$, $CRM_{299-312}$, and $CRM_{425-440}$ (FIG. 5*c*). Donor 2 did not show significant proliferation of the "universal" TT peptide P2. Additionally, slight proliferative increases were seen in $TT_{1093-1102}$ and in $CRM_{87-97}$, but they were not significant compared to basal growth rate (FIG. 5*c*). Donors 3 and 4 showed broad significant T cell proliferation compared to basal growth rate for all identified peptides except two TT peptides each (Table 2, FIG. 5*a, d, e*). Donor 3 had no significant response to peptides $TT_{826-837}$ and $TT_{1222-1236}$, while Donor 4 had no response to peptides $TT_{826-837}$ and $TT_{1169-1179}$. Notably, one peptide, $CRM_{299-312}$, gave a positive response in all four donors, while peptides $CRM_{425-440}$, $CRM_{26-39}$, $TT_{94-107}$, $TT_{1222-1236}$, and $TT_{1169-1179}$ (P32-like peptide) gave positive response in three out of the four donors. Taken together, these results suggest each identified peptide has the capability of proliferating donor CD4+ T cells and six of the peptides responded in three or more donors.

To examine the ability of the identified peptides to stimulate the production of cytokine IFN-γ by T cell, we tested cell supernatants via ELISA (FIG. 6). Culture supernatants from CD4+ T cell enriched donor PBMCs were stimulated with full carrier proteins or identified peptides and screened for IFN-γ production after 6 days. Each identified peptide, and carrier protein, was capable of stimulating IFN-γ production in one or more donors (Table 2). As expected, the results for IFN-γ screening closely matched results from the proliferation assay with few discrepancies. Donor 1 had significant levels of IFN-γ response to $TT_{660-667}$, $TT_{1093-1102}$, and CRM peptides 26-39, 87-97, and 299-312 (FIG. 6*a*). Donor 2 displayed significant production of IFN-γ for eight identified peptides, $TT_{94-107}$, $TT_{1093-1102}$, $TT_{1169-1179}$, $TT_{1222-1236}$, $CRM_{26-39}$, $CRM_{87-97}$, $CRM_{299-312}$, and $CRM_{425-440}$ (FIG. 6*b*). Donor 3 had significant IFN-γ production towards each peptide except two (FIG. 6*c*). Likewise, Donor 4 had significant IFN-γ production in response to every peptide except two (FIG. 6*d*). Overall, eight peptides were able to produce significant levels of IFN-γ in at least three donors: $TT_{94-107}$, $TT_{660-667}$, $TT_{1093-1102}$, $TT_{1169-1179}$ (P32-like peptide), $CRM_{26-39}$, $CRM_{87-97}$, $CRM_{299-312}$, and $CRM_{425-440}$.

Donors have Unique Subset of Class II Alleles

We hypothesize that donors respond to different peptides due to their distinct HLA allele expression. To reveal the correlations, we assessed the class II genotype of each donor (Table 3). In brief, individual donor DNA was isolated and HLA gene capture was performed. After library construction deep sequencing was completed to determine HLA alleles at loci DPA1, DPB1, DQA1, DQB1, DRB1, and DR345 for each donor. Each donor has two alleles per loci with resolution to six digits (Table 3). However, Donors 1 and 3 only had a single allele for loci DR345 (Table 3), as not every individual possess the DRB3 loci (44).

TABLE 3

MHC allelic profile of each donor and Raji B Cells. Both alleles for each isotype are shown (allele 1/allele 2). Raji B cell alleles were determined in reference 43.

| | Donor 1 | Donor 2 | Donor 3 | Donor 4 | Raji B Cells |
|---|---|---|---|---|---|
| DPA1* | 01:03:01/ 01:03:01 | 01:30:01/ 01:03:01 | 01:03:01/ 01:03:01 | 01:03:01/ 01:03:01 | N/A |
| DPB1* | 03:01:01/ 04:01:01 | 02:01:02/ 04:01:01 | 04:01:01/ 04:02:01 | 04:01:01/ 04:01:01 | 01:01:01/ 01:01:01 |
| DQA1* | 01:01:01/ 01:04:01 | 01:02:01/ 01:02:02 | 01:01:01/ 03:03:01 | 05:05:01/ 05:05:01 | 01:01:01/ 05:01:01 |
| DQB1* | 05:01:01/ 05:03:01 | 05:02:01/ 06:01:01 | 03:01:01/ 05:01:01 | 03:01:01/ 03:01:01 | 02:01:01/ 05:01:01 |
| DRB1* | 01:01:01/ 14:54:01 | 15:01:01/ 16:01:01 | 01:01:01/ 04:01:01 | 11:01:01/ 11:01:01 | 03:01:01/ 10:01:01 |
| DRB345* | B3*02: 02:01 | B5*01:01: 01/B5*02: 02:01 | B4*01: 03:01 | B3*02: 02:01/ B3*02: 02:01 | B3*02: 02:01/ B3*02:12 |

As expected, three donors were heterozygous for each loci alleles, with the exception of DPA1 (Table 3). This is most likely due to the low polymorphism of the DPA1 loci (44). All four donors are homozygous and express the allele DPA1*01:03:01, which is the most dominant allele in the United States populations (45).

Next, we established which alleles were shared between donors and how this correlates with positively responding peptides (FIG. 7). Interestingly, all four donors express at least one allele of DPA1*01:03 and DPB1*04:01 (FIG. 7*a*, Table 3). $CRM_{299-312}$ was the only peptide pulled down in the HLA-DP specific immunoprecipitation and it gave a positive T cell proliferative response in all four donors as determined by CFSE depletion (FIG. 7*a*). In looking at the HLA-DQ alleles for each donor, there was no single allele shared between all; however, Donors 1 and 3 share two alleles, while Donors 3 and 4 share one (FIG. 7*b*). There were four peptides pulled down in the –DQ IP, $TT_{1093-1102}$, $TT_{1228-1239}$, $CRM_{299-312}$, and $CRM_{425-440}$. Both TT peptides gave positive response in Donors 3 and 4, while $CRM_{450-465}$ gave response in Donors 2,3, and 4 and $CRM_{299-312}$ in all four donors (FIG. 7*b*). Unsurprisingly, there was little overlap between donors and alleles of DRB1 and DRB345. HLA-DR loci have one of the highest levels of polymorphism with hundreds of alleles present in the population (46). However, Donors 1 and 3 share allele DRB1*01:01 (FIG. 7*c*). There were nine identified peptides that gave positive response in two or more donors pulled down from the –DR IP ($TT_{826-837}$ was also identified through this IP but failed to give significant response in more than one donor). Peptides $TT_{660-667}$, $TT_{1093-1102}$, and $CRM_{87-97}$ gave significant response in Donors 3 and 4 (FIG. 7*c*). Peptides, $TT_{94-107}$, $TT_{1169-1179}$, $TT_{1222-1236}$, $CRM_{26-39}$, and $CRM_{425-440}$ gave significant response in three donors each. Peptide $CRM_{299-312}$ was also identified through the –DR IP, much like –DP and –DQ, and gave a significant response in all four donors (FIG. 7*c*). Taken together, we have identified a subset of peptides that give significant T cell response in multiple donors that have different MHC class II genotypes, and that donors have different alleles from Raji B cells which were first used to identify peptides. This suggests possible immunodominant roles for these peptides in immune presentation and may have implications for rational vaccine design.

Discussion

Despite past reports on T cell epitopes of carrier proteins $CRM_{197}$ and TT (14, 18, 21, 29-36), we know little about the exact nature of presented peptides after processing in the APCs. This study sought to explore the epitopes that are naturally processed by the APCs and presented via MHCII when exposed to the common conjugate vaccine carrier proteins $CRM_{197}$ and tetanus toxoid. Herein, we define a set of eleven new CD4+ T cell epitopes for TT or $CRM_{197}$ proteins utilizing mass spectrometry of MHCII presented peptides. Each of the eleven peptides is capable of stimulating CD4+ T cells in at least one donor, with six peptides stimulating T cells in three or more donors, suggesting an immunodominant role for these epitopes. In support of this, all four donors have different class II genotypes from each other as well as from the Raji cell line originally used to identify the peptides demonstrating these peptides are associated with multiple alleles of MHCII. Based on a recently published study analyzing HLA-DR and DQ alleles in US population, one or more MHCII alleles in all four donors are identified as top 10 most common allele in the United States population across ethnicities (47). Additionally, every allele (DRB1, DQB1 and DPB1) in all donors and Raji cell line are considered a common allele as described by the Common and Well-Documented (CWD) alleles catalogue (45, 48, 49). This allelic information paired with our donor T cell data suggests these identified peptides could bind MHCII in a large subset of the population, making them potentially ideal vaccine component.

Interestingly, we observed no significant response against the previously published TT epitopes P2 and P32 in one or more donors. This is consistent with a recent study on T cell responses to TT (34) wherein researchers show no significant responses to universal epitope P2. Having this observation in multiple studies necessitates a direct methodology that follows natural MHCII pathway to define T cell epitopes as laid out in this study. Previous works reporting T cell epitopes of TT and $CRM_{197}$ did so through indirect methodologies (14, 21, 29-31, 33-36). Synthetic peptides were utilized spanning the protein sequence, typically 20 residues in length overlapping by 5-10 residues, or using epitope prediction softwares. T cell activation was then tested using T cell clones or donor PBMCs (14, 21, 29-31, 33-36). While these methodologies are robust and streamlined, epitopes identified through these studies may not reflect true T cell epitopes generated through antigen processing and presentation. With advancements in mass spectrometry techniques, it is now possible to determine the exact nature of peptides processed in the endolysosomes and presented for immune activation.

During our MS analysis of the MHCII presented peptides, no proteases were utilized prior to MS to capture the full length and sequence of the MHCII bound peptides. Discovery of two peptides that overlap slightly with P2 and P32 with different N-terminal residues demonstrate that identification of naturally processed peptides is preferable to alternative screening approaches. Thus, characterizing epitopes isolated from MHCII pathway could yield new immunodominant peptides. These findings may also suggest that MHCII proteins may prefer different binding registers than what has been previously described. Indeed, a number of reports have shown the ability of MHCII proteins to bind well-known MHCII epitope $OVA_{323-339}$ in distinct registers (50, 51). These studies indicate that MHCII proteins are capable of binding the same peptide in different ways, suggesting why we observed similar, yet distinct peptides from what has been described. This also suggests that previously published peptides identified through use of overlapping synthetic peptides spanning the complete protein sequence or peptides found through prediction algorithms may not be 1) what MHCII preferentially binds to and 2) the most effective approach for identifying true immunogenic peptides.

Recently, there has been a shift towards utilizing immunogenic peptides as carriers for vaccine candidates over the full-length carrier proteins. Several past studies have explored this idea (8, 18, 22-24, 26-28) and shown that the candidates work as well (19-21), or better than traditional carrier protein vaccines (8). Importantly, this shift is not just a current trend, but rather based on logic and our knowledge of the immune system. After processing in the endolysosome of the APCs, proteins are broken into fragments with only a small subset of these fragments capable of MHCII binding. By supplying the immune system with the exact epitopes necessary for presentation we can ensure every epitope is utilized to enrich for a more robust T cell mediated response. Additionally, the use of these peptide constructs for vaccine candidates accurately recapitulates what is occurring in the endolysosome. Furthermore, these peptides are the smallest units possible for MHC binding and are not likely degraded further, which may alter their immune activity.

Discovering a repertoire of MHCII-binding peptides derived from multiple carrier proteins is critical since most peptides by themselves are limited in their MHCII allelic coverage. Therefore, a number of strategies have been proposed and studied to overcome this limitation. Studies have been done on linking strings of MHCII promiscuous peptides together (19, 20, 25), utilizing liposomes (52), nanoparticles (53), and more. These studies show the feasibility and future direction of utilizing peptide epitopes for the generation of conjugate vaccines over full-length carrier proteins. Moreover, shifting towards immunogenic peptide epitopes allows for more robust and cost-effective means of vaccine production as peptides can be produced on a larger scale, high yield, and at low cost. The knowledge gained from this work will aid in defining these MHCII binding peptides to be used in the production of knowledge-based next generation vaccines.

EXAMPLE 1 CITATIONS

1. Goldblatt, D. 2000. Conjugate vaccines. *Clin Exp Immunol* 119:1-3.
2. Wantuch, P. L., and F. Y. Avci. 2018. Current status and future directions of invasive pneumococcal diseases and prophylactic approaches to control them. *Hum Vaccin Immunother* 14:2303-2309.
3. Pichichero, M. E. 2013. Protein carriers of conjugate vaccines: characteristics, development, and clinical trials. *Hum Vaccin Immunother* 9:2505-2523.
4. Micoli, F., R. Adamo, and P. Costantino. 2018. Protein Carriers for Glycoconjugate Vaccines: History, Selection Criteria, Characterization and New Trends. *Molecules* 23.
5. Rammensee, H. G., T. Friede, and S. Stevanovic. 1995. MHC ligands and peptide motifs: first listing. *Immunogenetics* 41:178-228.
6. Hunt, D. F., H. Michel, T. A. Dickinson, J. Shabanowitz, A. L. Cox, K. Sakaguchi, E. Appella, H. M. Grey, and A. Sette. 1992. Peptides presented to the immune system by the murine class II major histocompatibility complex molecule I-Ad. *Science* 256:1817-1820.
7. Avalos, A. M., and H. L. Ploegh. 2014. Early BCR Events and Antigen Capture, Processing, and Loading on MHC Class II on B Cells. *Front Immunol* 5:92.
8. Avci, F., X. Li, M. Tsuji, and D. Kasper. 2011. A mechanism for glycoconjugate vaccine activation of the adaptive immune system and its implications for vaccine design. *Nature Medicine* 17:1602-U1115.
9. Middleton, D. R., L. Sun, A. V. Paschall, and F. Y. Avci. 2017. T Cell-Mediated Humoral Immune Responses to Type 3 Capsular Polysaccharide of. *J Immunol* 199:598-603.
10. Sun, X., G. Stefanetti, F. Berti, and D. L. Kasper. 2019. Polysaccharide structure dictates mechanism of adaptive immune response to glycoconjugate vaccines. *Proc Natl Acad Sci USA* 116:193-198.
11. Sun, L., D. R. Middleton, P. L. Wantuch, A. Ozdilek, and F. Y. Avci. 2016. Carbohydrates as T-cell antigens with implications in health and disease. *Glycobiology* 26:1029-1040.
12. Rappuoli, R., E. De Gregorio, and P. Costantino. 2019. On the mechanisms of conjugate vaccines. *Proc Natl Acad Sci USA* 116:14-16.
13. Avci, F. 2013. Novel Strategies for Development of Next-Generation Glycoconjugate Vaccines. *Current Topics in Medicinal Chemistry* 13:2535-2540.
14. Panina-Bordignon, P., A. Tan, A. Termijtelen, S. Demotz, G. Corradin, and A. Lanzavecchia. 1989. Universally immunogenic T cell epitopes: promiscuous binding to human MHC class II and promiscuous recognition by T cells. *Eur J Immunol* 19:2237-2242.
15. Wantuch, P. L., and F. Y. Avci. 2019. Invasive pneumococcal disease in relation to vaccine type serotypes. *Hum Vaccin Immunother:* 1-2.
16. Schutze, M. P., C. Leclerc, M. Jolivet, F. Audibert, and L. Chedid. 1985. Carrier-induced epitopic suppression, a major issue for future synthetic vaccines. *J Immunol* 135:2319-2322.
17. Schutze, M. P., C. Leclerc, F. R. Vogel, and L. Chedid. 1987. Epitopic suppression in synthetic vaccine models: analysis of the effector mechanisms. *Cell Immunol* 104:79-90.
18. Etlinger, H. M., D. Gillessen, H. W. Lahm, H. Matile, H. J. Schönfeld, and A. Trzeciak. 1990. Use of prior vaccinations for the development of new vaccines. *Science* 249:423-425.

19. Falugi, F., R. Petracca, M. Mariani, E. Luzzi, S. Mancianti, V. Carinci, M. L. Melli, O. Finco, A. Wack, A. Di Tommaso, M. T. De Magistris, P. Costantino, G. Del Giudice, S. Abrignani, R. Rappuoli, and G. Grandi. 2001. Rationally designed strings of promiscuous CD4+ T cell epitopes provide help to *Haemophilus influenzae* type b oligosaccharide: a model for new conjugate vaccines. Eur. J. Immunol 31:3816-3824.
20. Baraldo, K., E. Mori, A. Bartoloni, F. Norelli, G. Grandi, R. Rappuoli, O. Finco, and G. Del Giudice. 2005. Combined conjugate vaccines: enhanced immunogenicity with the N19 polyepitope as a carrier protein. *Infect Immun* 73:5835-5841.
21. Bixler, G. S., R. Eby, K. M. Dermody, R. M. Woods, R. C. Seid, and S. Pillai. 1989. Synthetic peptide representing a T-cell epitope of $CRM_{197}$ substitutes as carrier molecule in a *Haemophilus influenzae* type B (Hib) conjugate vaccine. *Adv Exp Med Biol* 251:175-180.
22. Jackson, D. C., A. W. Purcell, C. J. Fitzmaurice, W. Zeng, and D. N. Hart. 2002. The central role played by peptides in the immune response and the design of peptide-based vaccines against infectious diseases and cancer. *Curr Drug Targets* 3:175-196.
23. Cai, H., M. S. Chen, Z. Y. Sun, Y. F. Zhao, H. Kunz, and Y. M. Li. 2013. Self-adjuvanting synthetic antitumor vaccines from MUC1 glycopeptides conjugated to T-cell epitopes from tetanus toxoid. *Angew Chem Int Ed Engl* 52:6106-6110.
24, de Velasco, E. A., D. Merkus, S. Anderton, A. F. Verheul, E. F. Lizzio, R. Van der Zee, W. Van Eden, T. Hoffman, J. Verhoef, and H. Snippe. 1995. Synthetic peptides representing T-cell epitopes act as carriers in pneumococcal polysaccharide conjugate vaccines. *Infect Immun* 63:961-968.
25. Slingluff, C. L. 2011. The present and future of peptide vaccines for cancer: single or multiple, long or short, alone or in combination? *Cancer J* 17:343-350.
26. Rodrigues-da-Silva, R. N., D. Correa-Moreira, I. F. Soares, P. M. de-Luca, P. R. R. Totino, F. N. Morgado, M. D. G. Oliveira Henriques, A. L. Peixoto Candea, B. Singh, M. R. Galinski, A. Moreno, J. Oliveira-Ferreira, and J. D. C. Lima-Junior. 2019. Immunogenicity of synthetic peptide constructs based on PvMSP9E795-A808, a linear B-cell epitope of the *P. vivax* Merozoite Surface Protein-9. *Vaccine* 37:306-313.
27. Snook, A. E., T. R. Baybutt, T. Hyslop, and S. A. Waldman. 2016. Preclinical Evaluation of a Replication-Deficient Recombinant Adenovirus Serotype 5 Vaccine Expressing Guanylate Cyclase C and the PADRE T-helper Epitope. *Hum Gene Ther Methods* 27:238-250.
28. Zeigler, D. F., R. Roque, and C. H. Clegg. 2019. Optimization of a multivalent peptide vaccine for nicotine addiction. *Vaccine* 37:1584-1590.
29. Demotz, S., A. Lanzavecchia, U. Eisel, H. Niemann, C. Widmann, and G. Corradin. 1989. Delineation of several DR-restricted tetanus toxin T cell epitopes. *J Immunol* 142:394-402.
30. Diethelm-Okita, B. M., D. K. Okita, L. Banaszak, and B. M. Conti-Fine. 2000. Universal epitopes for human CD4+ cells on tetanus and diphtheria toxins. *J Infect Dis* 181: 1001-1009.
31. Diethelm-Okita, B. M., R. Raju, D. K. Okita, and B. M. Conti-Fine. 1997. Epitope repertoire of human CD4+ T cells on tetanus toxin: identification of immunodominant sequence segments. *J Infect Dis* 175:382-391.
32. Southwood, S., J. Sidney, A. Kondo, M. F. del Guercio, E. Appella, S. Hoffman, R. T. Kubo, R. W. Chesnut, H. M. Grey, and A. Sette. 1998. Several common HLA-DR types share largely overlapping peptide binding repertoires. *J Immunol* 160:3363-3373.
33. Demotz, S., C. Barbey, G. Corradin, A. Amoroso, and A. Lanzavecchia. 1993. The set of naturally processed peptides displayed by DR molecules is tuned by polymorphism of residue 86. *Eur J Immunol* 23:425-432.
34. da Silva Antunes, R., S. Paul, J. Sidney, D. Weiskopf, J. M. Dan, E. Phillips, S. Mallal, S. Crotty, A. Sette, and C. S. Lindestam Arlehamn. 2017. Definition of Human Epitopes Recognized in Tetanus Toxoid and Development of an Assay Strategy to Detect Ex Vivo Tetanus CD4+ T Cell Responses. *Plos One* 12: e0169086.
35. Leonard, E. G., D. H. Canaday, C. V. Harding, and J. R. Schreiber. 2003. Antigen processing of the heptavalent pneumococcal conjugate vaccine carrier protein $CRM_{197}$ differs depending on the serotype of the attached polysaccharide. *Infection and Immunity* 71:4186-4189.
36. Raju, R., D. Navaneetham, D. Okita, B. Diethelm-Okita, D. McCormick, and B. M. Conti-Fine. 1995. Epitopes for human CD4+ cells on diphtheria toxin: structural features of sequence segments forming epitopes recognized by most subjects. *Eur J Immunol* 25:3207-3214.
37. Cobb, B. A., Q. Wang, A. O. Tzianabos, and D. L. Kasper. 2004. Polysaccharide processing and presentation by the MHCII pathway. *Cell* 117:677-687.
38. Bozzacco, L., H. Yu, H. A. Zebroski, J. Dengjel, H. Deng, S. Mojsov, and R. M. Steinman. 2011. Mass spectrometry analysis and quantitation of peptides presented on the MHC II molecules of mouse spleen dendritic cells. *J Proteome Res* 10:5016-5030.
39. Dongre, A. R., S. Kovats, P. deRoos, A. L. McCormack, T. Nakagawa, V. Paharkova-Vatchkova, J. Eng, H. Caldwell, J. R. Yates, 3rd, and A. Y. Rudensky. 2001. In vivo MHC class II presentation of cytosolic proteins revealed by rapid automated tandem mass spectrometry and functional analyses. *Eur J Immunol* 31:1485-1494.
40. Velazquez, C., R. DiPaolo, and E. R. Unanue. 2001. Quantitation of lysozyme peptides bound to class II MHC molecules indicates very large differences in levels of presentation. *J Immunol* 166:5488-5494.
41. Lippolis, J. D., F. M. White, J. A. Marto, C. J. Luckey, T. N. Bullock, J. Shabanowitz, D. F. Hunt, and V. H. Engelhard. 2002. Analysis of MHC class II antigen processing by quantitation of peptides that constitute nested sets. *J Immunol* 169:5089-5097.
42. Kerblat, I., S. Tongiani-Dahshan, C. Aude-Garcia, M. Villiers, C. Drouet, and P. N. Marche. 2000. Tetanus toxin L chain is processed by major histocompatibility complex class I and class II pathways and recognized by CD8+ or CD4+ T lymphocytes. *Immunology* 100:178-184.
43. Bentley, G., R. Higuchi, B. Hoglund, D. Goodridge, D. Sayer, E. A. Trachtenberg, and H. A. Erlich. 2009. High-resolution, high-throughput HLA genotyping by next-generation sequencing. *Tissue Antigens* 74:393-403.
44. Murphy, K., and C. Weaver. 2017. *Janeway's Immunobiology*. Garland Science, Taylore & Francis Group LLC, New York, NY.
45. Gonzalez-Galarza, F. F., L. Y. Takeshita, E. J. Santos, F. Kempson, M. H. Maia, A. L. da Silva, A. L. Teles e Silva, G. S. Ghattaoraya, A. Alfirevic, A. R. Jones, and D. Middleton. 2015. Allele frequency net 2015 update: new features for HLA epitopes, KIR and disease and HLA adverse drug reaction associations. *Nucleic Acids Res* 43: D784-788.

46. van Lith, M., R. M. McEwen-Smith, and A. M. Benham. 2010. HLA-DP, HLA-DQ, and HLA-DR have different requirements for invariant chain and HLA-DM. *J Biol Chem* 285:40800-40808.
47. Maiers, M., L. Gragert, and W. Klitz. 2007. High-resolution HLA alleles and haplotypes in the United States population. *Hum Immunol* 68:779-788.
48. Mack, S. J., P. Cano, J. A. Hollenbach, J. He, C. K. Hurley, D. Middleton, M. E. Moraes, S. E. Pereira, J. H. Kempenich, E. F. Reed, M. Setterholm, A. G. Smith, M. G. Tilanus, M. Torres, M. D. Varney, C. E. Voorter, G. F. Fischer, K. Fleischhauer, D. Goodridge, W. Klitz, A. M. Little, M. Maiers, S. G. Marsh, C. R. Müller, H. Noreen, E. H. Rozemuller, A. Sanchez-Mazas, D. Senitzer, E. Trachtenberg, and M. Fernandez-Vina. 2013. Common and well-documented HLA alleles: 2012 update to the CWD catalogue. *Tissue Antigens* 81:194-203.
49. Castelli, F. A., C. Buhot, A. Sanson, H. Zarour, S. Pouvelle-Moratille, C. Nonn, H. Gahery-Ségard, J. G. Guillet, A. Ménez, B. Georges, and B. Maillère. 2002. HLA-DP4, the most frequent HLA II molecule, defines a new supertype of peptide-binding specificity. *J Immunol* 169:6928-6934.
50. Scott, C. A., P. A. Peterson, L. Teyton, and I. A. Wilson. 1998. Crystal structures of two I-Ad-peptide complexes reveal that high affinity can be achieved without large anchor residues. *Immunity* 8:319-329.
51. McFarland, B. J., A. J. Sant, T. P. Lybrand, and C. Beeson. 1999. Ovalbumin (323-339) peptide binds to the Major Histocompatibility Complex Class II I-A protein using two functionally distinct registers. *Biochemistry* 38:16663-16670.
52. Riaz, M. K., M. A. Riaz, X. Zhang, C. Lin, K. H. Wong, X. Chen, G. Zhang, A. Lu, and Z. Yang. 2018. Surface Functionalization and Targeting Strategies of Liposomes in Solid Tumor Therapy: A Review. *Int J Mol Sci* 19.
53. Fujita, Y., and H. Taguchi. 2011. Current status of multiple antigen-presenting peptide vaccine systems: Application of organic and inorganic nanoparticles. *Chem Cent J* 5:48.

EXAMPLE 2

Galactose Oxidase Modification of *S. pneumoniae* Capsular Polysaccharide Followed by Reductive Amination in the Formation of Glycoconjugates Described herein is a method for forming glycoconjugates. The method uses conditions that are more gentle than standard methods that typically include use of periodate oxidation and result in an unexpectedly high immunogenicity of the glycoconjugate.

Methods

Purified *S. pneumoniae* Type 14 polysaccharide (Pn14, 1.5 milligrams) was dissolved into 500 microliters of 100 mM Sodium Carbonate buffer (pH 8.3). The polysaccharide has a large size (>500 kDa) and thus was treated by ozonolysis using an ozone generator at a rate of 10 mg/min for 3 minutes, leaving the Pn14 at a mass of ~100 kDa, as determined by Size Exclusion FPLC elution on an SEC 650 column using known-sized Dextran as controls and as determined by Refractive Index.

Still in Sodium Carbonate buffer, twenty micrograms of recombinantly expressed and purified Galactose Oxidase enzyme and one microgram of Catalase (to decompose Hydrogen Peroxide formed) were added and the reaction vessel was purged with purified Oxygen. The enzyme treatment proceeded for six hours at 37° C., resulting in multiple sites of oxidation along the polysaccharide chain.

The sample was then heat shocked for five minutes at 95° C. to deactivate the Galactose Oxidase and the oxidized Pn14 purified was through Size Exclusion FPLC using Sodium Carbonate buffer.

To the oxidized Pn14 sample, 1 milligram of the carrier protein CRM-197 was added and the reaction mixture concentrated to 500 microliters using a 10 kDa Molecular Weight Cut-Off Spin Column. The concentrated reaction mixture was then pH adjusted to pH 7.5 using 1 M HCl and treated with six milligrams of the reducing agent Sodium Cyanoborohydride (~200 mM Concentration). The reductive amination reaction proceeded over 72 hours at 35 C.

After 72 hours, the reaction vessel was treated with one milligram of Sodium Borohydride to quench the reaction and convert any unreacted aldehyde groups back into the native alcohol.

The reaction was purified using Size Exclusion FPLC with Phosphate Buffered Saline (Ph 7.3) as the buffer. The Pn14-CRM conjugate was identified by the shift in Refractive index from the smaller sized Pn14 as well as the corroborating signal at 280 nm Absorbance, due to the conjugation of the carrier protein.

The collected fractions underwent extensive dialysis using 30 kDa Cutoff dialysis membrane and deionized water for 24 hours, with multiple water exchanges. The desalted product was then frozen and lyophilized to give the purified conjugate. Essentially identical methods were used to conjugate Pn14 to multimers.

Using CRM-197 as a proof-of-principle carrier for this chemoenzymatic approach in the formation of a *S. pneumoniae* conjugate, Pn14-CRM conjugates were synthesized and administered in a dosage of 4 micrograms of conjugate per mouse, using Aluminum Hydroxide (Alum) as an adjuvant. The mice were administered a primary immunization (Day 0) and booster immunization (Day 14), with IgM and IgG antibody titers analyzed from sera collected at first bleed before the second immunization (Day 14) and second bleed two weeks after the second immunization (Day 28). These experiments were performed by ELISA using a preformed HSA-Pn14 conjugate to coat the plate and various dilutions of mouse sera from immunization groups. As control groups, sera from mice immunized with polysaccharide alone (Pn14+Alum) or PBS+Alum are shown. The ELISA results of these experiment are shown in four separate graphs according to both first or second bleed and IgM or IgG titers, respectively (FIGS. 9A-D)

Results

The results show a strong IgG response from the conjugate even after a single administration of the vaccine. These results continued upon administration of a boost, where a surprisingly robust IgG response was seen, quickly reaching saturation at the lowest concentration of sera tested (1:6400). In traditional conjugate vaccine preparations that depend on periodate oxidation to form aldehyde chemical handles, these levels of IgG titers are not typically observed.

EXAMPLE 3

Application of Galactose Oxidase and its Mutated Form in Capsular Polysaccharide Modification As a proof of principle, Pn14 was used to create a conjugate vaccine (Example 2). However, using the mutated form of Galactose Oxidase created by directed evolution to increase substrate capabilities (Rannes et al., 2011, J. Am.

Chem. Soc., 133:8436-8439, dx.doi.org/10.1021/ja201847), we have shown activity towards two additional *S. pneumoniae* serotypes, 3 and 4.

Figure 10A:
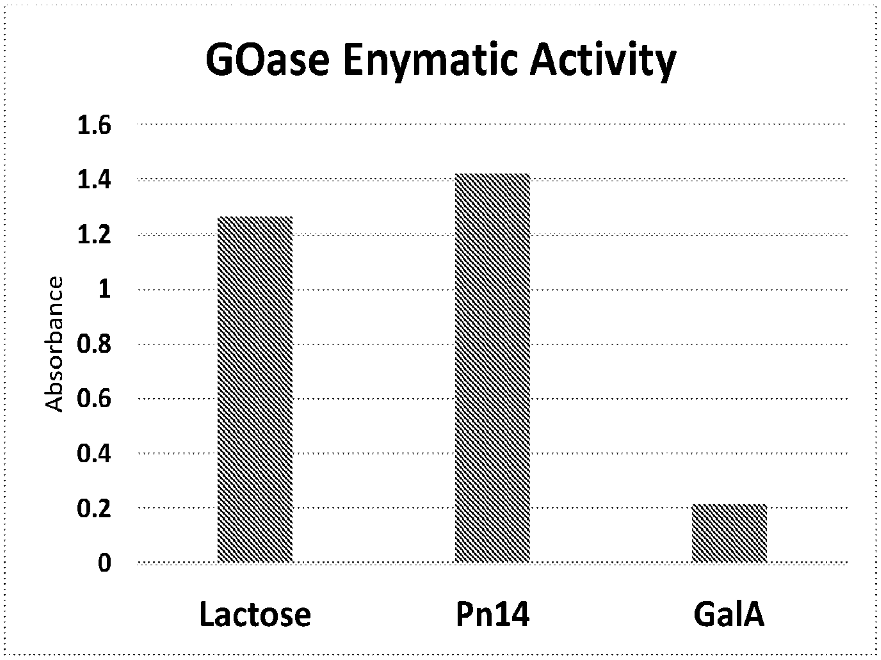
FIGS. 10A-B show the enzymatic activity of two galactose oxidase enzymes on different polysaccharides.
Figure 10B:
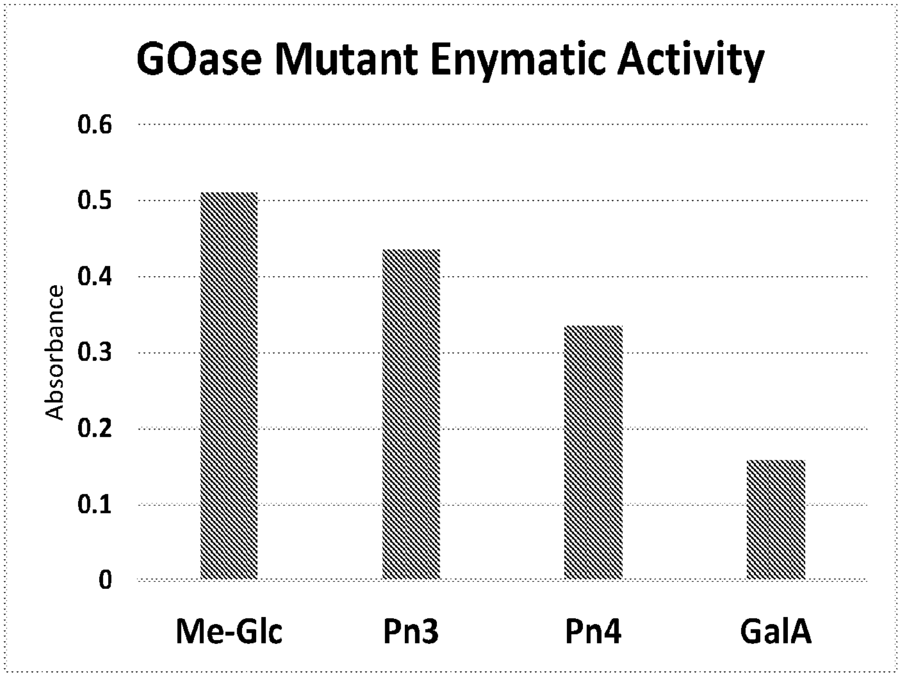

FIG. 10 shows an ABTS enzyme assay using both the wildtype Galactose Oxidase (GOase, FIG. 10A) and the mutated form (FIG. 10B). The assay was performed using either lactose or methylglucoside (Me-Glc) as a positive control and Galacturonic Acid (GalA) as a negative control. These data highlight the enzymatic activity on three clinically relevant serotypes of *S. pneumoniae.*

Using this chemoenzymatic approach, a great number of pathogenic bacterial capsular polysaccharides can be targeted using one of the two oxidases. Examples of bacterial capsular polysaccharides that can be oxidized using the galactose oxidase include *S. pneumoniae* serotypes 2, 3, 4, 5, 6A, 6B, 6C, 6D, 7A, 7F, 8, 9N, 10A, 12F, 13, 14, 15A, 15A, 15F, 17A, 17F, 19A, 19C, 19F, 22F, 32A, 32F, 33A, 33B, 33C, 33D, 33F, 35A, 37, 39, and 42; *Neisseria meningitidis* serogroups Y and W135; *S. agalactiae* (group B *Streptococcus*) type II and IV; and *Shigella flexneri* serotypes D1, B4, B5, B14, D3, O164, O40, D11, D13, X, Xv, 2A LPS.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed:

1. A multimer comprising a first peptide that is an amino acid sequence having at least 80% identity to SEQ ID NO:12, 10, 11, or 13 and a second peptide that is an amino acid sequence having at least 80% identity to SEQ ID NO: 12, 10, 11, or 13, wherein the first and second peptides are immediately adjacent and covalently joined, or wherein a spacer is present between the first peptide and the second peptide, wherein the spacer comprises a non-amino acid compound or no greater than 10 amino acids.

2. The multimer of claim 1, wherein the spacer comprises a cleavable sequence.

3. The multimer of claim 2, wherein the cleavable sequence comprises a cathepsin-sensitive sequence.

4. The multimer of claim 1, wherein the spacer comprises an acid labile chemical moiety.

5. The multimer of claim 1, wherein the multimer comprises a cysteine residue at one or more N-terminal ends, a valine residue at one or more C-terminal ends, or a combination thereof.

6. The multimer of claim 1, wherein the multimer comprises at least one covalently attached antigen, wherein the antigen comprises a capsular polysaccharide.

7. The multimer of claim 6, wherein the capsular polysaccharide comprises a *S. pneumoniae* polysaccharide.

8. The multimer of claim 7, wherein the *S. pneumoniae* polysaccharide is chosen from a *S. pneumoniae* of serotype 2, 3, 4, 5, 6A, 6B, 6C, 6D, 7A, 7F, 8, 9N, 10A, 12F, 13, 14, 15A, 15F, 17A, 17F, 19A, 19C, 19F, 22F, 32A, 32F, 33A, 33B, 33C, 33D, 33F, 35A, 37, 39, and 42.

9. The multimer of claim 6, wherein the capsular polysaccharide is chosen from *Neisseria meningitidis* serogroup Y, *N. meningitidis* serogroup W135, *S. agalactiae* type II, *S. agalactiae* type IV, *Shigella flexneri* serotype D1, *Shigella flexneri* serotype B4, *Shigella flexneri* serotype B5, *Shigella flexneri* serotype B14, *Shigella flexneri* serotype D3, *Shigella flexneri* serotype 0164, *Shigella flexneri* serotype 040, *Shigella flexneri* serotype D11, *Shigella flexneri* serotype D13, *Shigella flexneri* serotype X, *Shigella flexneri* serotype Xv, and *Shigella flexneri* serotype 2A LPS.

10. A composition comprising the multimer of claim 1 and a pharmaceutically acceptable carrier.

11. The composition of claim 10, further comprising an adjuvant.

12. A method for increasing the antigenicity of a compound, comprising attaching the multimer of claim 1 to a capsular polysaccharide, wherein the attaching comprises:

exposing the polysaccharide to a galactose oxidase under conditions suitable for oxidizing the polysaccharide, and combining the oxidized polysaccharide and the multimer under conditions suitable for conjugating the oxidized polysaccharide to the multimer.

13. The method of claim 12, wherein the capsular polysaccharide comprises a *S. pneumoniae* polysaccharide.

14. The method of claim 13, wherein the *S. pneumoniae* polysaccharide is chosen from a *S. pneumoniae* of serotype 2, 3, 4, 5, 6A, 6B, 6C, 6D, 7A, 7F, 8, 9N, 10A, 12F, 13, 14, 15A, 15F, 17A, 17F, 19A, 19C, 19F, 22F, 32A, 32F, 33A, 33B, 33C, 33D, 33F, 35A, 37, 39, and 42.

15. The method of claim 12, wherein the capsular polysaccharide is chosen from *Neisseria meningitidis* serogroup Y, *N. meningitidis* serogroup W135, *S. agalactiae* type II, *S. agalactiae* type IV, *Shigella flexneri* serotype D1, *Shigella flexneri* serotype B4, *Shigella flexneri* serotype B5, *Shigella flexneri* serotype B 14, *Shigella flexneri* serotype D3, *Shigella flexneri* serotype 0164, *Shigella flexneri* serotype 040, *Shigella flexneri* serotype D11, *Shigella flexneri* serotype D13, *Shigella flexneri* serotype X, *Shigella flexneri* serotype Xv, and *Shigella flexneri* serotype 2A LPS.

16. The method of claim 12, wherein the polysaccharide comprises one or more terminal galactose residues, one or more terminal glucose residues, one or more terminal n-acetylglucosamine residues, one or more terminal mannose residues, one or more terminal n-acetylmannosamine residues, or a combination thereof.

17. A multimer comprising a first peptide and a second peptide, wherein the first peptide comprises an amino acid sequence having at least 80% identity to SEQ ID NO:12, 10, 11, or 13 and no greater than 30 consecutive amino acids from SEQ ID NO:2, and wherein the second peptide comprises an amino acid sequence having at least 80% identity to SEQ ID NO:12, 10, 11, or 13 and no greater than 30 consecutive amino acids from SEQ ID NO:2.

* * * * *